United States Patent
Liao et al.

(10) Patent No.: US 7,335,487 B2
(45) Date of Patent: Feb. 26, 2008

(54) SWEET TASTE RECEPTORS

(75) Inventors: Jiayu Liao, Carlsbad, CA (US); Sheng Ding, San Diego, CA (US); Peter G. Schultz, La Jolla, CA (US)

(73) Assignees: IRM LLC, Hamilton (BM); The Scripps Research Institute, La Jolla, CA (US)

( * ) Notice: Subject to any disclaimer, the term of this patent is extended or adjusted under 35 U.S.C. 154(b) by 677 days.

(21) Appl. No.: 10/246,785

(22) Filed: Sep. 17, 2002

(65) Prior Publication Data

US 2003/0148448 A1 Aug. 7, 2003

Related U.S. Application Data

(60) Provisional application No. 60/323,450, filed on Sep. 18, 2001.

(51) Int. Cl.
C07K 14/705 (2006.01)
C12N 15/12 (2006.01)

(52) U.S. Cl. ........................ 435/69.1; 530/350
(58) Field of Classification Search .................. None
See application file for complete search history.

(56) References Cited

U.S. PATENT DOCUMENTS

| | | | |
|---|---|---|---|
| 6,383,778 B1 | 5/2002 | Zuker et al. | |
| 6,558,910 B2 | 5/2003 | Zuker et al. | |
| 6,955,887 B2 * | 10/2005 | Adler et al. | 435/7.2 |
| 2002/0086300 A1 | 7/2002 | Adler et al. | |
| 2002/0094551 A1 | 7/2002 | Adler | |
| 2002/0119526 A1 | 8/2002 | Zuker et al. | |
| 2002/0160424 A1 | 10/2002 | Adler et al. | |
| 2002/0164645 A1 | 11/2002 | Zuker et al. | |
| 2002/0168635 A1 | 11/2002 | Zuker et al. | |
| 2003/0008344 A1 | 1/2003 | Adler et al. | |
| 2003/0022288 A1 | 1/2003 | Zuker et al. | |
| 2003/0036630 A1 | 2/2003 | Zuker et al. | |
| 2003/0040045 A1 | 2/2003 | Zuker et al. | |
| 2004/0175792 A1 | 9/2004 | Zoller et al. | |

FOREIGN PATENT DOCUMENTS

| | | |
|---|---|---|
| WO | WO 00/06592 A1 | 2/2000 |
| WO | WO 00/06593 A1 | 2/2000 |
| WO | WO 00/06719 A1 | 2/2000 |
| WO | WO 01/08050 A2 | 3/2001 |
| WO | WO 01/66563 A2 | 9/2001 |
| WO | WO 01/77292 A2 | 10/2001 |
| WO | WO 01/77676 A1 | 10/2001 |
| WO | WO 02/054069 A1 | 7/2002 |
| WO | WO 02/064631 A2 | 8/2002 |
| WO | WO 03/001876 A2 | 1/2003 |
| WO | WO 03/004992 A2 | 1/2003 |

OTHER PUBLICATIONS

Adler et al.,"A Novel Family of MammalianTast Receptors" *Cell* 100:693-702, 2000.
Avenet et al., "Amiloride-Blockable Sodium Currents in Isolated Taste Receptor Cells" *J. Memb. Biol.* 105:245-255, 1988.
Bachmanov, A., "Sucrose consumption in mice: major influence of two genetic loci affecting peripheral sensory response" *Mamm. Genome* 8:545-548, 1997.
Bernhardt et al., "Change in $IP_3$ and cytosolic $Ca^{2+}$ in response to sugars and non-sugar sweeteners in transduction of sweet taste in the rat" *J. Physiol.* 490:325-336, 1996.
Brown et al., "Cloning and characterization of an extracellular $Ca^{2+}$-sensing receptor from bovine parathyroid" *Nature* 366:575-580, 1993.
Buck, L., "The Molecular Architecture of Odor and Pheromone Sensing in Mammals" *Cell* 100:611-6, 2000.
Cagan, Robert H., Ed., *Neural Mechanisms in Taste*, Chapter 4: Taste Modifiers and Sweet Proteins, CRC Press, Inc., Boca Raton, FL, 1989.
Chandrashekar, J. et al., "T2Rs Function as Bitter Taste Receptors" *Cell* 100:703-711, 2000.
Chaudharri et al., "A metabotropic glutamate receptor variant functions as a taste receptor" *Nature Neurosci.* 3:113-119, 2000.
Doolin et al., "Distribution and Characterization of Functional Amiloride-sensitive Sodium Channels in Rat Tongue" *J. Gen. Physiol.* 107:545-554, 1996.
Firestein, "The good taste of genomics" *Nature* 404:552-553, 2000.
Formaker et al., "An analysis of Residual NaCl taste response after amiloride" *Am. J. Physiol* 255:1002-1007, 1988.
Fuller, J., "Single-Locus Control of Saccharin Preference in Mice" *J. Hered.* 65:33-36, 1974.
Gilbertson et al., "Proton Currents through Amiloride-sensitive Na Channels in Hamster Taste Cells" *J. Gen. Physiol.* 100:803-824, 1992.
Gilbertson et al., "The molecular physiology of taste transduction" *Curr. Opin. Neurobiol.* 10:519-527, 2000.
Heck et al., "Salt Taste Transduction Occurs Through an Amiloride-Sensitive Sodium Transport Pathway" *Science* 223: 403-405, 1984.
Hoon et al., "Functional expression of the taste specific G-proein, α-gustducin" *Biochem. J.* 309:629-636, 1995.
Hoon et al., "Putative Mammalian Taste Receptors: A Class of Taste-Specific GPCRs with Distant Topographic Selectivity" *Cell* 96:541-552, 1999.
Kinnamon et al., "Apical localization of $K^+$ channels in taste cells provides the basis for sour taste transduction" *Proc. Natl. Acad. Sci. USA* 85:7023-7027, 1988.
Kinnamon et al., "Chemosensory Transduction Mechanisms in Taste" *Annu. Rev. Physiol.* 54:715-731, 1992.
Li et al., "Hi-resolution genetic mapping of the saccharin preference locus (*Sac*) and the putative sweet taste receptor (T1R1) gene (*Gpr70*) to mouse distal Chromosome 4" *Mamm. Genome* 12: 13-15, 2001.

(Continued)

*Primary Examiner*—John D. Ulm
(74) *Attorney, Agent, or Firm*—Timothy L. Smith, Genomics Institute of the Novartis Research Foundation

(57) ABSTRACT

This invention provides novel genes and polypeptides of the sweet receptor family, methods for production of the polypeptides, methods for screening compounds that specifically bind to and/or modulate the activity of these polypeptides; and antibodies specific for the polypeptides.

15 Claims, 7 Drawing Sheets

OTHER PUBLICATIONS

Li et al., "Human receptors for sweet and umami taste" *Proc. Natl. Acad. Sci.* 99: 4692-4696, 2002.

Lindemann, "Taste Reception" *Physiol. Rev.* 76:718-766, 1996.

Lush et al., "The genetics of tasting in mice VII. Glycine revisited, and the chromosomal location of *Sac and Soa*" *Genet. Res.* 66:167-174, 1995.

Matsunami et al., "A Multigene Family Encoding a Diverse Array of Putative Pheromone Receptors in Mammals" *Cell* 90: 775-784, 1997.

Matsunami et al., "A family of candidate taste receptors in human and mouse" *Nature* 404:601-603, 2000.

Max et al., "*Tas1r3*, encoding a new candidate taste receptor, is allelic to the sweet responsiveness locus *Sac*" *Nature Genetics*, 28:58-63, 2001.

Montmayeur et al., "A candidate taste receptor gene near a sweet taste locus" *Nature Neuroscience*, 4:492-498, 2001.

Nelson, et al., "Mammalian Sweet Taste Receptors" *Cell* 106:381-390, 2001.

Ruiz-Avila et al., "Coupling of bitter receptor to phosphodiesterase through transducin in taste receptor cells" *Nature* 376:80-85, 1995.

Striem et al., "Sweet tastants stimulate adenylate cyclase coupled to GTP-binding protein in rat tongue membranes" *Biochem. J.* 260:121-126, 1989.

Spielman et al., "Rapid kinetics of second messenger production in bitter taste" *Am. J. Physiol.* 270:C926-C931, 1996.

Wong et al., "Transduction of bitter and sweet taste by gustducin" *Nature* 381:796-800, 1996.

Xu, et al. (2004) "Different function roles of T1R subunits in heterometic taste receptors" *PNAS*, 101(39):14258-14263.

\* cited by examiner

```
hT1R1    1  MLLCTARLVG-LQLLLSCCWAFACHSTESSPDFTLPGDYLLAGLFPLHSGCLQVRHR--P
mT1R1    1  MLFWAAHLLLSLQLAVAYCWAFSCQRTESSPGFSLPGDFLLAGLFSLHADCLQVRHR--P
rT1R1    1  MLFWAAHLLLSLQL--VYCWAFSCQRTESSPGFSLPGDFLLAGLFSLHGDCLQVRHR--P
hT1R2    1  --MGPRAKTICSLFFLLWVLAEP---AENSD-FYLPGDYLLGGLFSLHANMKGIVHLNFL
mT1R2    1  --MGPQARTLHLLFLLLHALPKPVMLVGNSD-FHLAGDYLLGGLFTLHANVKSVSHLSYL
rT1R2    1  --MGPQARTLCLLSLLHVLPKPKGLVENSD-FHLAGDYLLGGLFTLHANVKSISHLSYL
hT1R3    1  ----MLCPAVLGLSLWALLHPGTGAPLCLSQQLRMKGDYVLGGLFPLGEAEEAGLRSR--
mT1R3    1  ----MPALAIMGLSLAAFLELGMGASLCLSQQFKAQGDYILGGLFPLGSTEEATLNQR-- hT1R1   58  EVTLCDRSCSFNEHGYHLFQAMRLGVEEINNSTALLPNITLGYQLYDVCSD-SANVYATL
mT1R1   59  LVTSCDRSDSFNGHGYHLFQAMRFTVEEINNSTALLPNITLGYELYDVCSE-SSNVYATL
rT1R1   57  LVTSCDRPDSFNGHGYHLFQAMRFTVEEINNSSALLPNITLGYELYDVCSE-SANVYATL
hT1R2   55  QVPMCK-EYEVKVIGYNLMQAMRFAVEEINNDSSLLPGVLLGYEIVDVCYI-SNNVQPVL
mT1R2   58  QVPKCN-EYNMKVLGYNLMQAMRFAVEEINNCSSLLPGVLLGYEMVDVCYL-SNNIQPGL
rT1R2   58  QVPKCN-EFTMKVLGYNLMQAMRFAVEEINNCSSLLPGVLLGYEMVDVCYL-SNNIHPGL
hT1R3   55  TRPSSPVCTRFSSNGLLWALAMKMAVEEINNKSDLLPGLRLGYDLFDTCSEPVVAMKPSL
mT1R3   55  TQPNSIPCNRFSPLGLFLAMAMKMAVEEINNGSALLPGLRLGYDLFDTCSEPVVTMKSSL hT1R1  117  RVLSLPGQHHIELQGDLLHYSPTVLAVIGPDSTNRAATTAALLSPFLVPMLISYAASSET
mT1R1  118  RVLAQQGTGHLEMQRDLRNHSSKVVALIGPDNTDHAVTTAALLSPFLMP-LVSYEASSVI
rT1R1  116  RVLALQGPRHIEIQKDLRNHSSKVVAFIGPDNTDHAVTTAALLGPFLMP-LVSYEASSVV
hT1R2  113  YFLAH-CDNLLPIQEDYSNYISRAVAVIGPDNSESVMTVANFLSLFLLP-QITYSATSDE
mT1R2  116  YFLSQ-IDDFLPILKDYSQYRPQVVAVIGPDNSESAITVSNILSYFLVP-QVTYSAIDDK
rT1R2  116  YFLAQ-DDDLLPILKDYSQYMPHVVAVIGPDNSESAITVSNILSHFLIP-QITYSAISDK
hT1R3  115  MFLAKAGSRDIAAYCNYTQYQPRVLAVIGPHSSELAMVTGKFFSFLMP-QVSYGASMEL
mT1R3  115  MFLAKVGSQSIAAYCNYTQYQPRVLAVIGPHSSELALITGKFFSFLMP-QVSYSASMDR hT1R1  177  LSVKRQYPSFLR-TIPNDKYQVETMVLLLQKFGWTWISLVGSSDDYGQLGVQALENQATG
mT1R1  177  LSGKRKFPSFLR-TIPSDKYQVEVIVRLLQSFGWVWISLVGSYGDYGQLGVQALEELATP
rT1R1  175  LSAKRKFPSFLR-TVPSDRHQVEVMVQLLQSFGWVWISLIGSYGDYGQLGVQALEELAVP
hT1R2  171  LRDKVRFPALLR-TTPSADHHIEAMVQLMLHFQWNWIIVLVSSDTYGRDNGQLLGERVAR
mT1R2  174  LRDKRRFPAMLRTVVPSATHHIEAMVQLMVHFQWNWIVVLVSDDDYGRENSHLLSQRLIN
rT1R2  174  LRDKRHFPSMLR-TVPSATHHIEAMVQLMVHFQWNWIVVLVSDDDYGRENSHLLSQRLTK
hT1R3  174  LSARETFPSFFR-TVPSDRVQLTAAAELLQEFGWNWVAALGSDDEYGRQGISIFSALAAA
mT1R3  174  LSDRETFPSFFR-TVPSDRVQLQAVVTLLQNFSWNWVAALGSDDDYGREGLSIFSSLANA hT1R1  236  Q-GICIAFKDIMPFSAQVG------DERMQCLMRHLAQAGATVVVVFSSRQLARVFFESV
mT1R1  236  R-GICVAFKDVVPLSAQAG------DPRMQRMMLRLARARTTVVVVFSNRHLAGVFFRSV
rT1R1  234  R-GICVAFKDIVPFSARVG------DPRMQSMMQHLAQARTTVVVVFSNRHLARVFFRSV
hT1R2  230  R-DICIAFQETLPTLQPNQNMTSEERQRLVTIVDKLQQSTARVVVVFSPDLTLYHFFNEV
mT1R2  234  TGDICIAFQEVLPVPEPNQAVRPEEQDQLDNILDKLRRTSARVVVVFSPELSLHNFFREV
rT1R2  233  TSDICIAFQEVLPIPESSQVMRSEEQRQLDNILDKLRRTSARVVVVFSPELSLYSFFHEV
hT1R3  233  R-GICIAHEGLVPLPRADD----SRLGKVQDVLHQVNQSSVQVVLLFASVHAAHALFNYS
mT1R3  233  R-GICIAHEGLVPQHDTSG----QQLGKVLDVLRQVNQSKVQVVVLFASARAVYSLFSYS hT1R1  289  VLTNLTGKVWVASEAWALSRHITGVPGIQRIGMVLGVAIQKRAVPGLKAFEEAYARADKE
mT1R1  289  VLANLTGKVWIASEDWAISTYITNVPGIQGIGTVLGVAIQQRQVPGLKEFEESYVQAVTG
rT1R1  287  VLANLTGKVWVASEDWAISTYITSVTGIQGIGTVLGVAVQQRQVPGLKEFEESYVRAVTA
hT1R2  289  LRQNFTCAVVLIASESWAIDPVLHNLTELRHLGTFLGITIQSVPIPGFSEFREWGPQAGP
mT1R2  294  LRWNFTGFVWIASESWAIDPVLHNLTELRHTGTFLGVTIQRVSIPGFSQFRVRHDKPEYP
rT1R2  293  LRWNFTGFVWIASESWAIDPVLHNLTELRHTGTFLGVTIQRVSIPGFSQFRVRRDKPGYP
hT1R3  288  ISSRLSPKVWVASEAWLTSDLVMGLPGMAQMGTVLGFLQRGAQLHEFPQYVKTHLALATD
mT1R3  288  IHHGLSPKVWVASESWLTSDLVMTLPNIARVGTVLGFLQRGALLPEFSHYVETHLALAAD
```

Fig. 1A

```
hT1R1  349  APRPCHKG------SWCSSNQLCRECQAFMAHTMPKLKAFS------MSSAYNAYRAVYA
mT1R1  349  APRTCPEC------SWCGTNQLCRECHAFTTWNMPELGAFS------MSAAYNVYEAVYA
rT1R1  347  APSACPEC------SWCSTNQLCRECHTFTTRNMPTLGAFS------MSAAYRVYEAVYA
hT1R2  349  PLSRFSQS------YTC--NQECDNCLNATLSFNTILRLSG------ERVVYSVYSAVYA
mT1R2  354  MPNETSLR------TTC--NQDCDACMNITESFNNVLMLSG------ERVVYSVYSAVYA
rT1R2  353  VPNTINLR------TTC--NQDCDACLNTTKSFNNILTLSG------ERVVYSVYSAVYA
hT1R3  348  PAFCSALGEREQGLEEDVVGQRCPQCDCITLQNVSAGLN-------HHQTFSVYAAVYS
mT1R3  348  PAFCASLN-AELDLEEHVMGQRCPRCDDIMLQNLSSGLLQNLSAGQLHHQIFATYAAVYS hT1R1  397  VAHGLHQLLGCASGACSRGRVYP-WQ-LEQIHVKHFLLHKDTVAFNDNRDPLSSYNIIAW
mT1R1  397  VAHGLHQLLGCTSGTCARGPVYP-WQLLQQIYKVNFLLHKKTVAFDDNGDPLGYYDIIAW
rT1R1  395  VAHGLHQLLGCTSEICSRGPVYP-WQLLQQIYKVNFLLHENTVAFDDNGDTLGYYDIIAW
hT1R2  395  VAHALHSLLGCDKSTCTKRVVYP-WQLLEEIWKVNFTLLDHQIFFDPQGDVALHLEIVQW
mT1R2  400  VAHTLHRLLHCNQVRCTKQIVYPPWQLLREIWHVNFTLLGNQLFFDEQGDMPMLLDIIQW
rT1R2  399  VAHALHRLLGCNRVRCTKQKVYP-WQLLREIWHVNFTLLGNRLFFDQQGDMPMLLDIIQW
hT1R3  400  VAQALHNTLQCNASGCPAQDPVKPWQLLENMYNLTFHVGGLPLRFDSSGNVDMEYDLKLW
mT1R3  407  VAQALHNTLQCNVSHCHVSEHVLPWQLLENMYNMSFHARDLTLQFDAEGNVDMEYDLKMW hT1R1  455  DWNGPKWTFTVLGSSTWSPVQLNINETKIQWHGKDNQEPSLCVPATVLKGTSEWLRVSIT
mT1R1  456  DWNCPEWTFEVIGSASLSPVHLDINKTKIQWHGKNNQVPVSVCTRDCLEGHHRLVMGSHH
rT1R1  454  DWNGPEWTFEIIGSASLSPVHLDINKTKIQWHGKNNQVPVSVCTTDCLAGHHRVVVGSHH
hT1R2  454  QWDRSQNPFQSVASVYPLQRQLKN-IQDISWHTINNTIPMSMCSKRCQSGQKKKPVGIHV
mT1R2  460  QWGLSQNPFQSIASVSPTTETRLTY-ISNVSWYTPNNTVPISMCSKSCQPGQMKKPIGLHP
rT1R2  458  QWDLSQNPFQSIASVSPTSKRLTY-INNVSWYTPNNTVPVSMCSKSCQPGQMKKSVGLHP
hT1R3  460  VWQCSVPRLHDVGRFNG---SLRTERLKIRWHT--SDKPVSRCSRQCQEGQVRRVKGFHS
mT1R3  467  VWQSPTPVLHTVGTFNG---TLQLQQSKMYWPG--NQVPVSQCSRQCKDGQVRRVKGFHS hT1R1  515  AALSVCPVG-GSWPS-LSDLYRCQPCGKEEWAPEGSQTCFPRTVVFLALREHTSWVLLAA
mT1R1  516  CCFECMPCEAGTFLN-TSELHTCQPCGTEEWAPEGSSACFSRTVEFLGWHEPISLVLLAA
rT1R1  514  CCFECVPCEAGTFLN-MSELHICQPCGTEEWAPKESTTCFPRTVEFLAWHEPISLVLLAA
hT1R2  513  CCFECLDCLPGTFLNHTEDEYECQACPNNEWSYQSETSCFKRQLVFLEWHEAPTIAVALL
mT1R2  519  CCFECQDCPPGTYLNKSSVSYKNNIACFKRRLAFLEWHEVPTIVVTIL
rT1R2  517  CCFECLDCMPGTYLNRSADEFNCLSCPGSMWSYKNDITCFQRRPTFLEWHEVPTIVVAIL
hT1R3  515  CCYDCVDCEAGSYRQ-NPDDIACTFCGQDEWSPERSTRCFRRRSRFLAWGEPAVLLLLL
mT1R3  522  CCYDCVDCKAGSYRK-HPDDFTCTPCNQDQWSPEKSTACLPRRPKFLAWGEPVVLSLLLL

TM 1                            TM2
hT1R1  573  NTLLLLLLLLCTAGLFAWHLDTPVVRSAGGRLCFLMLGSLAAGSGSLYGFFGEPTRPACLL
mT1R1  575  NTLLLLLLICTAGLFAWRLHTPVVRSAGGRLCFLMLGSLVAGSCSLYSFFGEPTVPACLL
rT1R1  573  NTLLLLLLVCTAGLFAWHFHTPVVRSAGGRLCFLMLGSCSFYSFFGEPTVPACLL
hT1R2  573  AALGFISTLAIVIFWRHFQTPIVRSAGGPMCFLMLTLLLVAYMVPVYVGPPKVSTCLC
mT1R2  579  AALGFISTLAIDLIFWRHFQTPMVRSVGGPMCFLMLVPLLDAFGNVPVYVGPPTVFSCFV
rT1R2  577  AALGFFSTLAILFIFWRHFQTPMVRSAGGPMCFLMLVPLLLAFGMVPVYVGPPTVFSCFC
hT1R3  574  LSTAIGLVLAALGLFVHHRDSPLVQASGGPLACFGLVCLGLVCLSVLLFPGQPSPARCLA
mT1R3  581  LCTVLGTALAALGLSVHHWDSPLVQASGGSQFCFGLICLGLFCLSVLLFPGRPSSASCLA

TM3                             TM4
hT1R1  633  RQALFALGFTIFLSCLTVRSFQLIIIFKFSTKVPTFYHAWVQNHGAGLFVMISSAAQLLI
mT1R1  635  RQPLFSLGEAIFLSCLTTIRSFQLVIIIFKFSTKVPTFYHTWAQNHGAGIFVIVSSTVHLFL
rT1R1  633  RQPLFSLGEAIFLSCLTTIRSFQLVIIFKFSTKVPTFYRTWAQNHGAGLFVIVSSTVHLLI
hT1R2  633  RQALFPLCFTICLSCIAVRSFQIVAFKMASRPPRAYSYWMRYQGPYVSMAFITAVKVMI
mT1R2  639  RQAFFTVCFSVCLSCITVRSFQIVCVFKMARRLPSAYGFWMRYHGPYVVFVAFITVKVAL
rT1R2  637  RQAFFTVCFSICLSCITVRSFQIVCVFKMARRLPSAYSFWMRYHGPYVVFVAFITAIKVAL
hT1R3  634  QQPLSHLPLICGLSTLFLQAAEIFVESELPLSWADRLSGCLRGPWAWLVVLLAMLVEVAL
mT1R3  641  QQPMAHLPLICGLSTLFLQAAETFVESELPLSWANWLCSYLRGLWAWLVVLLATFVEAAL
```

Fig. 1B

```
                              TM5
hT1R1  693 CLTWLVVWTPLPA-REYQRFPHLVMLECTETNSLGFILAFLYNGLLSISAFACSYLGKDL
mT1R1  695 CLTWLAMWTPRPT-REYQRFPHLVILECTEVNSVGFLVAFAHNILLSISTFVCSYLGKEL
rT1R1  693 CLTWLVMWTPRPT-REYQRFPHLVILECTEVNSVGFLLAFTHNILLSISTFVCSYLGKEL
hT1R2  693 VVIGMLATGLSPTTRTDPDDPKITIVSCNPNYRNSLLFNTSLDLLLSVVGFSFAYMGKEL
mT1R2  699 VAGNMLATTINPIGRTDPDDPNLIILSCHPNYRNGLLFNTSMDLLLSVLGFSFAYVGKEL
rT1R2  697 VVGNMLATTINPIGRTDPDDPNIMILSCHPNYRNGLLFNTSMDLLLSVLGFSFAYMGKEL
hT1R3  694 CTWYLVAFPPEVV-TDWHMLPTEALVHCRTRSWVSFGLAHATNATLAFLCFLGTFLVRSQ
mT1R3  701 CAWYLIAFPPEVV-TDWSVLPTEVLEHCHVRSWVSLGLVHITNAMLAFLCFLGTFLVQSQ

TM6                             TM7
hT1R1  752 PENYNEAKCVTFSLLFNFVSWIAFFTTASVYDGKYLPAANMMAGLSSLSSGFGGYFLPKC
mT1R1  754 PENYNEAKCVTFSLLLHFVSWIAFFTMSSIYQGSYLPAVNVLAGLATLSGGFSGYFLPKC
rT1R1  752 PENYNEAKCVTFSLLLNFVSWIAFFTMASIYQGSYLPAVNVLAGLTTLSGGFSGYFLPKC
hT1R2  753 PTNYNEAKFITLSMTFYFTSSVSLCTFMSAYSGVLVTIVDLLVTVLNLLAISLGYFGPKC
mT1R2  759 PTNYNEAKFITLSMTFSFTSSISLCTFMSVHDGVLVTIMDLLVTVLNFLAIGLGYFGPKC
rT1R2  757 PTNYNEAKFITLSMTFSFTSSISLCTFMSVHDGVLVTIMDLLVTVLNFLAIGLGYFGPKC
hT1R3  753 PGRYNRARGLTFAMLAYFITWVSFVPLLANVQVVLRPAVQMGALLLCVLGILAAFHLPRC
mT1R3  760 PGRYNRARGLTFAMLAYFITWVSFVPLLANVQVAYQPAVQMGAILVCALGILVTFHLPKC hT1R1  812 YVILCRPDLNSTEHFQASIQDYTRRCGST----------
mT1R1  814 YVILCRPELNNTEHFQASIQDYTRRCGTT----------
rT1R1  812 YVILCRPELNNTEHFQASIQDYTRRCGTT----------
hT1R2  813 YMILFYPERNTPAYFNSMIQGYTMRRD------------
mT1R2  819 YMILFIPERNTSAYFNSMIQGYTMRKS------------
rT1R2  817 YMILFYPERNTSAYFNSMIQGYTMRKS------------
hT1R3  813 YLLMRQPGLNTPEFFLGGGPGDAQGQNDGN-TGNQGKHE
mT1R3  820 YVLLWLPKLNTQEFFLGRNAKKAADENSGGGEAAQGHNE
```

Fig. 1C

```
ATGCTGCTCTGCACGGCTCGCCTGGTCGGCCTGCAGCTTCTCATTTCCTGCTGCTGGGCCTT
TGCCTGCCATAGCACGGAGTCTTCTCCTGACTTCACCCTCCCCGGAGATTACCTCCTGGCAG
GCCTGTTCCCTCTCCATTCTGGCTGTCTGCAGGTGAGGCACAGACCCGAGGTGACCCTGTGT
GACAGGTCTTGTAGCTTCAATGAGCATGGCTACCACCTCTTCCAGGCTATGCGGCTTGGGGT
TGAGGAGATAAACAACTCCACGGCCCTGCTGCCCAACATCACCCTGGGGTACCAGCTGTATG
ATGTGTGTTCTGACTCTGCCAATGTGTATGCCACGCTGAGAGTGCTCTCCCTGCCAGGGCAA
CACCACATAGAGCTCCAAGGAGACCTTCTCCACTATTCCCCTACGGTGCTGGCAGTGATTGG
GCCTGACAGCACCAACCGTGCTGCCACCACAGCCGCCCTGCTGAGCCCTTTCCTGGTGCCCA
TGCTTATTAGCTATGCGGCCAGCAGCGAGACGCTCAGCGTGAAGCGGCAGTATCCCTCTTTC
CTGCGCACCATCCCCAATGACAAGTACCAGGTGGAGACCATGGTGCTGCTGCTGCAGAAGTT
CGGGTGGACCTGGATCTCTCTGGTTGGCAGCAGTGACGACTATGGGCAGCTAGGGGTGCAGG
CACTGGAGAACCAGGCCACTGGTCAGGGGATCTGCATTGCTTTCAAGGACATCATGCCCTTC
TCTGCCCAGGTGGGCGATGAGAGGATGCAGTGCCTCATGCGCCACCTGGCCCAGGCCGGGGC
CACCGTCGTGGTTGTTTTTTCCAGCCGGCAGTTGGCCAGGGTGTTTTTCGAGTCCGTGGTGC
TGACCAACCTGACTGGCAAGGTGTGGGTCGCCTCAGAAGCCTGGGCCCTCTCCAGGCACATC
ACTGGGGTGCCCGGGATCCAGCGCATTGGGATGGTGCTGGGCGTGGCCATCCAGAAGAGGGC
TGTCCCTGGCCTGAAGGCGTTTGAAGAAGCCTATGCCCGGGCAGACAAGGAGGCCCCTAGGC
CTTGCCACAAGGGCTCCTGGTGCAGCAGCAATCAGCTCTGCAGAGAATGCCAAGCTTTCATG
GCACACACGATGCCCAAGCTCAAAGCCTTCTCCATGAGTTCTGCCTACAACGCATACCGGGC
TGTGTATGCGGTGGCCCATGGCCTCCACCAGCTCCTGGGCTGTGCCTCTGGAGCTTGTTCCA
GGGGCCGAGTCTACCCCTGGCAGTTGGAGCAGATCCACAAGGTGCATTTCCTTCTACACAAG
GACACTGTGGCGTTTAATGACAACAGAGATCCCCTCAGTAGCTATAACATAATTGCCTGGGA
CTGGAATGGACCCAAGTGGACCTTCACGGTCCTCGGTTCCTCCACATGGTCTCCAGTTCAGC
TAAACATAAATGAGACCAAAATCCAGTGGCACGGAAAGGACAACCAGGAACCAAGTCTGTGT
GTTCCAGCGACTGTCTTGAAGGGCACCAGCGAGTGGTTACGGGTTTCCATCACTGCTGCTTT
GAGTGTGTGCCCTGTGGGGGGTTCTTGGCCTTCCCTTTCAGACCTCTACAGATGCCAGCCTT
GTGGGAAAGAAGAGTGGGCACCTGAGGGAAGCCAGACCTGCTTCCCGCGCACTGTGGTGTTT
TTGGCTTTGCGTGAGCACACCTCTTGGGTGCTGCTGGCAGCTAACACGCTGCTGCTGCTGCT
GCTGCTTGGGACTGCTGGCCTGTTTGCCTGGCACCTAGACACCCCTGTGGTGAGGTCAGCAG
GGGGCCGCCTGTGCTTTCTTATGCTGGGCTCCCTGGCAGCAGGTAGTGGCAGCCTCTATGGC
TTCTTTGGGGAACCCACAAGGCCTGCGTGCTTGCTACGCCAGGCCCTCTTTGCCCTTGGTTT
CACCATCTTCCTGTCCTGCCTGACAGTTCGCTCATTCCAACTAATCATCATCTTCAAGTTTT
CCACCAAGGTACCTACATTCTACCACGCCTGGGTCCAAAACCACGGTGCTGGCCTGTTTGTG
ATGATCAGCTCAGCGGCCCAGCTGCTTATCTGTCTAACTTGGCTGGTGGTGTGGACCCCACT
GCCTGCTAGGGAATACCAGCGCTTCCCCCATCTGGTGATGCTTGAGTGCACAGAGACCAACT
CCCTGGGCTTCATACTGGCCTTCCTCTACAATGGCCTCCTCTCCATCAGTGCCTTTGCCTGC
AGCTACCTGGGTAAGGACTTGCCAGAGAACTACAACGAGGCCAATGTGTCACCTTCAGCCT
GCTCTTCAACTTCGTGTCCTGGATCGCCTTCTTCACCACGGCCAGCGTCTACGACGGCAAGT
ACCTGCCTGCGGCCAACATGATGGCTGGGCTGAGCAGCCTGAGCAGCGGCTTCGGTGGGTAT
TTTCTGCCTAAGTGCTACGTGATCCTCTGCCGCCCAGACCTCAACAGCACAGAGCACTTCCA
GGCCTCCATTCAGGACTACACGAGGCGCTGCGGCTCCACCTGA
```

Fig. 2A

```
ATGGGGCCCAGGGCAAAGACCATCTGCTCCCTGTTCTTCCTCCTATGGGTCCTGGCTGAGCC
GGCTGAGAACTCGGACTTCTACCTGCCTGGGGATTACCTCCTGGGTGGCCTCTTCTCCCTCC
ATGCCAACATGAAGGGCATTGTTCACCTTAACTTCCTGCAGGTGCCCATGTGCAAGGAGTAT
GAAGTGAAGGTGATAGGCTACAACCTCATGCAGGCCATGCGCTTTGCGGTGGAGGAGATCAA
CAATGACAGCAGCCTGCTGCCTGGTGTGCTGCTGGGCTATGAGATCGTGGATGTGTGCTACA
TCTCCAACAATGTCCAGCCGGTGCTCTACTTCCTGGCACACGGGGACAACCTCCTTCCCATC
CAAGAGGACTACAGTAACTACATTTCCCGTGCGGTGGCTGTCATTGGCCCTGACAACTCCGA
GTCTGTCATGACTGTGGCCAACTTCCTCTCCCTATTTCTCCTTCCACAGATCACCTACAGCG
CCATCAGCGATGAGCTGCGAGACAAGGTGCGCTTCCCGGCTTTGCTGCGTACCACACCCAGC
GCCGACCACCACATCGAGGCCATGGTGCAGCTGATGCTGCACTTCCGCTGGAACTGGATCAT
TGTGCTGGTGAGCAGCGACACCTATGGCCGCGACAATGGCCAGCTGCTTGGCGAGCGCGTGG
CCCGGCGCGACATCTGCATCGCCTTCCAGGAGACGCTGCCCACACTGCAGCCCAACCAGAAC
ATGACGTCAGAGGAGCGCCAGCGCCTGGTGACCATTGTGGACAAGCTGCAGCAGAGCACAGC
GCGCGTCGTGGTCGTGTTCTCGCCCGACCTGACCCTGTACCACTTCTTCAATGAGGTGCTGC
GCCAGAACTTCACTGGCGCCGTGTGGATCGCCTCCGAGTCCTGGGCCATCGACCCGGTCCTG
CACAACCTCACGGAGCTGCGCCACTTGGGCACCTTCCTGGGCATCACCATCCAGAGCGTGCC
CATCCCGGGCTTCAGTGAGTTCCGCGAGTGGGGCCCACAGGCTGGGCCGCCACCCCTCAGCA
GGACCAGCCAGAGCTATACCTGCAACCAGGAGTGCGACAACTGCCTGAACGCCACCTTGTCC
TTCAACACCATTCTCAGGCTCTCTGGGGAGCGTGTCGTCTACAGCGTGTACTCTGCGGTCTA
TGCTGTGGCCCATGCCCTGCACAGCCTCCTCGGCTGTGACAAAAGCACCTGCACCAAGAGGG
TGGTCTACCCCTGGCAGCTGCTTGAGGAGATCTGGAAGGTCAACTTCACTCTCCTGGACCAC
CAAATCTTCTTCGACCCGCAAGGGGACGTGGCTCTGCACTTGGAGATTGTCCAGTGGCAATG
GGACCGGAGCCAGAATCCCTTCCAGAGCGTCGCCTCCTACTACCCCCTGCAGCGACAGCTGA
AGAACATCCAAGACATCTCCTGGCACACCATCAACAACACGATCCCTATGTCCATGTGTTCC
AAGAGGTGCCAGTCAGGGCAAAAGAAGAAGCCTGTGGGCATCCACGTCTGCTGCTTCGAGTG
CATCGACTGCCTTCCCGGCACCTTCCTCAACCACACTGAAGATGAATATGAATGCCAGGCCT
GCCCGAATAACGAGTGGTCCTACCAGAGTGAGACCTCCTGCTTCAAGCGGCAGCTGGTCTTC
CTGGAATGGCATGAGGCACCCACCATCGCTGTGGCCCTGCTGGCCGCCCTGGGCTTCCTCAG
CACCCTGGCCATCCTGGTGATATTCTGGAGGCACTTCCAGACACCCATAGTTCGCTCGGCTG
GGGGCCCCATGTGCTTCCTGATGCTGACACTGCTGCTGGTGGCATACATGGTGGTCCCGGTG
TACGTGGGGCCGCCCAAGGTCTCCACCTGCCTCTGCCGCCAGGCCCTCTTTCCCCTCTGCTT
CACAATCTGCATCTCCTGTATCGCCGTGCGTTCTTTCCAGATCGTCTGCGCCTTCAAGATGG
CCAGCCGCTTCCCACGCGCCTACAGCTACTGGGTCCGCTACCAGGGGCCCTACGTCTCTATG
GCATTTATCACGGTACTCAAAATGGTCATTGTGGTAATTGGCATGCTGGCCACGGGCCTCAG
TCCCACCACCCGTACTGACCCCGATGACCCCAAGATCACAATTGTCTCCTGTAACCCCAACT
ACCGCAACAGCCTGCTGTTCAACACCAGCCTGGACCTGCTGCTCTCAGTGGTGGGTTTCAGC
TTCGCCTACATGGGCAAAGAGCTGCCCACCAACTACAACGAGGCAAGTTCATCACCCTCAG
CATGACCTTCTATTTCACCTCATCCGTCTCCCTCTGCACCTTCATGTCTGCCTACAGCGGGG
TGCTGGTCACCATCGTGGACCTCTTGGTCACTGTGCTCAACCTCCTGGCCATCAGCCTGGGC
TACTTCGGCCCCAAGTGCTACATGATCCTCTTCTACCCGGAGCGCAACACGCCCGCCTACTT
CAACAGCATGATCCAGGGCTACACCATGAGGAGGGACTAG
```

Fig. 2B

```
ATGCTGGGCCCTGCTGTCCTGGGCCTCAGCCTCTGGGCTCTCCTGCACCCTGGGACGGGGGC
CCCATTGTGCCTGTCACAGCAACTTAGGATGAAGGGGGACTACGTGCTGGGGGGGCTGTTCC
CCCTGGGCGAGGCCGAGGAGGCTGGCCTCCGCAGCCGGACACGGCCCAGCAGCCCTGTGTGC
ACCAGGTTCTCCTCAAACGGCCTGCTCTGGGCACTGGCCATGAAAATGGCCGTGGAGGAGAT
CAACAACAAGTCGGATCTGCTGCCCGGGCTGCGCCTGGGCTACGACCTCTTTGATACGTGCT
CGGAGCCTGTGGTGGCCATGAAGCCCAGCCTCATGTTCCTGGCCAAGGCAGGCAGCCGCGAC
ATCGCCGCCTACTGCAACTACACGCAGTACCAGCCCCGTGTGCTGGCTGTCATCGGGCCCCA
CTCGTCAGAGCTCGCCATGGTCACCGGCAAGTTCTTCAGCTTCTTCCTCATGCCCCAGGTCA
GCTACGGTGCTAGCATGGAGCTGCTGAGCGCCCGGGAGACCTTCCCCTCCTTCTTCCGCACC
GTGCCCAGCGACCGTGTGCAGCTGACGGCCGCCGCGGAGCTGCTGCAGGAGTTCGGCTGGAA
CTGGGTGGCCGCCCTGGGCAGCGACGACGAGTACGGCCGGCAGGGCCTGAGCATCTTCTCGG
CCCTGGCCGCGGCACGCGGCATCTGCATCGCGCACGAGGGCCTGGTGCCGCTGCCCCGTGCC
GATGACTCGCGGCTGGGGAAGGTGCAGGACGTCCTGCACCAGGTGAACCAGAGCAGCGTGCA
GGTGGTGCTGCTGTTCGCCTCCGTGCACGCCGCCCACGCCCTCTTCAACTACAGCATCAGCA
GCAGGCTCTCGCCCAAGGTGTGGGTGGCCAGCGAGGCCTGGCTGACCTCTGACCTGGTCATG
GGGCTGCCCGGCATGGCCCAGATGGGCACGGTGCTTGGCTTCCTCCAGAGGGGTGCCCAGCT
GCACGAGTTCCCCCAGTACGTGAAGACGCACCTGGCCCTGGCCACCGACCCGGCCTTCTGCT
CTGCCCTGGGCGAGAGGGAGCAGGGTCTGGAGGAGGACGTGGTGGGCCAGCGCTGCCCGCAG
TGTGACTGCATCACGCTGCAGAACGTGAGCGCAGGGCTAAATCACCACCAGACGTTCTCTGT
CTACGCAGCTGTGTATAGCGTGGCCCAGGCCCTGCACAACACTCTTCAGTGCAACGCCTCAG
GCTGCCCCGCGCAGGACCCCGTGAAGCCCTGGCAGCTCCTGGAGAACATGTACAACCTGACC
TTCCACGTGGGCGGGCTGCCGCTGCGGTTCGACAGCAGCGGAAACGTGGACATGGAGTACGA
CCTGAAGCTGTGGGTGTGGCAGGGCTCAGTGCCCAGGCTCCACGACGTGGGCAGGTTCAACG
GCAGCCTCAGGACAGAGCGCCTGAAGATCCGCTGGCACACGTCTGACAAGCCCGTGTCCCGG
TGCTCGCGGCAGTGCCAGGAGGGCCAGGTGCGCCGGGTCAAGGGGTTCCACTCCTGCTGCTA
CGACTGTGTGGACTGCGAGGCGGGCAGCTACCGGCAAAACCCAGACGACATCGCCTGCACCT
TTTGTGGCCAGGATGAGTGGTCCCCGGAGCGAAGCACACGCTGCTTCCGCCGCAGGTCTCGG
TTCCTGGCATGGGGCGAGCCGGCTGTGCTGCTGCTGCTCCTGCTGCTGAGCCTGGCGCTGGG
CCTTGTGCTGGCTGCTTTGGGGCTGTTCGTTCACCATCGGGACAGCCCACTGGTTCAGGCCT
CGGGGGGGCCCCTGGCCTGCTTTGGCCTGGTGTGCCTGGGCCTGGTCTGCCTCAGCGTCCTC
CTGTTCCCTGGCCAGCCCAGCCCTGCCCGATGCCTGGCCCAGCAGCCCTTGTCCCACCTCCC
GCTCACGGGCTGCCTGAGCACACTCTTCCTGCAGGCGGCCGAGATCTTCGTGGAGTCAGAAC
TGCCTCTGAGCTGGGCAGACCGGCTGAGTGGCTGCCTGCGGGGCCCTGGGCCTGGCTGGTG
GTGCTGCTGGCCATGCTGGTGGAGGTCGCACTGTGCACCTGGTACCTGGTGGCCTTCCCGCC
GGAGGTGGTGACGGACTGGCACATGCTGCCCACGGAGGCGCTGGTGCACTGCCGCACACGCT
CCTGGGTCAGCTTCGGCCTAGCGCACGCCACCAATGCCACGCTGGCCTTTCTCTGCTTCCTG
GGCACTTTCCTGGTGCGGAGCCAGCCGGGCCGCTACAACCGTGCCCGTGGCCTCACCTTTGC
CATGCTGGCCTACTTCATCACCTGGGTCTCCTTTGTGCCCCTCCTGGCCAATGTGCAGGTGG
TCCTCAGGCCCGCCGTGCAGATGGGCGCCCTCCTGCTCTGTGTCCTGGGCATCCTGGCTGCC
TTCCACCTGCCCAGGTGTTACCTGCTCATGCGGCAGCCAGGGCTCAACACCCCGAGTTCTT
CCTGGGAGGGGCCCTGGGGATGCCCAAGGCCAGAATGACGGGAACACAGGAAATCAGGGGA
AACATGAGT
```

Fig. 2C

SWEET TASTE RECEPTORS

CROSS-REFERENCE TO RELATED APPLICATIONS

This application is a Non-Provisional of U.S. Ser. No. 60/323,450, "Sweet Taste Receptors" by Liao and Schultz, filed Sep. 18, 2001, which is incorporated herein by reference in its entirety. The subject application claims priority to and benefit of U.S. Ser. No. 60/323,450.

FIELD OF THE INVENTION

This invention relates to novel sweet receptor nucleic acids and polypeptides. In particular, the invention relates to polypeptides that are homologous to other sweet receptors, nucleic acids encoding the polypeptides, vectors and host cells comprising the nucleic acids and antibodies that specifically bind to the polypeptides. The invention also relates to recombinant methods for producing the polypeptides and methods for identifying compounds that bind to and/or modulate the activity of the polypeptides.

BACKGROUND OF THE INVENTION

In mammals, there are three chemosensory systems (taste, olfactory and vomeronasal perceptions) that function to convert external chemical signals to specific neuronal activities. These neuronal signals are then integrated in different regions of brain and the output of these signals affect the organism's various innate behaviors, ranging from aversion and attraction to food or small volatile chemicals to reproductive actions. Among these chemosensory systems, taste perception provides immediate valuation of nutrients. Although the molecular universe of tastants consists of diverse chemical structures such as ions, small organic molecules, proteins, carbohydrates, amino acids, and lipids, it is generally believed that mammals have five basic taste modalities: sour, salty, bitter, sweet, and umami (glutamate) as described, e.g., in Lindemann, *Physiol. Rev.* 76:718-766, 1996; Kinnamon et al., *Annu. Rev. Physiol.* 54:715-731, 1992; and Gilbertson et al., *Curr. Opin. Neurobiol.* 10: 519-527, 2000.

The sensation of taste is initiated by the interaction of tastants with their receptors in the taste cells, which are clustered in onion-shape taste buds embedded within the lingual epithelium in tongue and palate as described, e.g., in Lindemann, supra. On the tongue, taste buds are topographically distributed into papillae in different locations of tongue. Fungiform papillae are located at the front of the tongue and contain a small number of taste buds; foliate papillae, containing dozens of taste buds, are localized along the posterior lateral edge of the tongue; and at the back of the tongue, circumvallate papillae contain thousands of taste buds. Classical physiological studies have found that fungiform papillae are sensitive to sweet, foliate papillae are sensitive to sour and bitter, and circumvallate papillae are particularly sensitive to bitter.

Each taste modality is thought to be mediated by distinct cell surface receptors that are expressed in a subset of taste cells. Electrophysiological and biochemical studies suggest that salty and sour tastants signal through $Na^+$ and $H^+$ membrane channels as described, e.g., in Heck et al. *Science* 223: 403-405, 1984; Avenet et al., *J. Memb. Biol.* 105:245-255, 1988, Doolin et al., *J. Gen. Physiol.* 107:545-554, 1996; Formaker et al., *Am. J. Physiol* 255:1002-1007, 1988; Kinnamon et al. *Proc. Natl. Acad. Sci. USA* 85:7023-7027, 1988; and Gilbertson et al., *J. Gen. Physiol.* 100:803-824, 1992. In contrast, bitter, sweet, and umami taste transduction are believed to involve G protein-coupled receptors (GPCR).

GPCRs are a class of seven-transmembrane proteins which transduce an extracellular signal, i.e., ligand binding to receptor, into a cellular response. Upon ligand binding to a GPCR, the GPCR activates an intracellular guanine nucleotide protein known as G-protein (guanine nucleotide binding protein), which mediates a response to the extracellular signal. G-proteins are heterotrimeric proteins composed of an alpha, beta and gamma subunit. The activated G protein alters the activity of various cellular effector enzymes (e.g., adenylate cyclase and phosphodiesterase), which in turn alters the levels of various second messengers (e.g., cAMP, cGMP, and inositol triphosphate ($IP_3$)).

Experiments with the bitter substance, denatonium, have shown that the secondary messages, cAMP and $IP_3$, are induced in response to bitter stimuli as described, e.g., in Spielamn et al., *Am. J. Physiol.* 270:C926-C931, 1996; and Ruiz-Avila et al., *Nature* 376:80-85, 1995. Other studies have revealed that gustducin, a G protein expressed in subpopulation of taste buds, can activate phosphodiesterase (PDE) and thereby decrease cNMP levels in response to bitter stimuli as described, e.g., in Ruiz-Avila et al, supra; and Hoon et al., *Biochem. J.* 309:629-636, 1995. These secondary messages, which are generally involved in G protein signaling, are consistent with the involvement of GPCRs in taste transduction. Sweet substances have also been shown to cause the elevation of the secondary messages, cAMP and $IP_3$, presumably in response to activation of G protein-coupled receptor cascades by Gs protein as described, e.g., in Striem et al., *Biochem. J.* 260:121-126, 1989; and Bernhardt et al., *J. Physiol.* 490:325-336, 1996. The involvement of G proteins in bitter and sweet transduction is also supported by the discovery that mice with a null allele of gustducin have an impaired ability to detect bitter and sweet substances as described, e.g., in Wong et al., *Nature* 381:796-800, 1996.

The involvement of G-protein coupled receptors in taste transduction has recently been confirmed by the discovery of three families of GPCRs expressed in mammalian taste bud cells, a number of which have been shown to be activated by bitter and glutamate tastants as described, e.g., in Firestein, *Nature* 404:552-553, 2000. A splice variant of a metabotropic glutamate receptor was cloned from rat taste bud and was shown to respond to monosodium L-glutamate when expressed in heterogonous cells as described, e.g., in Chaudharri et al., *Nature Neurosci.* 3:113-119, 2000. Two additional candidate taste receptors, T1R1 and T2R2, have been isolated from rat taste bud, and show distant homology with putative pheromone receptor V2Rs and metabotropic glutamate receptors, as described in Hoon et al., *Cell* 96:541-552, 1999. T1R1 and T2R2 were postulated to function as sweet and bitter receptors, respectively, based on their topographic distribution in the tongue as described, e.g., in Hoon et al., supra, 1999. Searches of the human and mouse genomes have identified another family of taste receptors (T2Rs) containing approximately 25 members as described, e.g., in Adler et al., Cell 100:693-702, 2000; and Matsunami et al., *Nature* 404:601-603, 2000. One receptor in this family, mT2R5, is specifically activated by the bitter substance cycloheximide, while the human hT2R4 and mouse mT2R8 respond to denatonium as described, e.g., in Chandrashekar et al., *Cell* 100:703-711, 2000.

Over the past few years, much effort has been directed toward the development of various sweeteners that interact with taste receptors to mimic natural sweet taste stimulants. See, Robert H. Cagan, Ed., *Neural Mechanisms in Taste*, Chapter 4, CRC Press, Inc., Boca Raton, Fla., 1989. Examples of sweeteners that have been developed to mimic sweet tastes are saccharin (an anhydride of o-sulfimide benzoic acid), monellin (a protein), aspartame (a peptide composed of aspartic acid and methyl ester of phenylalanine) and the thaumatins (also proteins). Many sweeteners developed to date are not suitable as food additives, however, because they are uneconomical, high in calories, carcinogenic or lose their sweetness when exposed to elevated temperatures for long periods, rendering them unsuitable for use in most baking applications.

Development of new sweeteners that mimic sweet (and other) tastes has been limited by a lack of knowledge of the taste cell proteins responsible for transducing the sweet taste modalities. Accordingly, the identification of new sweet taste receptors would enable the identification of the natural ligands, i.e., natural sweet tastants, of these proteins and the design of novel sweeteners that mimic sweet taste perception. The present invention fulfills these and other needs.

SUMMARY OF THE INVENTION

The present invention relates members of the sweet receptor family, in particular human sweet receptor 1 (hT1R1), human sweet receptor 2 (hT1R2) and human sweet receptor 3 (hT1R3) nucleic acids and polypeptides, vectors and host cells comprising the nucleic acids, antibodies to the polypeptides, and methods for producing the polypeptides. In another aspect, the present invention relates to methods for identifying agents that bind to and/or modulate the activity of these polypeptides, e.g., use of the polypeptides (e.g., when present in biological materials) as sensor or assay components to detect molecules that are perceived as sweet and/or that provide for glutamate (umami) detection. The invention also provides for rescue of sweet and/or umami taste function in cells that are defective in expression of hT1R1, hT1R2 or hT1R3, e.g., by expressing the polypeptides of the invention in the cells, e.g., from a recombinant construct. This cell rescue can be performed in vitro (e.g., in cell culture) or in vivo (e.g., in mammalian taste buds).

Accordingly, in a first aspect, the invention provides isolated or recombinant polypeptides (e.g., that comprises hT1R1, hT1R2 or hT1R3 function). These polypeptides can be characterized in any of a variety of related ways. For example, the polypeptides of the invention can include an amino acid sequence or subsequence that is at least 75% identical to an hT1R1 polypeptide (e.g., SEQ ID NO. 1), an hT1R2 polypeptide (e.g., SEQ ID NO.4), and/or an hT1R3 polypeptide (e.g., SEQ ID NO.7), e.g., as determined by BLASTP using default parameters (or another comparison algorithm or via manual alignment). Similarly, the polypeptides of the invention can include an amino acid sequence or subsequence that comprises one or more domains of an hT1R1 polypeptide, an hT1R2 polypeptide, or an hT1R3 polypeptide, e.g., where the hT1R1 polypeptide, the hT1R2 polypeptide, or the hT1R3 polypeptide comprises an amino acid sequence such as those of hT1R1, hT1R2 and/or hT1R3 (e.g., SEQ ID NO. 1, SEQ ID NO.4 and SEQ ID NO.7, respectively). In a related aspect, the polypeptides of the invention can include an amino acid sequence or subsequence that is at least 75% identical to a domain encoded by hT1R1, hT1R2 and/or hT1R3, (e.g., SEQ ID NO. 1, SEQ ID NO.4 or SEQ ID NO.7, respectively), e.g., as determined by BLASTP using default parameters, where the domain includes: an amino-terminal extracellular domain; an extracellular domain located between TM2 and TM3, between TM4 and TM5, or between TM6 and TM7; a transmembrane (TM) domain; an intracellular domain located between TM1 and TM2, between TM3 and TM4, or between TM5 and TM6; and/or a carboxyl-terminal intracellular domain. Any polypeptide of the invention optionally includes one or more of these domains. The polypeptides of the invention can also be defined by immunoreactivity, e.g., the polypeptides of the invention can include an amino acid sequence or subsequence that is specifically bound by an antibody that specifically binds to an amino acid such as hT1R1, hT1R2 and/or hT1R3 (e.g., SEQ ID NO. 1, SEQ ID NO.4, and/or SEQ ID NO.7, respectively) where the antibody is not specifically bound by an amino acid from the corresponding mouse or rat homologues (e.g., as represented at SEQ ID NO. 2, SEQ ID NO. 3, SEQ ID NO. 5, SEQ ID NO. 6, SEQ ID NO. 8, and/or SEQ ID NO. 9). Examples of polypeptides of the invention include the polypeptides encoded by amino acid sequences or subsequences that are encoded by SEQ ID NO. 10, SEQ ID NO. 11 and/or SEQ ID NO 12, and/or complementary sequences thereof. In general, the polypeptides of the invention can also be defined with respect to the nucleic acids that encode them, e.g., polypeptides of the invention can include an amino acid sequence or subsequence that is encoded by a first nucleic acid that specifically hybridizes to a second nucleic acid, wherein the second nucleic acid is a nucleic acid that encodes hT1R1, hT1R2 and/or hT1R3 (e.g., SEQ ID NO. 10, SEQ ID NO. 11 and/or SEQ ID NO 12), or a complement thereof, under stringent conditions, where the first nucleic acid hybridizes to the second nucleic acid under the stringent conditions with at least 5× an affinity that the first nucleic acid hybridizes to a third nucleic acid that encodes a mouse or rat homologue, e.g., an mT1R1 nucleic acid, an rT1R1 nucleic acid, an mT1R2 nucleic acid, an rT1R2 nucleic acid, an mT1R3 nucleic acid and/or a rT1R3 nucleic acid. Also encompassed within the polypeptides of the invention are any and all amino acid sequences or subsequences corresponding to a conservative variation of any of the amino acid sequences or subsequences noted above, e.g., an amino acid sequence such as SEQ ID NO. 1, SEQ ID NO.4, SEQ ID NO.7, or a conservative variation thereof.

In one aspect the polypeptide of the invention is a mature polypeptide, e.g., a mature hT1R1 protein, a mature hT1R2 protein, or a mature hT1R3 protein, e.g., a protein having an activity of the hT1R1, hT1R2 or hT1R3 protein. The polypeptide can be, e.g., a monomer, a homomultimer or a heteromer. For example, the polypeptide can be a homomultimer or a heteromer that includes more than one polypeptide, e.g., as shown by SEQ ID NO. 1, SEQ ID NO.4, and/or SEQ ID NO.7 (hT1R1, hT1R2 and hT1R3, respectively), or a conservative variation thereof. Also provided by the invention are isolated polypeptides that include one or more domains of an hT1R1, hT1R2, or hT1R3 polypeptide.

In addition to the polypeptides noted above, methods for producing a recombinant or isolated polypeptide are also provided. For example, the methods can include growing a cell in culture comprising an expression vector encoding a recombinant or isolated polypeptide as described above, under conditions suitable for expression of the isolated or recombinant polypeptide. The polypeptide is then purified, e.g., such that the polypeptide is enriched at least 5× (and typically 50×, 100×, 1000× or more) as compared to the polypeptide present in the culture. The resulting isolated or recombinant polypeptide made by this method is also a feature of the invention.

Nucleic acids, e.g., isolated or recombinant nucleic acids, are also a feature of the invention. For example, a nucleic acid that encodes any of the preceding polypeptides (e.g., SEQ ID NO. 1, SEQ ID NO. 4, and SEQ ID NO. 7, or a conservative variation thereof) is optionally a feature of the invention. In one class of embodiments, the nucleic acid encodes a substantially full-length a polypeptide, and/or is capable of rescuing a function of a mutant or recombinant cell that is defective with respect to hT1R1, hT1R2 or hT1R3 (e.g., where the cell is a deletion mutant with respect to hT1R1, hT1R2 and/or hT1R3). Exemplar nucleic acids of the invention include those represented at SEQ ID NO. 10, SEQ ID NO. 11, SEQ ID NO. 12, (hT1R1, hT1R2 and hT1R3 nucleic acids, respectively) and/or complementary sequences thereof. The nucleic acid optionally includes a DNA (e.g., a gDNA, a cDNA or a DNA cloning or expression vector), or an RNA (e.g., an mRNA or RNA cloning or expression vector).

In one related aspect, the invention includes an hT1R2 nucleic acid that hybridizes under stringent conditions to a first nucleic acid, e.g., that includes the first two exons (e.g., nucleotides 1-483) from nucleotide sequence of SEQ ID NO. 11, or to a complement thereof, wherein the stringent conditions are selected such that the hT1R2 nucleic acid preferentially hybridizes to the first nucleic acid as compared to a mT1R2 nucleic acid or complement thereof, or to an rT1R2 nucleic acid or complement thereof. For example, the hT1R2 nucleic acid can encode a hT1R2 polypeptide comprising the sequence set forth at SEQ ID NO: 4. Here again, the nucleic acid optionally encodes a substantially full length hT1R2 polypeptide and can be a DNA or RNA (e.g., a gDNA, a cDNA or a DNA cloning or expression vector), or an RNA (e.g., an mRNA or RNA cloning or expression vector). For example, the hT1R2 nucleic acid can include or be coded within an expression vector.

The present invention also provides antibodies, e.g., antibodies or fragments thereof which specifically bind the isolated or recombinant polypeptides described above. For example, the antibody fragment can be an Fab or F(ab')2 fragment, the antibody can be a monoclonal or polyclonal antibody, or the like. Optionally, the antibody can be a discriminatory antibody that specifically hybridizes to a polypeptide as noted above, but which does not specifically bind to a rat or mouse homologue protein, e.g., mT1R1, mT1R2, mT1R3, rT1R1, rT1R2 or rT1R3.

As noted above, in one aspect, expression vectors that encode the polypeptides noted above are provided. Similarly, cells that include the expression vectors are a feature of the invention. In addition, biosensors comprising the polypeptides are also a feature of the invention.

In one aspect, the invention includes a database and/or a computer-readable medium comprising a character string that represents any polypeptide, nucleic acid, cell, vector, antibody or other material of the invention that is noted herein. Optionally, the database or computer readable medium is coupled to one or more instruction set, software package, network, internet, intranet, user input, user-viewable output, computer, or other feature or component that transmits, manipulates, reads or otherwise acts upon the database or computer-readable medium.

The invention also provides methods of identifying compounds which bind to and/or modulate an activity of the isolated or recombinant polypeptides noted above. In the methods, a biological sample comprising the isolated or recombinant polypeptide is contacted with a test compound binding and/or modulation of the activity of the polypeptide by the compound is then detected, thereby identifying a compound which binds to and/or modulates the activity of the polypeptide. The detection of binding or activity can take any of a wide variety of forms, e.g., detecting binding of an antibody to the isolated or recombinant polypeptide, or detecting a signal produced by the isolated or recombinant polypeptide. In addition to detection of activity of the polypeptides noted above, cells or other biological materials that include endogenous hT1R1, hT1R2 or hT1R3 can be used in the methods (e.g., cultures of cells derived from taste buds, or the like). Optionally, such materials and methods do not include testing cells in a mammal, e.g., in a human.

Examples of signals that can be detected include conformation-dependent signals, e.g., where a conformation of the isolated or recombinant polypeptide is modified by binding of the test compound to the isolated or recombinant polypeptide. Detecting binding can include, e.g., one or more of: a $Ca^{2+}$ flux assay, a cAMP assay, a GTPgammaS binding assay, a melanophore assay, a phospholipase C assay, a beta-arrestin FRET assay, and a transcriptional reporter assay. Where detection includes measuring a signal from a transcriptional reporter assay (e.g., detection of a reporter gene (e.g., CAT activity) coupled to a response element that is controlled by a second messenger activated by hT1R1, hT1R2 and/or hT1R3, or a multimer thereof), common response elements that can be detected include: a CRE, a SRE, an MRE, a TRE, an NFAT, and/or an NFkB-response element.

The biological sample can be in any of a variety of configurations, e.g., cells which express the recombinant polypeptide, biosensors (liquid or solid phase), a ChemFET, a cell extract; a membrane preparation comprising the protein of interest or another material comprising the proteins noted herein, or the like.

The invention also provides methods of rescuing cells that have altered or missing T1R1, T1R2, or T1R3 function (e.g., due to deletion or other mutation of genes relevant to such function). In the methods, a nucleic acid that encodes the recombinant polypeptide noted above is introduced into a cell and expressed, thereby providing hT1R1, hT1R2, or hT1R3 function to the cell. The cell can, e.g., be in cell culture, in a tissue, in a taste bud, in a mammal (e.g., a human), or the like.

The invention also includes kits, e.g., comprising a polypeptide, nucleic acid, vector, cell or antibody as noted above and further including, e.g., instructional materials in the use of the polypeptides or nucleic acids, e.g., in the methods herein, packaging materials, containers for holding other kit elements, and the like.

BRIEF DESCRIPTION OF THE FIGURES

FIG. 1A-G is a sequence alignment between human, mouse and rat sweet receptor sequences. Three putative human sweet receptor proteins (hT1R1, SEQ ID NO:1; hT1R2, SEQ ID NO:4; and hT1R3, SEQ ID NO:7) are aligned with three mouse T1Rs (mT1R1, SEQ ID NO:2; mT1R2, SEQ ID NO:5; and mT1R3, SEQ ID NO:8), and two rat T1Rs (rT1R1, SEQ ID NO:3; and rT1R2 SEQ ID NO:6) using ClustalW. Horizontal bars indicate seven-transmembrane domains for GPCRs as predicted using hT1R1 protein; potential signal peptides for hT1R1-3 are boxed. Identical amino acids are boxed in black, while conserved amino acids are boxed in gray. As shown, the three human sweet receptors are related to mouse and rat T1Rs.

FIGS. 2A-2C provide nucleotide sequences of hT1R1 (SEQ ID NO:10), hT1R2 (SEQ ID NO:11) and hT1R3 (SEQ ID NO:12) cDNAs. FIG. 2A shows the nucleotide sequence of the hT1R1 cDNA (SEQ ID NO:10). FIG. 2B shows the nucleotide sequence of the hT1R2 cDNA (SEQ ID NO:11). FIG. 2C shows the nucleotide sequence of the hT1R3 cDNA (SEQ ID NO:12).

DETAILED DESCRIPTION

Definitions

Figure 3:
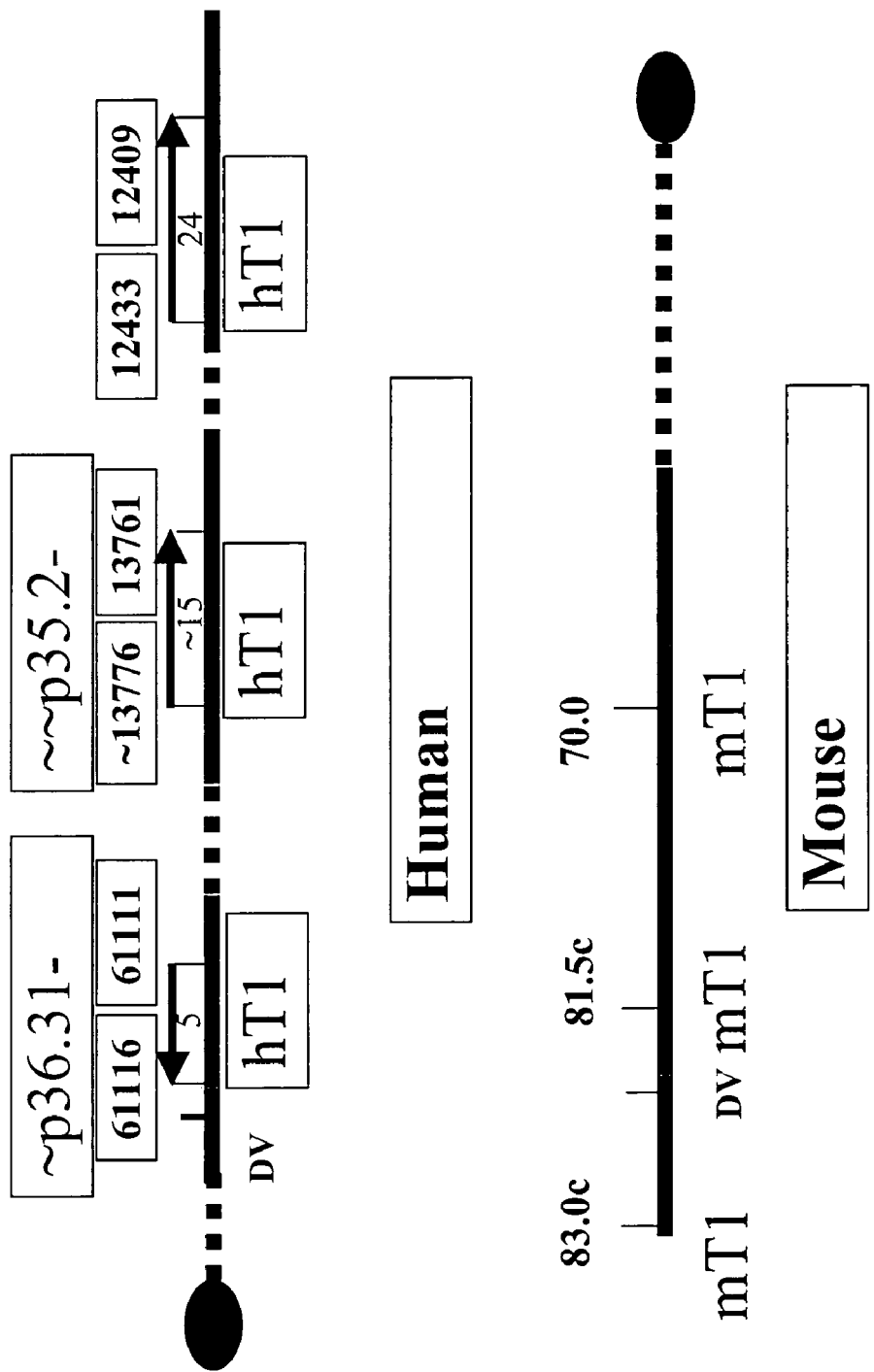
FIG. 3 is a schematic showing the structure/location of the three sweet receptor genes (clustered in human chromosome 1). (Top) Chromosome mapping studies were carried out using the NCBI human genome search interface with the distance to the end of the chromosome shown in kilobases (K) (not to scale). The chromosome locations of two genes (T1R2 and T1R3) were determined using two BAC clones (AL080251 and AL391244, respectively) that are located very close to the two genes. The arrow indicates the span and orientation of the gene. The numbers under the arrows indicate the size of the gene, including introns and exons. The number for T1R2 is approximate because the sequence for the transcriptional start region and first two exons is not available. (Bottom) The distal region of mouse chromosome 4 corresponds to the syntenic region of human 1p36.33. The locations of three mouse T1Rs were obtained from The Jackson Laboratory Mouse Informatics Database.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

A "vector" is a composition for facilitating introduction, replication and/or expression of a selected nucleic acid in a cell. Vectors include, e.g., plasmids, cosmids, viruses, YACs, bacteria, poly-lysine, etc. A "vector nucleic acid" is a nucleic acid molecule into which heterologous nucleic acid is optionally inserted which can then be introduced into an appropriate host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes." "Expression vectors" are vectors that comprise elements that provide for or facilitate transcription of nucleic acids which are cloned into the vectors. Such elements can include, e.g., promoters and/or enhancers operably coupled to a nucleic acid of interest.

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "isolated" means that the material is removed from its original environment (e.g., the natural environment if it is naturally occurring). For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment. A "recombinant nucleic acid" is one that is made by recombining nucleic acids, e.g., during cloning, DNA shuffling or other procedures. A "recombinant polypeptide" is a polypeptide which is produced by expression of a recombinant nucleic acid. An "amino acid sequence" is a polymer of amino acid residues (a protein, polypeptide, etc.) or a character string representing an amino acid polymer, depending on context. Either the given nucleic acid or the complementary nucleic acid can be determined from any specified polynucleotide sequence.

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. A "polynucleotide sequence" is a nucleic acid (which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

A "subsequence" or "fragment" is any portion of an entire sequence, up to and including the complete sequence. Typically a subsequence or fragment comprises less than the full-length sequence.

Numbering of a given amino acid or nucleotide polymer "corresponds to numbering" of a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring hT1Rx nucleic acid can be modified by any available mutagenesis method. When expressed, this mutagenized nucleic acid encodes a polypeptide that is homologous to the protein encoded by the original hT1Rx nucleic acid. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

The terms "identical", "sequence identical" or "sequence identity" in the context of two nucleic acid sequences or amino acid sequences refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) *Adv. Appl. Math.* 2:482; by the alignment algorithm of Needleman and Wunsch (1970) *J. Mol. Biol.* 48:443; by the search for similarity method of Pearson and Lipman (1988) *Proc. Nat. Acad. Sci U.S.A.* 85:2444; by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp (1988) *Gene* 73:237-244 and Higgins and Sharp (1989) *CABIOS* 5:151-153; Corpet et al. (1988) *Nucleic Acids Res.* 16:10881-10890; Huang et al (1992) *Computer Applications in the Biosciences* 8:155-165; and Pearson et al. (1994) *Methods in Molecular Biology* 24:307-331. Alignment is also often performed by inspection and manual alignment. In one class of embodiments, the polypeptides herein are at least 70%, generally at least 75%, optionally at least 80%, 85%, 90%, 95% or 99% or more identical to a reference polypeptide, e.g., hT1R1, hT1R2 and/or hT1R3, e.g., as set forth at SEQ ID NO: 1, SEQ ID NO: 4 or SEQ ID NO: 7 respectively, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 99% or more identical to a reference nucleic acid, e.g., hT1R1, hT1R2 and/or hT1R3, e.g., as set forth at SEQ ID NO: 10, SEQ ID NO: 11 or SEQ ID NO: 12, respectively, e.g., as measured by BLASTN (or CLUSTAL, or any other available alignment software) using default parameters.

The terms "substantially identical" nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

"Selectively hybridizing" or "selective hybridization" includes hybridization, under stringent hybridization conditions, of a nucleic acid sequence to a specified nucleic acid target sequence to a detectably greater degree that its hybridization to non-target nucleic acid sequences. Selectively hybridizing sequences have at least 50%, or 60% or 70% or 80% or 90% sequence identity or more, e.g., preferably 95% sequence identity, and most preferably 98-100% sequence identity (i.e., complementarity) with each other.

"Stringent hybridization" conditions or "stringent conditions" in the context of nucleic acid hybridization assay formats are sequence dependent, and are different under different environmental parameters. An extensive guide to hybridization of nucleic acids is found in Tijssen (1993) *Laboratory Techniques in Biochemistry and Molecular Biology—Hybridization with Nucleic Acid Probes* Part 1, Chapter 2 "Overview of Principles of Hybridization and the Strategy of Nucleic Acid Probe Assays" Elsevier, New York. Generally, highly stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular nucleic acid of the present invention, this occurs, e.g., when a copy of a nucleic acid is created using the maximum codon degeneracy permitted by the genetic code. Stringent hybridization conditions are sequence-dependent and will be different in different circumstances. Longer sequences hybridize specifically at higher temperatures.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher, e.g., 5×, 10×, 20×, 50×, 100× or more) than that observed for control probe in the particular hybridization assay indicates detection of a specific hybridization. For example, the control probe can be a mouse or rate homologue to the relevant nucleic acid, as noted herein. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "polypeptide" is used interchangeably herein with the terms "polypeptides" and "protein(s)", and refers to a polymer of amino acid residues, e.g., as typically found in proteins in nature. A "mature protein" is a protein which is full-length and which, optionally, includes glycosylation or other modifications typical for the protein in a given cell membrane.

The term "modulate" with respect to an hT1R1, hT1R2, and/or hT1R3 proteins refers to a change in the activity of hT1R1, hT1R2, and/or hT1R3 proteins. For example, modulation may cause an increase or a decrease in protein activity (e.g., coupled GTPase activity), binding characteristics, membrane permeability or any other biological, functional, or immunological properties of such proteins. The change in activity can arise from, for example, an increase or decrease in expression of one or more genes that encode these proteins, the stability of an mRNA that encodes the protein, translation efficiency, or from a change in activity of the protein itself. For example, a molecule that binds to one of the receptors can cause an increase or decrease in the biological activity of the receptor.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described below.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, *Fundamental Immunology*, W. E. Paul, ed., Raven Press, N.Y. (1999), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include multiple or single chain antibodies, including single chain Fv (sFv) antibodies in which a variable heavy and a variable light chain are joined together (directly or through a peptide linker) to form a continuous polypeptide.

A variety of additional terms are defined or otherwise characterized herein.

Description of the Preferred Embodiments

The present invention relates to the identification of three novel members of human sweet receptors referred to as hT1R1, hT1R2 and hT1R3 nucleic acids encoding these proteins, vectors and host cells comprising the nucleic acids, methods for producing the proteins and methods for identifying compounds which bind to and/or modulate the activity of these proteins. These genes are specifically expressed in specialized neuroepithelial cells referred to as human taste receptor cells located in the fungiform papillae of the tongue.

Evidence supports the assignment of hT1R1, hT1R2 and hT1R3 as belonging to the sweet receptor family. The hT1R1, hT1R2 and hT1R3 proteins show homology to their mouse (mT1R1, mT1R2, mT1R3) and rat (rT1R1, rT1R2) counterparts (see, Example 1). All three hT1Rs are predicted to contain seven-transmembrane domains (see, FIG. 1) consistent with previous studies implicating G proteins and their respective GPCRs in sweet taste transduction. In addition, all three ht1Rs are predicted to have long N-terminal extracellular domains which is characteristic of other members of the GPCR subfamily 3, which includes metabotropic glutamate receptors (as described below, the receptors herein can form heteromers that provide glutamate receptor activity as well as sweet receptor activity), extracellular $Ca^{++}$ sensors and pheromone receptors. Chromosome mapping studies using the NCBI human genome search interface (see, Example 2) have demonstrated that these three genes are clustered in a region of human chromosome 1. The aforementioned region of the human chromosome is syntenous to the distal end of mouse chromosome 4 which contains the Sac locus, which in turn has been implicated in detecting sweet tastants as described, e.g., in Fuller, *J. Hered*. 65:33-36, 1974; Lush et al., *Genet. Res*. 66:167-174; and Bachmanov, *Mamm. Genome* 8:545-548. In situ hybridization studies (see, Example 3) have also confirmed that these genes are specifically expressed in human taste receptor cells in the fungiform papillae of the human tongue which is consistent with their role in taste perception. Based on the amino acid homology between the hT1R proteins and their mouse and rat counterparts, the hT1R genes' expression in the fungiform papillae of the human tongue, and the location of the hT1R proteins on human chromosome 1, a syntenic region of the distal end of mouse chromosome 4 in which the mouse Sac locus maps, it is reasonable to conclude that the new hT1R proteins function as sweet receptors or receptor components. As noted below, various heteromeric versions of the proteins have been shown to respond to glutamate, implicating them as glutamate receptors as well.

Since the aforementioned genes are expressed in taste cells, these genes and their related polypeptides can serve as specific targets for the identification of sweet tastants and the design of novel sweeteners. Accordingly, the invention also relates to methods for screening compounds that bind to and/or modulate the activity of these receptors, to identify compounds that stimulate sweet taste perception.

Making Compositions of the Invention

In practicing the present invention, many conventional techniques in molecular biology, microbiology, and recombinant DNA are optionally used. These techniques are well known and are explained in, for example, *Current Protocols in Molecular Biology*, Volumes I, II, and III, 1997 (F. M. Ausubel ed.); Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively).

Nucleic Acids

In one aspect, the invention provides isolated nucleic acids encoding a hT1R1 protein. These include the isolated nucleic acid molecule encoding hT1R1 protein comprising an amino acid sequence as set forth in SEQ ID NO:1 (FIG. 1) and the isolated nucleic acid molecule encoding a hT1R1 protein comprising a nucleotide sequence as set forth in SEQ ID NO:10 (FIG. 2A) as well as a wide variety of variants as noted herein.

In another aspect, the invention provides isolated nucleic acids encoding a hT1R2 protein. These include the isolated nucleic acid molecule encoding hT1R2 protein comprising an amino acid sequence as set forth in SEQ ID NO:4 (FIG. 1) and the isolated nucleic acid molecule encoding a hT1R2 protein comprising a nucleotide sequence as set forth in SEQ ID NO:11 (FIG. 2B) as well as a wide variety of variants as noted herein.

In another aspect, the invention provides isolated nucleic acids encoding a hT1R3 protein. These include the isolated nucleic acid molecule encoding hT1R3 protein comprising an amino acid sequence as set forth in SEQ ID NO:7 (FIG. 1) and the isolated nucleic acid molecule encoding a hT1R3 protein comprising a nucleotide sequence as set forth in SEQ ID NO:12 (FIG. 2C) as well as a wide variety of variants as noted herein.

Nucleic acid molecules of the present invention also include isolated nucleic acid molecules that have at least 50% identity or more, typically at least 60% identity or more, generally 70% identity or more, often 80% identity or more, e.g., 90% identity or more, preferably at least 95% identity, more-preferably at least 98% identity, and most preferably at least 99% identity to a nucleic acid encoding a polypeptide comprising the amino acid sequence of SEQ ID NO:1, SEQ ID NO:4 and/or SEQ ID NO:7, respectively. Such nucleic acid molecules include a nucleic acid encoding a polypeptide of SEQ ID NO:1, SEQ ID NO:4 and SEQ ID NO:7 as set forth above. The identity can be over the entire coding region, or can be over a subsequence, e.g., a subsequence comprising at least about 10%, e.g., at least 25%, e.g., at least 50% or more of the full-length sequence. Nucleic acids of the present invention also include fragments of the aforementioned nucleic acid molecules. For example, the invention provides nucleic acids that encode one or more of the domains of the hT1R receptors. Such domains include the amino terminal extracellular domain, the seven transmembrane (TM) domains, the extracellular domains (located between TM2 and TM3, between TM4 and TM5, and between TM6 and TM7), and the intracellular domains (C-terminal to TM7, and between TM1 and TM2, between TM3 and TM4, and between TM5 and TM6). The amino acid sequences of the transmembrane domains, intracellular domains, and extracellular domains are shown in, for example, FIG. 1.

Nucleic acids of the present invention include isolated nucleic acid molecules encoding polypeptide variants which comprise the amino acid sequences of SEQ ID NO:1, SEQ ID NO:4 and SEQ ID NO:7 (h1R1, h1R2 and h1R3, respectively). Such nucleotide variants include deletion variants, substitution variants and addition or insertion variants.

The invention also provides isolated nucleic acid molecules that are fully complementary to all the above described isolated nucleic acid molecules.

An isolated nucleic acid encoding one of the above polypeptides including homologs from species other than rat, mouse or human, may be obtained by a method which comprises the steps of screening an appropriate library under stringent conditions with a labeled probe having the sequence of SEQ ID NO:2, SEQ ID NO:4 and SEQ ID NO:6, or a fragment thereof; and isolating cDNA and genomic clones containing the nucleotide sequences. Such hybridization techniques are well-known to a skilled artisan. Another typical method for making appropriate sequences includes performing PCR on genomic or cDNA from an appropriate library or nucleic acid preparation.

Nucleic acid molecules encoding the above hT1R receptors and variants thereof can be obtained from genomic or cDNA, can be amplified via PCR or LCR, or can be synthesized, or made by any combination of conventional techniques. The DNA can then be used to express the hT1R protein, or as a template for preparation of RNA or as a molecular probe which selectively hybridizes to, and thus can detect the presence of, other T1Rx-encoding nucleotide sequences. Naturally occurring sequences can be mutated, e.g., by point mutagenesis or DNA shuffling or other available mutagenesis methods to make variants that are within the scope of the invention. One of skill will also appreciate that essentially any RNA can be converted into a double stranded DNA suitable for restriction digestion, PCR expansion and sequencing using reverse transcriptase and a polymerase. See, Ausubel, Sambrook and Berger, herein. In addition, RNAs of the invention can be made by transcription of DNA sequences.

When nucleic acid molecules of the present invention are utilized for the recombinant production of hT1R polypeptides of the present invention, the nucleotide sequence can include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded, e.g., a hexa-histidine peptide, as provided in the pQE vector (Qiagen, Inc.) and described in Gentz et al., *Proc. Nat'l. Acad. Sci. USA* (1989) 86:821-824, or is an HA tag. The nucleic acid molecule can also contain noncoding 5' and 3' sequences, such as transcribed, non-translated sequences, splicing and polyadenylation signals, ribosome binding sites and sequences that stabilize mRNA.

General texts which describe molecular biological techniques for making nucleic acids, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564.

In addition, a plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms, or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (above). A catalogue of Bacteria and Bacteriophages useful for cloning is provided, e.g., by the ATCC, e.g., *The ATCC Catalogue of Bacteria and Bacteriophage* published yearly by the ATCC. Additional basic procedures for sequencing, cloning and other aspects of molecular biology and underlying theoretical considerations are also found in Watson et al. (1992) *Recombinant DNA Second Edition, Scientific American Books*, NY.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

In addition, essentially any nucleic acid (and virtually any labeled nucleic acid, whether standard or non-standard) can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others.

Various types of mutagenesis are optionally used in the present invention, e.g., to modify hT1R1, hT1R2 or hT1R3 nucleic acids and encoded polypeptides to produce conservative or non-conservative variants. Any available mutagenesis procedure can be used. Such mutagenesis procedures optionally include selection of mutant nucleic acids and polypeptides for one or more activity of interest. Procedures that can be used include, but are not limited to: site-directed point mutatgenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, and many others known to persons of skill. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like. In another class of embodiments, modification is essentially random (e.g., as in classical DNA shuffling).

The above texts describe these procedures. Additional information is found in the following publications and references cited within: Arnold, *Protein engineering for unusual environments, Current Opinion in Biotechnology* 4:450-455 (1993); Bass et al., *Mutant Trp repressors with new DNA-binding specificities, Science* 242:240-245 (1988); Botstein & Shortle, *Strategies and applications of in vitro mutagenesis, Science* 229:1193-1201(1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA* procedure without enzymatic reactions in vitro, *Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Kunkel, *The efficiency of oligonucleotide directed mutagenesis,* in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA,* 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide,* (1988) *Nucl. Acids Res.* 16: 803-814; Sieber, et al., *Nature Biotechnology,* 19:456-460 (2001); Smith, *In vitro mutagenesis, Ann. Rev. Genet.* 19:423-462 (1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond.* A 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); and Zoller & Smith, *Oligonucleotide-directed mutagenesis: a simple method using two oligonucleotide primers and a single-stranded DNA template, Methods in Enzymol.* 154: 329-350 (1987). Additional details on many of the above methods can be found in *Methods in Enzymology* Volume 154, which also describes useful controls for trouble-shooting problems with various mutagenesis methods.

Polypeptides

In another aspect, the present invention relates to hT1R polypeptides. These include the hT1R1 polypeptide comprising an amino acid sequence as set forth in SEQ ID NO:1 (FIG. 1), the hT1R2 polypeptide comprising an amino acid sequence as set forth in SEQ ID:4 (FIG. 1) and the hT1R3 polypeptide comprising an amino acid sequence as set forth in SEQ ID NO:7 (FIG. 1) as well as variants thereof. The polypeptides of the present invention also include fragments of the aforementioned sequences. For example, the invention also provides polypeptides that comprise one or more domains of the hT1R receptor polypeptides. These domains, which include extracellular domains, intracellular domains, and transmembrane domains, are described above and shown in FIG. 1.

Polypeptides of the present invention include isolated polypeptides, e.g., variants, in which the amino acid sequence has at least 75% identity, preferably at least 80% identity, typically 90% identity, preferably at least 95% identity, more preferably at least 98% identity and most preferably at least 99% identity, to the amino acid sequences as set forth in SEQ ID NO:1, SEQ ID NO:4 and SEQ ID NO:7. Such sequences include the sequences of SEQ ID NO:1, SEQ ID NO:4 and SEQ ID NO:7 as set forth above.

The aforementioned hT1R polypeptides can be obtained by any of a variety of methods. Smaller peptides (less than 50 amino acids long) are conveniently synthesized by standard chemical techniques and can be chemically or enzymatically ligated to form larger polypeptides. Polypeptides can be purified from biological sources by methods well known in the art (see, e.g., *Protein Purification, Principles and Practice, Second Edition* (1987) Scopes, Springer Verlag, N.Y.). They are optionally (and preferably) produced in their naturally occurring, truncated, or fusion protein forms by recombinant DNA technology using techniques well known in the art. These methods include, for example, in vitro recombinant DNA techniques, synthetic techniques and in vivo genetic recombination. See, for example, the techniques described in Sambrook et al. (2001) *Molecular Cloning, A Laboratory Manual,* Third Edition, Cold Spring Harbor Press, N.Y.; and Ausubel et al., eds. (1997) *Current Protocols in Molecular Biology,* Green Publishing Associates, Inc., and John Wiley & Sons, Inc., N.Y (supplemented through 2002). Alternatively, RNA encoding the proteins can be chemically synthesized. See, for example, the techniques described in *Oligonucleotide Synthesis,* (1984) Gait ed., IRL Press, Oxford, which is incorporated by reference herein in its entirety. Obtaining large quantities of these polypeptides is preferably by recombinant techniques as further described above under the section entitled "making nucleic acids."

Another aspect of the present invention relates to a method for producing a hT1R1, ht1R2 or hT1R3 polypeptide, or a polypeptide that comprises one or more domains thereof. These methods involve, e.g.,:

a) culturing a host cell comprising a nucleic acid of the invention, e.g., a nucleic acid encoding an hT1R1, hT1R2 or hT1R3 polypeptide, or variant or domain thereof, under conditions suitable for expression of the hT1R1, hT1R2 or hT1R3 polypeptide; and b) isolating the hT1R1, hT1R2 or hT1R3 polypeptide or domain thereof.

As described, the nucleic acid molecules described herein can be expressed in a suitable host cell to produce active hT1R1, hT1R2 or hT1R3 protein. Expression occurs by placing a nucleotide sequence encoding these proteins into an appropriate expression vector and introducing the expression vector into a suitable host cell, culturing the transformed host cell under conditions suitable for expression of the hT1R1, hT1R2, hT1R3 protein or variant thereof, or a polypeptide that comprises one or more domains of such proteins, and purifying the recombinant proteins from the host cell to obtain purified, and preferably active, hT1R1, hT1R2 or hT1R3 protein. Appropriate expression vectors are known in the art. For example, pET-14b, pCDNA1Amp, and pVL1392 are available from Novagen and Invitrogen and are suitable vectors for expression in E. coli, COS cells and baculovirus infected insect cells, respectively. These vectors are illustrative of those that are known in the art. Suitable host cells can be any cell capable of growth in a suitable media and allowing purification of the expressed protein. Examples of suitable host cells include bacterial cells, such as E. coli, Streptococci, Staphylococci, Streptomyces and Bacillus subtilis cells; fungal cells such as yeast cells, e.g., Pichia, and Aspergillus cells; insect cells such as Drosophila S2 and Spodoptera Sf9 cells, mammalian cells such as CHO, COS, HeLa; and plant cells.

Culturing and growth of the transformed host cells can occur under conditions that are known in the art. The conditions will generally depend upon the host cell and the type of vector used. Suitable culturing conditions may be used such as temperature and chemicals and will depend on the type of promoter utilized. In addition to Sambrook, Berger, Ausubel and the other references previously noted, details regarding cell culture can also be found in Freshney (1994) Culture of Animal Cells, a Manual of Basic Technique, third edition, Wiley-Liss, New York Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); and Atlas and Parks (eds) The Handbook of Microbiological Media (1993) CRC Press, Boca Raton, Fla.

Purification of the hT1R1, hT1R2 or hT1R3 protein, or domains of such proteins, can be accomplished using known techniques without performing undue experimentation. Generally, the transformed cells expressing one of these proteins are broken, crude purification occurs to remove debris and some contaminating proteins, followed by chromatography to further purify the protein to the desired level of purity. Cells can be broken by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during intracellular synthesis, isolation or purification.

In general, proteins of the invention, e.g., proteins comprising hT1R1, hT1R2 and/or hT1R3 sequences or domains, or antibodies to such proteins can be purified, either partially (e.g., achieving a 5×, 10×, 100×, 500×, or 1000× or greater purification), or even substantially to homogeneity (e.g., where the protein is the main component of a solution, typically excluding the solvent (e.g., water or DMSO) and buffer components (e.g., salts and stabilizers) that the protein is suspended in, e.g., if the protein is in a liquid phase), according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against hT1R1, hT1R2 and/or hT1R3 (or proteins comprising hT1R1, hT1R2 and/or hT1R3 domains) are used as purification reagents, e.g., for affinity-based purification of proteins comprising one or more hT1R1, hT1R2 and/or hT1R3 domains or antibodies thereto. Once purified, partially or to homogeneity, as desired, the polypeptides are optionally used e.g., as assay components, therapeutic reagents or as immunogens for antibody production.

In addition to other references noted herein, a variety of purification/protein purification methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ; Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein.

Those of skill in the art will recognize that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from E. coli, the expressed protein is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

The polynucleotides of the present invention optionally comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the sequence of the invention is useful to facilitate purification.

Sequence Variations

Silent Variations

Due to the degeneracy of the genetic code, any of a variety of nucleic acids sequences encoding polypeptides of the invention are optionally produced, some which can bear lower levels of sequence identity to the hT1Rx nucleic acid and polypeptide sequences in the figures. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

As an example, the nucleic acid sequence corresponding to nucleotides 1-18 of SEQ ID NO: 10 is: ATG CTG CTC TGC ACG GCT (MLLCTA, amino acids 1-6 from SEQ ID NO: 1). A silent variation of this sequence includes ATG TTA TTG TGT ACC GCC (SEQ ID NO:19, also encoding MLLCTA from SEQ ID NO:1).

Such "silent variations" are one species of "conservatively modified variations", discussed below. One of skill will recognize that each codon in a nucleic acid (except ATG, which is ordinarily the only codon for methionine) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a T1Rx polypeptide of the invention. All such variations of every nucleic acid herein are specifically provided and described by consideration of the sequence in combination with the genetic code. One of skill is fully able to make these silent substitutions using the methods herein.

Conservative Variations

"Conservatively modified variations" or, simply, "conservative variations" of a particular nucleic acid sequence or polypeptide are those which encode identical or essentially identical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another.

TABLE 2

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

For example, a conservatively substituted variation of the polypeptide identified herein as SEQ ID NO:1 will contain "conservative substitutions", according to the six groups defined above, in up to about 40 residues (i.e., about 5% of the amino acids) in the full-length polypeptide.

In a further example, if conservative substitutions were localized in the region corresponding to amino acids 5-10 (TARLV), examples of conservatively substituted variations of this region include conservative exchange of conserved amino acids, e.g., substitution of STKMM (SEQ ID NO:20) or TSKVI (SEQ ID NO:21) (or any others that can be made according to Table 2) for TARLV. Listing of a protein sequence herein, in conjunction with the above substitution table, provides an express listing of all conservatively substituted proteins.

Finally, the addition or deletion of sequences which do not alter the encoded activity of a nucleic acid molecule, such as the addition or deletion of a non-functional sequence, is a conservative variation of the basic nucleic acid or polypeptide.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

hT1R1, hT1R2 and/or hT1R3 Antibodies

In another aspect, antibodies to hT1R1, hT1R2 or hT1R3 proteins or fragments thereof can be generated using methods that are well known in the art. The antibodies can be utilized for detecting and/or purifying the hT1Rx proteins, optionally discriminating the proteins from various homologues, and/or in biosensor hT1R1, hT1R2 or hT1R3 activity detection applications. As used herein, the term antibody includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a protein encoded by one of the disclosed genes, various host animals may be immunized by injection with the polypeptide, or a portion thereof. Such host animals may include, but are not limited to, rabbits, mice and rats, to name but a few. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Nat'l. Acad. Sci. USA* 81:6851-6855, 1984; Neuberger et al., *Nature* 312:604-608, 1984; Takeda et al., *Nature* 314:452-454, 1985) by splicing the genes from a mouse antibody molecule of appropriate antigen specificity, together with genes from a human antibody molecule of appropriate biological activity, can be used. A chimeric antibody is a molecule in which different portions are derived from different animal species, such as those having a variable or hypervariable region derived from a murine mAb and a human immunoglobulin constant region.

Alternatively, techniques described for the production of single-chain antibodies (U.S. Pat. No. 4,946,778; Bird, *Science* 242:423-426, 1988; Huston et al., *Proc. Nat'l. Acad. Sci. USA* 85:5879-5883, 1988; and Ward et al., *Nature* 334:544-546, 1989) can be adapted to produce differentially expressed gene-single chain antibodies. Single chain antibodies are formed by linking the heavy and light chain fragments of the Fv region via an amino acid bridge, resulting in a single-chain polypeptide.

In one aspect, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments which recognize specific epitopes may be generated by known techniques. For example, such fragments include, but are not limited to, the F(ab')$_2$ fragments, which can be produced by pepsin digestion of the antibody molecule, and the Fab fragments, which can be generated by reducing the disulfide bridges of the F(ab')$_2$ fragments. Alternatively, Fab expression libraries may be constructed (Huse et al., *Science* 246:1275-1281, 1989) to allow rapid and easy identification of monoclonal Fab fragments with the desired specificity.

The protocols for detecting and measuring the expression of the described hT1R proteins using the above mentioned antibodies are well known in the art. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific and patent literature, and many employed commercially.

Particularly preferred, for ease of detection, is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule and incubated for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay, in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the protein expressed by the gene of interest.

The most commonly used reporter molecules in this type of assay are either enzymes, fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product, rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of PLAB which is present in the serum sample.

Alternately, fluorescent compounds, such as fluorescein and rhodamine, can be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Defining Proteins and Nucleic Acids by Immunoreactivity

Because the polypeptides of the invention provide a variety of new polypeptide sequences, the polypeptides also provide new structural features which can be recognized, e.g., in immunological assays. The generation of antisera which specifically bind the polypeptides of the invention, as well as the polypeptides which are bound by such antisera, are a feature of the invention.

For example, the invention includes hT1R1, hT1R2 and hT1R3 proteins that specifically bind to or that are specifically immunoreactive with an antibody or antisera generated against an immunogen comprising an amino acid sequence selected from SEQ ID NO: 1, SEQ ID NO: 4 or SEQ ID NO: 7 (and/or nucleic acids that encode such hT1R1, hT1R2 and hT1R3 proteins). To eliminate cross-reactivity with other homologues (e.g., the mouse and rat homologues), the antibody or antisera is optionally subtracted with mT1R1, mT1R2, mT1R3, rT1R1, rT1R2, and/or rT1R3 protein(s).

In one typical format, the immunoassay uses a polyclonal antiserum which was raised against one or more polypeptide comprising one or more of the sequences corresponding to one or more of SEQ ID NO: 1, SEQ ID NO: 4 or SEQ ID NO: 7 or a substantial subsequence thereof (i.e., at least about 30% of the full length sequence provided, or typically at least about 50%, 75% or more of the sequence). The set of potential polypeptide immunogens-derived from SEQ ID NO: 1, SEQ ID NO: 4 or SEQ ID NO: 7 are collectively referred to below as "the immunogenic polypeptides." The resulting antisera is optionally selected to have low cross-reactivity against the control homologues (mT1R1, mT1R2, mT1R3, rT1R1, rT1R2, and/or rT1R3, e.g., as set forth in SEQ ID NO: 2, SEQ ID NO: 3 SEQ ID NO: 5 SEQ ID NO: 6 SEQ ID NO: 8 and SEQ ID NO: 9) and any such cross-reactivity is optionally removed, e.g., by immunoabsorbtion, with one or more of the control homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional references and discussion of antibodies is also found herein and can be applied here to defining polypeptides by immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control polypeptides to produce subtracted pooled titered polyclonal antisera.

The subtracted pooled titered polyclonal antisera are tested for cross reactivity against the control homologues (the mouse and or rat T1Rx protein(s)) in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic polypeptide as compared to binding to the control homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control homologues under discriminatory binding conditions, and at least about a 1/2 signal to noise ratio as compared to the immunogenic polypeptide(s), clearly shares substantial structural similarity with the immunogenic polypeptide as compared to the mouse or rat homologues, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is optionally determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides as compared to the control polypeptides and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Methods of Use/Biosensors

In another aspect, the present invention relates to the use of the hT1R1, hT1R2 and hT1R3 proteins and/or coding nucleic acids in methods for identifying a compound, i.e., a sweet or umami (glutamate) tastant, that interacts/binds to the protein(s) encoded by these genes. The test compound can be natural or synthetic molecules such as proteins or fragments thereof, carbohydrates, organic or inorganic compounds and/or the like. This can be achieved, e.g., by utilizing the hT1R1, hT1R2 and hT1R3 proteins of the invention, or active fragments thereof, in cell-free or cell-based assays. A variety of formats are applicable, including measurement of second messenger effects (e.g., $Ca^{2+}$ flux assays, cAMP assays, GTPgammaS binding assays, melanophore assays; phospholipase C assays, beta-arrestin FRET assays, and transcriptional reporter assays, e.g., using CRE, SRE, MRE, TRE, NFAT, and/or NFkB-response elements coupled to appropriate reporters.

In one embodiment, cell-free assays for identifying such compounds comprise a reaction mixture containing a protein encoded by one of the disclosed genes and a test compound or a library of test compounds. Accordingly, one example of a cell-free method for identifying test compounds that specifically bind to the hT1R1, ht1R2 and hT1R3 proteins comprises contacting a protein or functional fragment thereof with a test compound or library of test compounds and detecting the formation of complexes by conventional methods. In particularly useful embodiments, a library of the test compounds can be synthesized on a solid substrate, e.g., plastic pins or some other surface. The test compounds are reacted with the hT1R protein or fragment thereof and washed to elute unbound protein. Bound hT1R is then detected by methods well known in the art. Purified hT1R can also be applied directly onto plates for use in the aforementioned screening method. Antibody binding to the proteins can also be detected in this format.

Interaction between molecules can also be assessed by using real-time BIA (Biomolecular Interaction Analysis, Pharmacia Biosensor AB), which detects surface plasmon resonance, an optical phenomenon. Detection depends on changes in the mass concentration of mass macromolecules at the biospecific interface and does not require labeling of the molecules. In one useful embodiment, a library of test compounds can be immobilized on a sensor surface, e.g., a wall of a micro-flow cell. A solution containing the protein or functional fragment thereof is then continuously circulated over the sensor surface. An alteration in the resonance angle, as indicated on a signal recording, indicates the occurrence of an interaction. This technique is described in more detail in the *BIAtechnology Handbook* by Pharmacia.

In yet other useful embodiments, the hT1R protein or fragment thereof can be immobilized to facilitate separation of complexes from uncomplexed forms of the protein and automation of the assay. Complexation of the protein can be achieved in any type of vessel, e.g., microtitre plates, micro-centrifuge tubes and test tubes. In particularly preferred embodiments, the protein can be fused to another protein, e.g., glutathione-S-transferase to form a fusion protein which can be adsorbed onto a matrix, e.g., glutathione Sepharose™ beads (Sigma Chemical. St. Louis, Mo.), which are then combined with the test compound and incubated under conditions sufficient to form complexes. Subsequently, the beads are washed to remove unbound label, and the matrix is immobilized and the radiolabel is determined.

Another method for immobilizing proteins on matrices involves utilizing biotin and streptavidin. For example, the protein can be biotinylated using biotin NHS (N-hydroxysuccinimide), using well known techniques and immobilized in the well of streptavidin-coated plates.

Cell-free assays can also be used to identify agents which specifically bind and/or modulate the activity. In one embodiment, the protein is incubated with a test compound and the catalytic activity of the protein is determined. In another embodiment, the binding affinity of the protein to a target molecule can be determined by methods known in the art.

In addition to cell-free assays such as those described above, the hT1R proteins can be utilized in cell-based assay for identifying compounds which bind to and/or modulate hT1R activity.

For example, one method for identifying compounds which bind to these proteins comprises, providing a cell that expresses one of these proteins, e.g., hT1R1, combining a test compound with the cell and measuring the formation of a complex between the test compound and the hT1R protein. The cell can be a mammalian cell, a yeast cell, bacterial cell, insect cell, a human taste cell of the fungiform papillae, or any other cell expressing the hT1R protein.

In another embodiment, human taste cells or heterologous cells expressing hT1Rs, or plasma membrane preparations of such cells, can be utilized to screen for bioactivity of test compounds or peptides. As stated above, the hT1R proteins described herein are homologous to known GPCR proteins. Accordingly, the hT1R proteins are coupled to G-proteins, which mediate signal transduction. A variety of intracellular effectors have been identified as being G-protein regulated including, but not limited to, adenyl cyclase, cyclic GMP, phospholipase C, phospholipase A2 and phosphodiesterases. G-proteins also interact with a variety of ion channels, e.g., certain voltage-sensitive $Ca^{++}$ transients. Accordingly, the level of such second messengers produced by the aforementioned intracellular effectors, and thus activity of the hT1R receptors, can be measured by techniques, which are well known to those skilled in the art. For example, the level of cAMP produced by activation of adenyl cyclase, can be measured by competitive assays which quantities $\{^3H\}$cAMP in the presence of unlabeled cAMP. The GTPase activity by G proteins can be measured, e.g., in plasma membrane preparations by measuring the hydrolysis of gamma $^{32}P$ GTP. Breakdown of phosphatidylinositol-4,5-bisphosphate to 1,4,5-IP3 and diacylglycerol can be monitored by measuring the amount of diacylglycerol using thin-layer chromatography, or measuring the amount of IP3 using radiolabeling techniques or HPLC. The generation of arachidonic acid by the activation of phospholipase A2 can be readily quantitated by well-known techniques.

The search for sweet (or glutamate) substances using hT1Rx genes can also be done by cell-based assay. It is known that GPCRs induce $Ca^{++}$ flux and other signal transduction pathways. Efflux of intracellular calcium or influx of calcium from outside the cell can be measured using conventional techniques, e.g., loading cells with a $Ca^{++}$ sensitive fluorescent dye such as fura-2 or indol-1, and measuring any change in $Ca^{++}$ using a fluorometer, such as Fluoskan Ascent Fluorescent Plate Reader or Flurometric Imaging Plate Reader. The signal pathways initiated by hT1Rs in response to sweet compounds can also be monitored by reporter gene assays. The co-localization of hT1R2 and hT1R3 in the same taste cell of human tongue may indicate the co-expression of hT1R2 and hT1R3 genes in the heterologous cell system is required for their activities. The co-expression of promiscuous G proteins with hT1Rs may help to funnel heterologous signal transduction of hT1Rs through a common pathway involving phospholipase C and $Ca^{++}$ mobilization.

As described, other assays such as melanophore assays, Phospholipase C assays, beta-arrestin FRET assays, and Transcriptional reporter assays, e.g., using CRE, SRE, MRE, TRE, NFAT, and/or NFkB-response elements coupled to appropriate reporters can be used. Detection using reporter genes coupled to appropriate response elements are particularly convenient. For example, the coding sequence to chloramphenicol acetyl transferase, beta galactosidase or other convenient markers are coupled to a response element that is activated by a second messenger that is activated by a protein of the invention. Cells expressing the marker in response to application of an appropriate test compound are detected by cell survival, or by expression of a colorimetric marker, or the like, according to well established methods.

In an alternate embodiment, conformational changes are detected by coupling the polypeptides of the invention to an electrical readout, e.g., to a chemically coupled field effect transistor (a CHEM-FET) or other appropriate system for detecting changes in conductance or other electrical properties brought about by a conformational shift by the protein of the invention.

In an alternate aspect, potential modulators of hT1R1, hT1R2 and/or hT1R3 activity or expression can be screened for. For example, potential modulators (small molecules, organic molecules, inorganic molecules, proteins, hormones, transcription factors, or the like) can be contacted to a cell and an effect on hT1R1, hT1R2 and/or hT1R3 activity or expression (or both) can be screened for. For example, expression of hT1R1, hT1R2 and/or hT1R3 can be detected, e.g., via northern analysis or quantitative (optionally real time) RT-PCR, before and after application of potential expression modulators. Similarly, promoter regions of the various genes (e.g., generally sequences in the region of the start site of transcription, e.g., within 5 KB of the start site, e.g., 1 KB, or less e.g., within 500 BP or 250 BP or 100 BP of the start site) can be coupled to reporter constructs (CAT, beta-galactosidase, luciferase or any other available reporter) and can be similarly be tested for expression activity modulation by the potential modulator. In either case, the assays can be performed in a high-throughput fashion, e.g., using automated fluid handling and/or detection systems, in serial or parallel fashion. Similarly, activity modulators can be tested by contacting a potential modulator to an appropriate cell using any of the activity detection methods herein, regardless of whether the activity that is detected is the result of activity modulation, expression modulation or both.

Biosensors of the invention are devices or systems that comprise the proteins of the invention coupled to a readout that measures or displays one or more activity of the protein. Thus, any of the above described assay components can be configured as a biosensor by operably coupling the appropriate assay components to a readout. The readout can be optical (e.g., to detect cell markers or cell survival) electrical (e.g., coupled to a FET, a BIAcore, or any of a variety of others), spectrographic, or the like, and can optionally include a user-viewable display (e.g., a CRT or optical viewing station). The biosensor can be coupled to robotics or other automation, e.g., microfluidic systems, that direct contact of the test compounds to the proteins of the invention, e.g., for automated high-throughput analysis of test compound activity. A large variety of automated systems that can be adapted to use with the biosensors of the invention are commercially available. For example, automated systems have been made to assess a variety of biological phenomena, including, e.g., expression levels of genes in response to selected stimuli (Service (1998) "Microchips Arrays Put DNA on the Spot" *Science* 282: 396-399). Laboratory systems can also perform, e.g., repetitive fluid handling operations (e.g., pipetting) for transferring material to or from reagent storage systems that comprise arrays, such as microtiter trays or other chip trays, which are used as basic container elements for a variety of automated laboratory methods. Similarly, the systems manipulate, e.g., microtiter trays and control a variety of environmental conditions such as temperature, exposure to light or air, and the like. Many such automated systems are commercially available. Examples of automated systems are available from the Zymark Corporation (Zymark Center, Hopkinton, Mass.), which utilize various Zymate systems (see also, www.zymark.com/), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). A number of automated approaches to high-throughput activity screening are provided by the Genomics Institute of the Novartis Foundation (La Jolla, Calif.); See GNF.org on the world-wide web. Microfluidic screening applications are commercially available from Caliper Technologies Corp. (Mountain View, Calif.). For example, (e.g., LabMicrofluidic device® high throughput screening system (HTS) by Caliper Technologies, Mountain View, Calif. or the HP/Agilent technologies Bioanalyzer using LabChip™ technology by Caliper Technologies Corp. can be adapted for use in the present invention.

Data Systems Comprising hT1R1, hT1R2 and hT1R3 Sequences

The present invention provides databases, computers, computer readable media and systems comprising character strings corresponding to the sequence information herein for the polypeptides and nucleic acids herein, including, e.g., those sequences listed herein and the various silent substitutions and conservative substitutions thereof.

Various methods known in the art can be used to detect homology or similarity between different character strings, or can be used to perform other desirable functions such as to control output files, provide the basis for making presentations of information including the sequences and the like. Examples include BLAST, discussed supra.

Thus, different types of homology and similarity of various stringency and length can be detected, predicted and/or recognized in the data systems herein. For example, many homology determination methods have been designed for comparative analysis of sequences of biopolymers (nucleic acids, proteins, etc.), for spell-checking in word processing, and for data retrieval from various databases. With an understanding of hydrogen bonding between the principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package for calculating sequence similarity is BLAST, which can be adapted to the present invention by inputting character strings corresponding to the sequences herein. CLUSTAL provides another appropriate package.

Similarly, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Sequel™, Oracle™, Paradox™) can be adapted to the present invention by inputting a character string corresponding to the proteins or nucleic acids of the invention (either nucleic acids or proteins, or both). For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST can also be incorporated into the systems of the invention for alignment of nucleic acids or proteins (or corresponding character strings).

Systems for analysis in the present invention typically include a digital computer with an appropriate data base and a sequence of the invention. Software for aligning sequences, as well as data sets entered into the software system comprising any of the sequences herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, or LINUX based machine, a MACINTOSH™, Power PC, or a UNIX based (e.g., SUN™ work station or LINUX based machine) or other commercially common computer which is known to one of skill. Software for entering and aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display, etc.), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for controlling nucleic acid synthesis (e.g., based upon a sequence or an alignment of a sequences herein) or other operations which occur downstream from an alignment or other operation performed using a character string corresponding to a sequence herein.

Cell Rescue—Treatment

In one aspect, the invention includes rescue of a cell that is defective in function of one or more endogenous hT1Rx genes or polypeptides. This can be accomplished simply by introducing a new copy of the gene (or a heterologous nucleic acid that expresses the relevant protein) into a cell. Other approaches, such as homologous recombination to repair the defective gene (e.g., via chimeraplasty) can also be performed. In any event, rescue of function can be measured, e.g., in any of the in vitro assays noted herein. Indeed, this can be used as a general method of screening cells in vitro for an hT1Rx activity. Accordingly, in vitro rescue of function is useful in this context for the myriad in vitro screening methods noted above, e.g., for the identification of sweet or glutamate tastants in cells. The cells that are rescued can include cells in culture, (including primary or secondary cell culture from patients, as well as cultures of well-established cells). Where the cells are isolated from a patient, this has additional diagnostic utility in establishing which hT1Rx sequence is defective in a patient that presents with a tasting defect.

In another aspect, the cell rescue occurs in a patient, e.g., a human or veterinary patient, e.g., to remedy a tastant defect (for example, older patients often present with an inability to perceive sweet tastants and there are genetic defects that also present as an inability to taste sweet tastants). Thus, one aspect of the invention is gene therapy to remedy tasting defects (or even simply to enhance tastant discrimination), in human or veterinary applications. In these applications, the nucleic acids of the invention are optionally cloned into appropriate gene therapy vectors (and/or are simply delivered as naked or liposome-conjugated nucleic acids), which are then delivered (generally topically to the taste buds, but optionally systemically), optionally in combination with appropriate carriers or delivery agents. Proteins can also be delivered directly, but delivery of the nucleic acid is typically preferred in applications where stable expression is desired.

Compositions for administration, e.g., comprise a therapeutically effective amount of the gene therapy vector or other relevant nucleic acid, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering gene therapy vectors for topical use are well known in the art and can be applied to administration of the nucleic acids of the invention.

Therapeutic compositions comprising one or more nucleic acid of the invention are optionally tested in one or more appropriate in vitro and/or in vivo animal model of disease, to confirm efficacy, tissue metabolism, and to estimate dosages, according to methods well known in the art. In particular, dosages can initially be determined by activity, stability or other suitable measures of the formulation.

Administration is by any of the routes normally used for introducing a molecule into ultimate contact with taste bud cells, though topical administration or direct injection into the taste buds is simplest and therefore preferred. The nucleic acids of the invention are administered in any suitable manner, optionally with one or more pharmaceutically acceptable carriers. Suitable methods of administering such nucleic acids in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Compositions can be administered by a number of routes including, but not limited to: oral (in this case, topical and oral can be the same or different, e.g., topical delivery to the taste buds can be oral, as can systemic administration by the GI tract), intravenous, intraperitoneal, intramuscular, transdermal, subcutaneous, topical, sublingual, or rectal administration. Compositions can be administered via liposomes (e.g., topically), or via topical delivery of naked DNA or viral vectors. Such administration routes and appropriate formulations are generally known to those of skill in the art.

The compositions, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

The dose administered to a patient, in the context of the present invention, is sufficient to effect a beneficial therapeutic response in the patient over time, or, e.g., to provide sweet or glutamate tastant discrimination as perceived by the patient in an objective sweet or glutamate tastant test. The dose is determined by the efficacy of the particular vector, or other formulation, and the activity, stability or serum half-life of the polypeptide which is expressed, and the condition of the patient, as well as the body weight or surface area of the patient to be treated. The size of the dose is also determined by the existence, nature, and extent of any adverse side-effects that accompany the administration of a particular vector, formulation, or the like in a particular patient. In determining the effective amount of the vector or formulation to be administered in the treatment of disease, the physician evaluates local expression in the taste buds, or circulating plasma levels, formulation toxicities, progression of the relevant disease, and/or where relevant, the production of antibodies to proteins encoded by the polynucleotides. The dose administered, e.g., to a 70 kilogram patient are typically in the range equivalent to dosages of currently-used therapeutic proteins, adjusted for the altered activity or serum half-life of the relevant composition. The vectors of this invention can supplement treatment conditions by any known conventional therapy.

For administration, formulations of the present invention are administered at a rate determined by the LD-50 of the relevant formulation, and/or observation of any side-effects of the vectors of the invention at various concentrations, e.g., as applied to the mass or topical delivery area and overall health of the patient. Administration can be accomplished via single or divided doses.

If a patient undergoing treatment develops fevers, chills, or muscle aches, he/she receives the appropriate dose of aspirin, ibuprofen, acetaminophen or other pain/fever controlling drug. Patients who experience reactions to the compositions, such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

Kits

In an additional aspect, the present invention provides kits embodying the methods, composition, systems or apparatus herein. Kits of the invention optionally comprise one or more of the following: (1) a composition, system, system component as described herein; (2) instructions for practicing the methods described herein, and/or for using the compositions or operating the system or system components herein; (3) one or more hT1Rx composition or component; (4) a container for holding components or compositions, and, (5) packaging materials.

EXAMPLES

The following examples are offered to illustrate, but not to limit the present invention.

A search of the human genome database led to the identification of three human candidate taste receptors, hT1R1, hT1R2, and hT1R3, which contain seven transmembrane domains. All three genes map to a region of chromosome 1, which is syntenous to the distal end of chromosome 4 in mouse, which contains the Sac locus that is involved in detecting sweet tastants. A genetic marker, DVL1, which is linked to the Sac locus, is within 1,700 bp of to human T1R3. All three hT1Rs genes are all expressed selectively in human taste receptor cells in the fungiform papillae, consistent with their role in taste perception.

Accordingly, a family of putative human taste receptors, responsible for detecting sweet tastants are identified. All three hT1Rs sequences are closely related to candidate mammalian sweet taste receptors and sensory receptors (Hoon et al. (1999) Cell 96, 541-551; Montmayeur et al. (2001) Nature Neuroscience, 4, 492-498; Max et al. (2001) Nature Genetics, 28, 58-63; Brown et al. (1993) Nature 366, 575-580; and Matsunami et al. (1997) Cell 90, 775-784); all three hT1Rs contain seven-transmembrane domains, consistent with previous studies implicating G proteins in sweet taste transduction. Furthermore, all three hT1Rs localize in human chromosome 1, in accord with recent studies that show most functionally related chemosensory receptors tend to cluster in the same region of the chromosome. The mouse syntenic locus of hT1R3 is very close to the Sac locus, which has been implicated in sweet taste transduction (Fuller, J. (1974) J. Hered. 65, 33-36; Lush et al. (1995) Genet. Res. 66, 167-174; Bachmanov, A., (1997) Mamm. Genome 8, 545-548). Finally, the hT1Rs are specifically expressed in subsets of taste receptor cells in human tongue.

The results described here suggest that the T1R3 gene is responsible for the Sac phenotype (See also, Montmayer (2001) and Max (2001), above and Nelson, et al. (2001) Cell 106, 381-390).

Interestingly, in contrast to observations that shows rat T1R1 and T1R2 are expressed in same taste buds, but in most cases, not in the same cells (Hoon (1999), above), it was found that hT1R2 and hT1R3 are expressed in most of cases in the same taste cells. Thus, a single taste cell may express more than one type of taste receptors (Adler (2000), above), consistent with the experimental observations suggesting that some taste cells may respond to, but not discriminate, multiple taste stimuli (Lindemann, B. (1996) Physiol. Rev. 76, 718-766). This is in striking contrast to olfactory and vomeronasal systems, in which each receptor cell only expresses one receptor gene, providing a cellular mechanism for stimuli discrimination (Buck, L. (2000) Cell 100, 611-6). The co-expression of large subsets of T2Rs and T1Rs in individual taste cells, together with the observation that each sensory fiber innervates multiple taste buds and several taste cells within each taste bud, would result in detection of a large range of distinct tastants, but would not allow discrimination of these substances. The fact that hT1R2 and hT1R3 only share 25% sequence identity suggests distinct ligand specificity. The co-expression of hT1R2 and hT1R3 in the same taste cell reflect the possibility of heterodimer formation, which can lead to different ligand specificity relative to that of each receptor, as is the cases for many GPCR dimers. The results herein show that hT1R1 is expressed in different cells relative to hT1R2 and hT1R3.

For additional evidence that the mouse T1R2 and T1R3 combine to function as sweet receptor, and mouse T1R3 rescued the Sac phenotype, see (Nelson et al. (2001) Cell 106, 381-390). Further confirming the results herein, it has also recently been shown that the human T1R2/T1R3 recognizes diverse natural and synthetic sweeteners and that human T1R1/T1R3 responds to the umami taste stimulus 1-glutamate (Li et al. (2002) Proc. Natl. Acad. Sci. 99, 4692-4696).

Materials and Methods hT1R Gene Searching

The Framesearch program (protein query searches translated protein database) was used to search the Celera human genome database (Release R18 to R25) using rat T1R1 protein as the query. After filtering sequences containing either stop codon(s) or known genes, the contigs containing potential novel genes were submitted to Genescan gnes(dot)mit(dot)edu/GENESCAN(dot)html) for full-length gene prediction. For those exons that were missed by Genescan, TBlastN searches were applied to the same contig using rat T1R1 as the query. All novel protein sequences were subjected to a membrane domain prediction program (TopPhred 2) for verification.

The 5' end of human T1R2 was obtained by cDNA PCR. The oligonucleotide, 5'-CGCAGCAAAGCCGGGAAGCG-CACCTTGTCTC-3' (SEQ ID NO: 22) corresponding to nucleotides 515-545 of hT1R2, was used for cDNA PCR using Marathon-Ready cDNA as template (Clontech). A 600 bp fragment was obtained and cloned into Topo-2.1 vector for sequencing (Invitrogen). The deduced amino acid sequence was then assembled with the Genescan-predicted hT1R2 sequence.

Chromosome Mapping

The coding regions of hT1R1 and hT1R3 were used as queries to search the NCBI human genome database www(dot)ncbi(dot)nlm(dot)nih(dot)gov/genome/seq/page(dot)cgi?F=HsBlast.html&&ORG=Hs) to obtain the chromosome locations relative to telomere. Because the sequence of hT1R2 was not in the NCBI database, a fragment sequence from Celera contig x2HTBKLHUGU that contains the hT1R2 gene was used to search the HTGS database. A BAC clone, AL080251, was found and a search of the human genome database identified its chromosome location. Because one end of the BAC clone AL080251 was about 30 kb away from the hT1R2 gene (the putative third exon), the chromosome location of hT1R2 was deduced from its location relative to the BAC clone AL080251. The genetic marker DVL1 was initially obtained from the NCBI human genome database and used to identify the corresponding location in the mouse syntenic region from the Jackson laboratory Mouse Informatics Database www(dot)informatics(dot)jax(dot)org/menus/homology_menu(dot)shtml). The chromosome locations of mT1Rs were also obtained from the Jackson laboratory Mouse Informatics Database.

In Situ Hybridization

Human tongue tissue was obtained from a donor of 70 year old male Caucasian (National Disease Research Interchange). Fresh frozen sections (10 micrometer) of taste papillae were hybridized to digoxigenin-labelled cRNA probes prepared from cloned segments of cDNA encoding the last exons of hT1R1-3. All hybridizations were carried out at high stringency (5×SSC, 50% formamide, 55° C.). For single-label detection, signals were developed using alkaline phosphatase-conjugated antibodies to digoxigenin and NBT/BCIP substrate (Roshe). For two-color fluorescent in situ hybridization, sections of taste papillae were hybridized simultaneously to both digoxigenin-(hT1R2) and fluorescein-(hT1R3) labeled cRNA probes (Roche). Following hybridization, the labeled probes were recognized with peroxidase-anti-digoxigenin and alkaline phosphatase-anti-fluorescein antibodies, respectively (Roche). The tyramide-biotin/streptavidin-Alexa 488 (NEN and Molecular Probe) and HNPP/fast red (Roche) were then used as substrates for fluorescent labeling with peroxidase and alkaline phosphatase, respectively. Sections were mounted in VECTASHIELD Mounting Medium with DAPI (VECTOR Laboratories) to counterstain nuclei.

In one experiment, expression of the three sweet receptor mRNAs in human taste cells was analyzed. Frozen sections of human fungiform taste papillae were hybridized with digoxigenin-labelled hT1R1, hT1R2, hT1R3 cRNA probes in either anti-sense or sense orientation. The level of expression of hT1R1 was observed to be very low compared to that of hT1R2 and T1R3. The papillae from an adjacent section hybridized to the sense probe and showed no non-specific binding.

In another experiment, it was determined that hT1R2 colocalizes with hT1R3 in human taste receptor cells. Papillae from human fungiform were hybridized simultaneously with a digoxigenin-labelled hT1R2 and a fluorescein-labelled T1R3 probe. The digoxigenin-labelled T1R2 probe and fluorescein-labeled T1R3 probe were imaged with Alexa 488 (green) and HNPP/fast red (red), respectively. The overlay of the two images shows that some cells coexpress T1R2 and T1R3 (yellow).

Example 1

Identification of Human Sweet Receptor Genes

A series of search/verification criteria were initially developed as part of the search procedure. The search was carried out using both DNA and protein sequences as queries to increase the possibility of discovering new genes in the human genome. The candidate fragments/genes were evaluated based on existing knowledge of GPCRs and taste receptors, i.e., the sequences of sweet receptors are related to each other; the deduced amino acid sequences should show seven transmembrane domains; and the sweet receptors should be clustered in the same chromosome region. Rat T1R1 (rT1R1) was first utilized as the query to search all public genome and EST databases. No homologous sequences were found initially. The Celera human genome database in an unassembled version was then searched, using the Framesearch program. More than twenty fragments encoding peptides showing similarity to rT1R1 protein were discovered. PCR was used to assess the expression of these fragments. Seven fragments were expressed in testis. Although it is possible that these fragments come from the same gene, the fact that several different peptides encoded by these fragments show homology to the same region of rT1R1 suggest that there may be several T1R1 homologues in human.

After the small DNA fragments were assembled into larger fragments, the database was searched again. Based on similarity scores, eleven sequences were chosen for further evaluation. Of these eleven sequences, five fragments were excluded because they contain stop codons in the coding regions, suggesting that they might be pseudogenes. The remaining six fragments were further characterized. Of these, two fragments correspond to two known genes-metabotropic glutamate receptor 3 and $Ca^{2+}$ sensor 5, and three encode peptides that are homologous to rat T1R1 and are localized in chromosome 1 (see below). The full-length coding region of these three genes was predicted from their corresponding contigs (x8YLHLD for putative hT1R1, x2HTBKLHUGU for putative hT1R2, x2HTBKWRET8 for putative hT1R3) by using the Genscan gene prediction program and tBlastN with rat T1R1 as the query. Two full-length genes encoding proteins with seven transmembrane helices are predicted. The third gene, which encodes a peptide more closely related to rat T1R2, lacks approximately 150 amino acids at the N-terminus due to the fact that the contig x2HTBKLHUGU has several un-sequenced gaps in the putative exon 1 and 2 coding-regions. The EST database was also searched to find any ESTs corresponding to hT1Rs, but none were found, suggesting tissue-specific and/or low-level expressions.

The PCR method was then utilized to obtain the 5' sequence of the putative human T1R2 cDNA. Using a gene-specific primer, a 600 bp fragment was obtained from human testis cDNA template. Sequencing revealed an in-frame-peptide that is very similar to the N-terminal 150 amino acids of rat T1R2 N-terminus, strongly suggesting this to be 5' sequences of hT1R2 cDNA.

The deduced amino acid sequences of all three human T1Rs show a high degree of homology to both their mouse and rat counterparts (FIG. 1). hT1R1 (SEQ ID NO:1) shows much higher sequence identity to its orthologoue, mT1R1 (SEQ ID NO:2) in mouse and rT1R1 (SEQ ID NO:3) in rat (69.8% and 70.0% amino acid identity, respectively) than its homologues, hT1R2 (SEQ ID NO:4) and hT1R3 (SEQ ID NO:7) (30.7% and 26.0%, respectively). The same is true for the other two members: hT1R2 (SEQ ID NO:4) shows 67.9% and 70.4% amino acid identity to mT1R2 (SEQ ID NO:5) and rT1R2 (SEQ ID NO:6), respectively; hT1R3 (SEQ ID NO:7) shows 72% identity to mT1R3 (SEQ ID NO:8). This group of human taste receptors belongs to GPCR subfamily 3, which includes metabotropic glutamate receptors, extracellular $Ca^{2+}$ sensors, and pheromone receptors. All three hT1Rs have long N-terminal extracellular domains (FIG. 1), similar to other members of this family of GPCRs. This long N-terminal extracellular domain has been suggested to function in dimerization and/or ligand binding as described, e.g., in Kunishima et al., *Nature* 407: 971-977, 2000. The nucleotide sequences of the hT1R1 (SEQ ID NO:10), hT1R2 (SEQ ID NO:11) and hT1R3 (SEQ ID NO:12) cDNAs are shown in FIGS. 2A, 2B, and 2C, respectively.

The three hT1Rs are encoded by a similar number of exons, hT1R1 and hT1R3 by 6 exons, and hT1R2 by more than 5 exons. This result is consistent with that of the mouse T1Rs, as described by Montmayeur et al., *Nature Neuroscience* 4:492-498, 2001. However, the hT1Rs genes span different sizes in the chromosome: the hT1R1 coding region spans 24 kb; hT1R2 occupies more than 15 kb, and hT1R3 is only 4 kb in size (FIG. 3, see below). Interestingly, all the transmembrane domains are encoded by the last and also the largest exon for all three hT1Rs.

Example 2

Mapping of the Human T1Rs Receptor Genes to a Region in Chromosome 1, the Syntenic Region of Mouse Distal Chromosome 4 End Containing the Sac Locus We then asked whether the human T1Rs co-localize to the same chromosome, as might be expected for taste receptors having similar properties. Using hT1R1 to search the human genome database in NCBI, the hT1R1 gene was found to be localized in the contig NT_019267, which maps to chromosome 1. The coding region of hT1R1 spans 24 kb from 12433K to 12409K of chromosome 1 (FIG. 3). Unfortunately, hT1R2 was not able to be mapped directly because there is no corresponding clone in the NCBI human genome database. An electronic chromosome walking strategy was used to find overlapping clones. Using a sequence in the region of 2.16 Mp from Celera contig x2HTBKLHUGU, an overlapping BAC clone, AL080251 was found, which has been assigned to chromosome 1p35.2-p36.23. The end of the AL080251 clone, 30 kb from the hT1R2 gene, maps to a position of 13804K in chromosome 1. The location of hT1R was at 13776K to 13761K in chromosome 1 (FIG. 3). Using the same approach for hT1R1, hT1R3 was found to be localized to a region of 4 kb, from 61116K to 61111K in human chromosome 1 (FIG. 3). This region belongs to contig NT_025635. To find the locus information, the human high-throughput genome project database (htgs) was also searched and hT1R3 was found in two BAC clones, AC026283 and AL139287. These two BAC clones, however, have not been assigned to a locus in the chromosome. We then used the electronic chromosome walking strategy again to find a overlapping BAC clone, AL391244.11, which overlaps with AC026283 and is assigned to human chromosome 1p36.31-36.33.

The above results show that all three human T1Rs indeed form a cluster in chromosome 1. Using The Jackson Laboratory Mouse Informatics database, the corresponding region in mouse was determined to be distal chromosome 4. Interestingly, the Sac locus has been mapped to the same distal region of chromosome 4 at about 83 cM, as described by Fuller, *J. Hered.* 65:33-36, 1974; Lush et al. Genet. Res. 66:167-174, 1995; and Bachmanov, *Mamm. Genome* 8:545-548, 1997. Recently, mT1R1 has also been mapped to this region, approximately 5 cM from the Sac locus as described, e.g., in Li et al., *Mamm. Genome* 12: 13-15, 2001. hT1R1 shows very high sequence similarity to mT1R1 (69.8%, see above). These results suggest that there might be a sweet receptor cluster in this region. To determine whether any of the hT1Rs identified may be an orthologue of Sac locus, several genetic markers closely linked to hT1Rs were examined. One of the markers, DVL1-a human dishevelled homologue, which is tightly linked to the hT1R3 gene only about 1,700 bp away, was found to map to the distal end of chromosome 4 at 82.0 cM. This location is very close to the mapped Sac locus at 83 cM, suggesting the likelihood of T1R3 as a gene of the Sac locus. Recently, two papers have been published which also suggest that T1R3 is the closest GPCR gene to Sac locus (see, e.g., Montmayeur et al., supra; and Max et al., *Nature Genetics* 28:58-63, 2001.

Example 3

Expression of hT1Rs in Taste Cells

If hT1Rs are taste receptors, they should be expressed in taste tissues. According to classical models of taste discrimination, fungiform papillae are more sensitive to sweet substances than other regions of the tongue. To examine the expression of the hT1Rs, in situ hybridizations were carried out with sections containing human fungiform taste papillae. All three hT1Rs genes were found to be selectively expressed in a subset of taste receptor cells, but absent from surrounding lingual epithelium. Control sense cRNA probes did not hybridize to the taste cells in the immediate adjacent sections. The hT1R2 and hT1R3 probes hybridize to approximately 10-20% of taste cells. The hybridization signal for hT1R1 was much weaker than those for hT1R2 and hT1R3 in fungiform papillae. The hybridization signals for hT1R1 were also very weak in circumvallate and foliate taste papillae. These results are consistent with those described for the recently published mouse T1Rs as described in Montmayeur et al., supra.

A preliminary analysis of the expression pattern of the hT1Rs was also carried out. In most cases, T1R1 was expressed in different taste buds from that of hT1R2 and hT1R3, consistent with the previous studies for rat rT1R1 and rT1R2 (see Hoon et al., supra). Surprisingly, hT1R2 and hT1R3 are expressed in the same taste bud in single-labeling in situ experiments. To examine whether hT1R2 and hT1R3 might be expressed in the same taste cells, a fungiform papillae section was hybridized with different labeled-hT1R2 and hT1R3 cRNA probes simultaneously. The results from the hybridization studies show that hT1R2 and hT1R3 are expressed largely in the same taste cells (5 of 5 taste buds examined in the section). However, some T1R2-expressing cells do not express T1R3. These results are in contrast to a recent observation that mouse all T1R2-expressing cells also express T1R3 (see also, Montmayeur et al., supra).

It is understood that the examples and embodiments described herein are for illustrative purposes only and that various modifications or changes in light thereof will be suggested to persons skilled in the art and are to be included within the spirit and purview of this application and scope of the appended claims. Thus, the above description should not be construed as limiting, but merely as exemplification of preferred embodiments.

All patent applications, patents and literature references cited herein are hereby incorporated by reference in their entirety for all purposes to the same extent as if every such patent application, patent, or literature reference were indicated to be incorporated by reference in its entirety.

SEQUENCE TABLE

Example T1Rx Nucleic Acids And Polypeptides

>hT1R1 (Nucleic Acid; SEQ ID NO:10)
ATGCTGCTCTGCACGGCTCGCCTGGTCGGCCTGCAGCTTCTCATTTCCTGCTGCTGGGCCTTTGCCTGCCATAGCACGGA

GTCTTCTCCTGACTTCACCCTCCCCGGAGATTACCTCCTGGCAGGCCTGTTCCCTCTCCATTCTGGCTGTCTGCAGGTGA

GGCACAGACCCGAGGTGACCCTGTGTGACAGGTCTTGTAGCTTCAATGAGCATGGCTACCACCTCTTCCAGGCTATGCGG

CTTGGGGTTGAGGAGATAAACAACTCCACGGCCCTGCTGCCCAACATCACCCTGGGGTACCAGCTGTATGATGTGTGTTC

TGACTCTGCCAATGTGTATGCCACGCTGAGAGTGCTCTCCCTGCCAGGGCAACACCACATAGAGCTCCAAGGAGACCTTC

TCCACTATTCCCCTACGGTGCTGGCAGTGATTGGGCCTGACAGCACCAACCGTGCTGCCACCACAGCCGCCCTGCTGAGC

CCTTTCCTGGTGCCCATGCTTATTAGCTATGCGGCCAGCAGCGAGACGCTCAGCGTGAAGCGGCAGTATCCCTCTTTCCT

GCGCACCATCCCCAATGACAAGTACCAGGTGGAGACCATGGTGCTGCTGCTGCAGAAGTTCGGGTGGACCTGGATCTCTC

TGGTTGGCAGCAGTGACGACTATGGGCAGCTAGGGGTGCAGGCACTGGAGAACCAGGCCACTGGTCAGGGGATCTGCATT

GCTTTCAAGGACATCATGCCCTTCTCTGCCCAGGTGGGCGATGAGAGGATGCAGTGCCTCATGCGCCACCTGGCCCAGGC

CGGGGCCACCGTCGTGGTTGTTTTTTCCAGCCGGCAGTTGGCCAGGGTGTTTTCGAGTCCGTGGTGCTGACCAACCTGA

CTGGCAAGGTGTGGGTCGCCTCAGAAGCCTGGGCCCTCTCCAGGCACATCACTGGGGTGCCCGGGATCCAGCGCATTGGG

ATGGTGCTGGGCGTGGCCATCCAGAAGAGGGCTGTCCCTGGCCTGAAGGCGTTTGAAGAAGCCTATGCCCGGGCAGACAA

GGAGGCCCCTAGGCCTTGCCACAAGGGCTCCTGGTGCAGCAGCAATCAGCTCTGCAGAGAATGCCAAGCTTTCATGGCAC

ACACGATGCCCAAGCTCAAAGCCTTCTCCATGAGTTCTGCCTACAACGCATACCGGGCTGTGTATGCGGTGGCCCATGGC

CTCCACCAGCTCCTGGGCTGTGCCTCTGGAGCTTGTTCCAGGGGCCGAGTCTACCCCTGGCAGTTGGAGCAGATCCACAA

GGTGCATTTCCTTCTACAAGGACACTGTGGCGTTTAATGACAACAGAGATCCCCTCAGTAGCTATAACATAATTGCCT

GGGACTGGAATGGACCCAAGTGGACCTTCACGGTCCTCGGTTCCTCCACATGGTCTCCAGTTCAGCTAAACATAAATGAG

ACCAAAATCCAGTGGCACGGAAAGGACAACCAGGAACCAAGTCTGTGTGTTCCAGCGACTGTCTTGAAGGGCACCAGCGA

GTGGTTACGGGTTTCCATCACTGCTGCTTTGAGTGTGTGCCCTGTGGGGGGTTCTTGGCCTTCCCTTTCAGACCTCTACA

GATGCCAGCCTTGTGGGAAAGAAGAGTGGGCACCTGAGGGAAGCCAGACCTGCTTCCCGCGCACTGTGGTGTTTTGGCT

TTGCGTGAGCACACCTCTTGGGTGCTGCTGGCAGCTAACACGCTGCTGCTGCTGCTGCTTGGGACTGCTGGCCTGTT

TGCCTGGCACCTAGACACCCCTGTGGTGAGGTCAGCAGGGGGCCGCCTGTGCTTTCTTATGCTGGGCTCCCTGGCAGCAG

GTAGTGGCAGCCTCTATGGCTTCTTTGGGGAACCCACAAGGCCTGCGTGCTTGCTACGCCAGGCCCTCTTTGCCCTTGGT

TTCACCATCTTCCTGTCCTGCCTGACAGTTCGCTCATTCCAACTAATCATCATCTTCAAGTTTTCCACCAAGGTACCTAC

ATTCTACCACGCCTGGGTCCAAAACCACGGTGCTGGCCTGTTTGTGATGATCAGCTCAGCGGCCCAGCTGCTTATCTGTC

TAACTTGGCTGGTGGTGTGGACCCCACTGCCTGCTAGGGAATACCAGCGCTTCCCCCATCTGGTGATGCTTGAGTGCACA

GAGACCAACTCCCTGGGCTTCATACTGGCCTTCCTCTACAATGGCCTCCTCTCCATCAGTGCCTTTGCCTGCAGCTACCT

GGGTAAGGACTTGCCAGAGAACTACAACGAGGCCAAATGTGTCACCTTCAGCCTGCTCTTCAACTTCGTGTCCTGGATCG

CCTTCTTCACCACGGCCAGCGTCTACGACGGCAAGTACCTGCCTGCGGCCAACATGATGGCTGGGCTGAGCAGCCTGAGC

AGCGGCTTCGGTGGGTATTTTCTGCCTAAGTGCTACGTGATCCTCTGCCGCCCAGACCTCAACAGCACAGAGCACTTCCA

GGCCTCCATTCAGGACTACACGAGGCGCTGCGGCTCCACCTGA

>hT1R1 (amino acid; SEQ ID NO:1)
MLLCTARLVGLQLLISCCWAFACHSTESSPDFTLPGDYLLAGLFPLHSGCLQVRHRPEVTLCDRSCSFNEHGYHLFQAMR

LGVEEINNSTALLPNITLGYQLYDVCSDSANVYATLEVLSLPGQHHIELQGDLLHYSPTVLAVIGPDSTNRAATTAALLS

SEQUENCE TABLE-continued

Example T1Rx Nucleic Acids And Polypeptides

PFLVPMLISYAASSETLSVKRQYPSFLRTIPNDKYQVETMVLLLQKFGWTWISLVGSSDDYGQLGVQALENQATGQGICI

AFKDIMPFSAQVGDERMQCLMRHLAQAGATVVVVFSSRQLARVFFESVVLTNLTGKVWVASEAWALSRHITGVPGIQRIG

MVLGVAIQKRAVPGLKAFEEAYARADKEAPRPCHKGSWCSSNQLCRECQAFMAHTMPKLKAFSMSSAYNAYRAVYAVAHG

LHQLLGCASGACSRGRVYPWQLEQIHKVHFLLHKDTVAFNDNRDPLSSYNIIAWDWNGPKWTFTVLGSSTWSPVQLNINE

TKIQWHGKDNQEPSLCVPATVLKGTSEWLRVSITAALSVCPVGGSWPSLSDLYRCQPCGKEEWAPEGSQTCFPRTVVFLA

LREHTSWVLLAANTLLLLLLLGTAGLFAWHLDTPVVRSAGGRLCFLMLGSLAAGSGSLYGFFGEPTRPACLLRQALFALG

FTIFLSCLTVRSFQLIIIFLFSTKVPTFYHAWVQNHGAGLFVMISSAAQLLICLTWLVVWTPLPAREYQRFPHLVMLECT

ETNSLGFILAFLYNGLLSISAFACSYLGKDLPENYNEAKCVTFSLLFNFVSWIAFFTTASVYDGKYLPAANMMAGLSSLS

SGFGGYFLPKCYVILCRPDLNSTEHFQASIQDYTRRCGST.

>hT1R2 (nucleic acid; SEQ ID NO: 11)
ATGGGGCCCAGGGCAAAGACCATCTGCTCCCTGTTCTTCCTCCTATGGGTCCTGGCTGAGCCGGCTGAGAACTCGGACTT

CTACCTGCCTGGGGATTACCTCCTGGGTGGCCTCTTCTCCCTCCATGCCAACATGAAGGGCATTGTTCACCTTAACTTCC

TGCAGGTGCCCATGTGCAAGGAGTATGAAGTGAAGGTGATAGGCTACAACCTCATGCAGGCCATGCGCTTTGCGGTGGAG

GAGATCAACAATGACAGCAGCCTGCTGCCTGGTGTGCTGCTGGGCTATGAGATCGTGGATGTGTGCTACATCTCCAACAA

TGTCCAGCCGGTGCTCTACTTCCTGGCACACGGGGACAACCTCCTTCCCATCCAAGAGGACTACAGTAACTACATTTCCC

GTGCGGTGGCTGTCATTGGCCCTGACAACTCCGAGTCTGTCATGACTGTGGCCAACTTCCTCTCCCTATTTCTCCTTCCA

CAGATCACCTACAGCGCCATCAGCGATGAGCTGCGAGACAAGGTGCGCTTCCCGGCTTTGCTGCGTACCACACCCAGCGC

CGACCACCACATCGAGGCCATGGTGCAGCTGATGCTGCACTTCCGCTGGAACTGGATCATTGTGCTGGTGAGCAGCGACA

CCTATGGCCGCGACAATGGCCAGCTGCTTGGCGAGCGCGTGGCCCGGCGCGACATCTGCATCGCCTTCCAGGAGACGCTG

CCCACACTGCAGCCCAACCAGAACATGACGTCAGAGGAGCGCCAGCGCCTGGTGACCATTGTGGACAAGCTGCAGCAGAG

CACAGCGCGCGTCGTGGTCGTGTTCTCGCCCGACCTGACCCTGTACCACTTCTTCAATGAGGTGCTGCGCCAGAACTTCA

CTGGCGCCGTGTGGATCGCCTCCGAGTCCTGGGCCATCGACCCGGTCCTGCACAACCTCACGGAGCTGCGCCACTTGGGC

ACCTTCCTGGGCATCACCATCCAGAGCGTGCCCATCCCGGGCTTCAGTGAGTTCCGCGAGTGGGGCCCACAGGCTGGGCC

GCCACCCCTCAGCAGGACCAGCCAGAGCTATACCTGCAACCAGGAGTGCGACAACTGCCTGAACGCCACCTTGTCCTTCA

ACACCATTCTCAGGCTCTCTGGGGAGCGTGTCGTCTACAGCGTGTACTCTGCGGTCTATGCTGTGGCCCATGCCCTGCAC

AGCCTCCTCGGCTGTGACAAAAGCACCTGCACCAAGAGGGTGGTCTACCCCTGGCAGCTGCTTGAGGAGATCTGGAAGGT

CAACTTCACTCTCCTGGACCACCAAATCTTCTTCGACCCGCAAGGGGACGTGGCTCTGCACTTGGAGATTGTCCAGTGGC

AATGGGACCGGAGCCAGAATCCCTTCCAGAGCGTCGCCTCCTACTACCCCCTGCAGCGACAGCTGAAGAACATCCAAGAC

ATCTCCTGGCACACCATCAACAACACGATCCCTATGTCCATGTGTTCCAAGAGGTGCCAGTCAGGGCAAAAGAAGAAGCC

TGTGGGCATCCACGTCTGCTGCTTCGAGTGCATCGACTGCCTTCCCGGCACCTTCCTCAACCACACTGAAGATGAATATG

AATGCCAGGCCTGCCCGAATAACGAGTGGTCCTACCAGAGTGAGACCTCCTGCTTCAAGCGGCAGCTGGTCTTCCTGGAA

TGGCATGAGGCACCCACCATCGCTGTGGCCCTGCTGGCCGCCCTGGGCTTCCTCAGCACCCTGGCCATCCTGGTGATATT

CTGGAGGCACTTCCAGACACCCATAGTTCGCTCGGCTGGGGCCCCATGTGCTTCCTGATGCTGACACTGCTGCTGGTGG

CATACATGGTGGTCCCGGTGTACGTGGGGCCGCCCAAGGTCTCCACCTGCCTCTGCCGCCAGGCCCTCTTTCCCCTCTGC

TTCACAATCTGCATCTCCTGTATCGCCGTGCGTTCTTTCCAGATCGTCTGCGCCTTCAAGATGGCCAGCCGCTTCCCACG

CGCCTACAGCTACTGGGTCCGCTACCAGGGGCCCTACGTCTCTATGGCATTTATCACGGTACTCAAAATGGTCATTGTGG

TAATTGGCATGCTGGCCACGGGCCTCAGTCCCACCACCCGTACTGACCCCGATGACCCCAAGATCACAATTGTCTCCTGT

AACCCCAACTACCGCAACAGCCTGCTGTTCAACACCAGCCTGGACCTGCTGCTCTCAGTGGTGGGTTTCAGCTTCGCCTA

CATGGGCAAAGAGCTGCCCACCAACTACAACGAGGCCAAGTTCATCACCCTCAGCATGACCTTCTATTTCACCTCATCCG

SEQUENCE TABLE-continued

Example T1Rx Nucleic Acids And Polypeptides

TCTCCCTCTGCACCTTCATGTCTGCCTACAGCGGGGTGCTGGTCACCATCGTGGACCTCTTGGTCACTGTGCTCAACCTC

CTGGCCATCAGCCTGGGCTACTTCGGCCCCAAGTGCTACATGATCCTCTTCTACCCGGAGCGCAACACGCCCGCCTACTT

CAACAGCATGATCCAGGGCTACACCATGAGGAGGGACTAG

>hT1R2 (amino acid; SEQ ID NO: 4)
MGPRAKTICSLFFLLWVLAEPAENSDFYLPGDYLLGGLFSLHANMKGIVHLNFLQVPMCKEYEVKVIGYNLNQAMRFAVE

EINNDSSLLPGVLLGYEIVDVCYISNNVQPVLYFLAHGDNLLPIQEDYSNYISRAVAVIGPDNSESVMTVANFLSLFLLP

QITYSAISDELRDKVRFPALLRTTPSADHHIEAMVQLMLHFRWNWIIVLVSSDTYGRDNGQLLGERVARRDICIAFQETL

PTLQPNQNMTSEERQRLVTIVDKLQQSTARVVVVFSPDLTLYHFFNEVLRQNFTGAVWIASESWAIDPVLHNLTELRHLG

TFLGITIQSVPIPGFSEFREWGPQAGPPPLSRTSQSYTCNQECDNCLNATLSFNTILRLSGERVVYSVYSAVYAVAHALH

SLLGCDKSTCTKRVVYPWQLLEEIWKVNFTLLDHQIFFDPQGDVALHLEIVQWQWDRSQNPFQSVASYYPLQRQLKNIQD

ISWHTINNTIPMSMCSKRCQSGQKKKPVGIHVCCFECIDCLPGTFLNHTEDEYECQACPNNEWSYQSETSCFKRQLVFLE

WHEAPTIAVALLAALGFLSTLAILVIFWRHFQTPIVRSAGGPMCFLMLTLLLVAYMVVPVYVGPPKVSTCLCRQALFPLC

FTICISCIAVRSFQIVCAFKMASRFPRAYSYWVRYQGPYVSMAFITVLKMVIVVIGMLATGLSPTTRTDPDDPKITIVSC

NPNYRNSLLFNTSLDLLLSVVGFSFAYMGKELPTNYNEAKFITLSMTFYFTSSVSLCTFMSAYSGVLVTIVDLLVTVLNL

LAISLGYFGPKCYMILFYPERNTPAYFNSMIQGYTMRRD.

>hT1R3 (nucleic acid; SEQ ID NO: 12)
ATGCTGGGCCCTGCTGTCCTGGGCCTCAGCCTCTGGGCTCTCCTGCACCCTGGGACGGGGGCCCATTGTGCCTGTCACA

GCAACTTAGGATGAAGGGGGACTACGTGCTGGGGGGGCTGTTCCCCCTGGGCGAGGCCGAGGAGGCTGGCCTCCGCAGCC

GGACACGGCCCAGCAGCCCTGTGTGCACCAGGTTCTCCTCAAACGGCCTGCTCTGGGCACTGGCCATGAAAATGGCCGTG

GAGGAGATCAACAACAAGTCGGATCTGCTGCCCGGGCTGCGCCTGGGCTACGACCTCTTTGATACGTGCTCGGAGCCTGT

GGTGGCCATGAAGCCCAGCCTCATGTTCCTGGCCAAGGCAGGCAGCCGCGACATCGCCGCCTACTGCAACTACACGCAGT

ACCAGCCCCGTGTGCTGGCTGTCATCGGGCCCCACTCGTCAGAGCTCGCCATGGTCACCGGCAAGTTCTTCAGCTTCTTC

CTCATGCCCCAGGTCAGCTACGGTGCTAGCATGGAGCTGCTGAGCGCCCGGGAGACCTTCCCCTCCTTCTTCCGCACCGT

GCCCAGCGACCGTGTGCAGCTGACGGCCGCCGCGGAGCTGCTGCAGGAGTTCGGCTGGAACTGGGTGGCCGCCCTGGGCA

GCGACGACGAGTACGGCCGGCAGGGCCTGAGCATCTTCTCGGCCCTGGCCGCGGCACGCGGCATCTGCATCGCGCACGAG

GGCCTGGTGCCGCTGCCCCGTGCCGATGACTCGCGGCTGGGGAAGGTGCAGGACGTCCTGCACCAGGTGAACCAGAGCAG

CGTGCAGGTGGTGCTGCTGTTCGCCTCCGTGCACGCCGCCCACGCCCTCTTCAACTACAGCATCAGCAGCAGGCTCTCGC

CCAAGGTGTGGGTGGCCAGCGAGGCCTGGCTGACCTCTGACCTGGTCATGGGGCTGCCCGGCATGGCCCAGATGGGCACG

GTGCTTGGCTTCCTCCAGAGGGGTGCCCAGCTGCACGAGTTCCCCCAGTACGTGAAGACGCACCTGGCCCTGGCCACCGA

CCCGGCCTTCTGCTCTGCCCTGGGCGAGAGGGAGCAGGGTCTGGAGGAGGACGTGGTGGGCCAGCGCTGCCCGCAGTGTG

ACTGCATCACGCTGCAGAACGTGAGCGCAGGGCTAAATCACCACCAGACGTTCTCTGTCTACGCAGCTGTGTATAGCGTG

GCCCAGGCCCTGCACAACACTCTTCAGTGCAACGCCTCAGGCTGCCCCGCGCAGGACCCCGTGAAGCCCTGGCAGCTCCT

GGAGAACATGTACAACCTGACCTTCCACGTGGGCGGGCTGCCGCTGCGGTTCGACAGCAGCGGAAACGTGGACATGGAGT

ACGACCTGAAGCTGTGGGTGTGGCAGGGCTCAGTGCCCAGGCTCCACGACGTGGGCAGGTTCAACGGCAGCCTCAGGACA

GAGCGCCTGAAGATCCGCTGGCACACGTCTGACAAGCCCGTGTCCCGGTGCTCGCGGCAGTGCCAGGAGGGCCAGGTGCG

CCGGGTCAAGGGGTTCCACTCCTGCTGCTACGACTGTGTGGACTGCGAGGCGGGCAGCTACCGGCAAAACCCAGACGACA

TCGCCTGCACCTTTTGTGGCCAGGATGAGTGGTCCCCGGAGCGAAGCACACGCTGCTTCCGCCGCAGGTCTCGGTTCCTG

GCATGGGGCGAGCCGGCTGTGCTGCTGCTGCTCCTGCTGCTGAGCCTGGCGCTGGGCCTTGTGCTGGCTGCTTTGGGGCT

GTTCGTTCACCATCGGGACAGCCCACTGGTTCAGGCCTCGGGGGGGCCCCTGGCCTGCTTTGGCCTGGTGTGCCTGGGCC

TGGTCTGCCTCAGCGTCCTCCTGTTCCCTGGCCAGCCCAGCCCTGCCCGATGCCTGGCCCAGCAGCCCTTGTCCCACCTC

SEQUENCE TABLE-continued

Example T1Rx Nucleic Acids And Polypeptides

```
CCGCTCACGGGCTGCCTGAGCACACTCTTCCTGCAGGCGGCCGAGATCTTCGTGGAGTCAGAACTGCCTCTGAGCTGGGC
AGACCGGCTGAGTGGCTGCCTGCGGGGCCCTGGGCCTGGCTGGTGGTGCTGCTGGCCATGCTGGTGGAGGTCGCACTGT
GCACCTGGTACCTGGTGGCCTTCCCGCCGGAGGTGGTGACGGACTGGCACATGCTGCCCACGGAGGCGCTGGTGCACTGC
CGCACACGCTCCTGGGTCAGCTTCGGCCTAGCGCACGCCACCAATGCCACGCTGGCCTTTCTCTGCTTCCTGGGCACTTT
CCTGGTGCGGAGCCAGCCGGGCCGCTACAACCGTGCCCGTGGCCTCACCTTTGCCATGCTGGCCTACTTCATCACCTGGG
TCTCCTTTGTGCCCCTCCTGGCCAATGTGCAGGTGGTCCTCAGGCCCGCCGTGCAGATGGGCGCCCTCCTGCTCTGTGTC
CTGGGCATCCTGGCTGCCTTCCACCTGCCCAGGTGTTACCTGCTCATGCGGCAGCCAGGGCTCAACACCCCCGAGTTCTT
CCTGGGAGGGGCCCTGGGGATGCCCAAGGCCAGAATGACGGGAACACAGGAAATCAGGGGAAACATGAGTGA
```

>hT1R3                                                      (amino acid; SEQ ID NO: 7)
```
MLGPAVLGLSLWALLHPGTGAPLCLSQQLRMKGDYVLGGLFPLGEAEEAGLRSRTRPSSPVCTRFSSNGLLWALAMKMAV
EEINNKSDLLPGLRLGYDLFDTCSEPVVAMKPSLMFLAKAGSRDIAAYCNYTQYQPRVLAVIGPHSSELAMVTGKFFSFF
LMPQVSYGASMELLSARETFPSFFRTVPSDRVQLTAAAELLQEFGWNWVAALGSDDEYGRQGLSIFSALAAARGICIAHE
GLVPLPRADDSRLGKVQDVLHQVNQSSVQVVLLFASVHAAHALFNYSISSRLSPKVWVASEAWLTSDLVMGLPGMAQMGT
VLGFLQRGAQLHEFPQYVKTHLALATDPAFCSALGEREQGLEEDVVGQRCPQCDCITLQNVSAGLNHHQTFSVYAAVYSV
AQALHNTLQCNASGCPAQDPVKPWQLLENMYNLTFHVGGLPLRFDSSGNVDMEYDLKLWVWQGSVPRLHDVGRFNGSLRT
ERLKIRWHTSDKPVSRCSRQCQEGQVRRVKGFHSCDYDCVDCEAGSYRQNPDDIACTFCGQDEWSPERSTRCFRRRSRFL
AWGEPAVLLLLLLLSLALGLVLAALGLFVHHRDSPLVQASGGPLACFGLVCLGLVCLSVLLFPGQPSPARCLAQQPLSHL
PLTGCLSTLFLQAAEIFVESELPLSWADRLSGCLRGPWAWLVVLLAMLVEVALCTWYLVAFPPEVVTDWHMLPTEALVHC
RTRSWVSFGLAHATNATLAFLCFLGTFLVRSQPGRYNRARGLTFAMLAYFITWVSFVPLLANVQVVLRPAVQMGALLLCV
LGILAAFHLPRCYLLMRQPGLNTPEFFLGGGPGDAQGQNDGNTGNQGKHE.
```

>mT1R1                                                      (Nucleic Acid; SEQ ID NO. 13)
```
ATGCTTTTCTGGGCAGCTCACCTGCTGCTCAGCCTGCAGCTGGCCGTTGCTTACTGCTGGGCTTTCAGCTGCCAAAGGAC
AGAATCCTCTCCAGGTTTCAGCCTCCCTGGGGACTTCCTCCTGGCAGGCCTGTTCTCCCTCCATGCTGACTGTCTGCAGG
TGAGACACAGACCTCTGGTGACAAGTTGTGACAGGTCTGACAGCTTCAACGGCCATGGCTATCACCTCTTCCAAGCCATG
CGGTTCACCGTTGAGGAGATAAACAACTCCACAGCTCTGCTTCCCAACATCACCCTGGGGTATGAACTGTATGACGTGTG
CTCAGAGTCTTCCAATGTCTATGCCACCCTGAGGGTGCCCGCCCAGCAAGGGACAGGCCACCTAGAGATGCAGAGAGATC
TTCGCAACCACTCCTCCAAGGTGGTGGCACTCATTGGGCCTGATAACACTGACCACGCTGTCACCACTGCTGCCCTGCTG
AGCCCTTTTCTGATGCCCCTGGTCAGCTATGAGGCGAGCAGCGTGATCCTCAGTGGGAAGCGCAAGTTCCCGTCCTTCTT
GCGCACCATCCCCAGCGATAAGTACCAGGTGGAAGTCATAGTGCGGCTGCTGCAGAGCTTCGGCTGGGTCTGGATCTCGC
TCGTTGGCAGCTATGGTGACTACGGGCAGCTGGGCGTACAGGCGCTGGAGGAGCTGGCCACTCCACGGGGCATCTGCGTC
GCCTTCAAGGACGTGGTGCCTCTCTCCGCCCAGGCGGGTGACCCAAGGATGCAGCGCATGATGCTGCGTCTGGCTCGAGC
CAGGACCACCGTGGTCGTGGTCTTCTCTAACCGGCACCTGGCTGGAGTGTTCTTCAGGTCTGTGGTGCTGGCCAACCTGA
CTGGCAAAGTGTGGATCGCCTCCGAAGACTGGGCCATCTCCACGTACATCACCAATGTGCCCGGGATCCAGGGCATTGGG
ACGGTGCTGGGGGTGGCCATCCAGCAGAGACAAGTCCCTGGCCTGAAGGAGTTTGAAGAGTCCTATGTCCAGGCAGTGAT
GGGTGCTCCCAGAACTTGCCCAGAGGGGTCCTGGTGCGGCACTAACCAGCTGTGCAGGGAGTGTCACGCTTTCACGACAT
GGAACATGCCCGAGCTTGGAGCCTTCTCCATGAGCGCTGCCTACAATGTGTATGAGGCTGTGTATGCTGTGGCCCACGGC
CTCCACCAGCTCCTGGGATGTACCTCTGGGACCTGTGCCAGAGGCCCAGTCTACCCCTGGCAGCTTCTTCAGCAGATCTA
CAAGGTGAATTTCCTTCTACATAAGAAGACTGTAGCATTCGATGACAAGGGGGACCCTCTAGGTTATTATGACATCATCG
CCTGGGACTGGAATGGACCTGAATGGACCTTTGAGGTCATTGGTTCTGCCTCACTGTCTCCAGTTCATCTAGACATAAAT
```

SEQUENCE TABLE-continued

Example T1Rx Nucleic Acids And Polypeptides

```
AAGACAAAAATCCAGTGGCACGGGAAGAACAATCAGGTGCCTGTGTCAGTGTGTACCAGGGACTGTCTCGAAGGGCACCA

CAGGTTGGTCATGGGTTCCCACCACTGCTGCTTCGAGTGCATGCCCTGTGAAGCTGGGACATTTCTCAACACGAGTGAGC

TTCACACCTGCCAGCCTTGTGGAACAGAAGAATGGGCCCCTGAGGGGAGCTCAGCCTGCTTCTCACGCACCGTGGAGTTC

TTGGGGTGGCATGAACCCATCTCTTTGGTGCTATTAGCAGCTAACACGCTATTGCTGCTGCTGCTGATTGGGACTGCTGG

CCTGTTTGCCTGGCGTCTTCACACGCCTGTTGTGAGGTCAGCTGGGGGTAGGCTGTGCTTCCTCATGCTGGGTTCCTTGG

TAGCTGGGAGTTGCAGCCTCTACAGCTTCTTCGGGAAGCCCACGGTGCCCGCGTGCTTGCTGCGTCAGCCCCTCTTTTCT

CTCGGGTTTGCCATTTTCCTCTCCTGTCTGACAATCCGCTCCTTCCAACTGGTCATCATCTTCAAGTTTTGTACCAAGGT

ACCCACATTCTACCACACTTGGGCCCAAAACCATGGTGCCGGAATATTCGTCATTGTCAGCTCCACGGTCCATTTGTTCC

TCTGTCTCACGTGGCTTGCAATGTGGACCCCACGGCCCACCAGGGAGTACCAGCGCTTCCCCATCTGGTGATTCTTGAG

TGCACAGAGGTCAACTCTGTGGGCTTCCTGGTGGCTTTCGCACACAACATCCTCCTCTCCATCAGCACCTTTGTCTGCAG

CTACCTGGGTAAGGAACTGCCGGAGAACTATAACGAAGCAAATGTGTCACCTTCAGCCTGCTCCTCCACTTCGTATCCT

GGATCGCTTTCTTCACCATGTCCAGCATTTACCAGGGCAGCTACCTACCCGCGGTCAATGTGCTGGCAGGGCTGGCCACT

CTGAGTGGCGGCTTCAGCGGCTATTTCCTCCCTAAATGCTACGTGATTCTCTGCCGTCCAGAACTCAACAACACAGAACA

CTTTCAGGCCTCCATCCAGGACTACACGAGGCGCTGCGGCACTACCTGA
```

>mT1R1                                                    (Amino Acid; SEQ ID NO: 2)
MLFWAAHLLLSLQLAVAYCWAFSCQRTESSPGFSLPGDFLLAGLFSLHADCLQVRHRPLVTSCDRSDSFNGHGYHLFQAM

RFTVEEINNSTALLPNITLGYELTDVCSESSNVYATLRVPAQQGTGHLEMQRDLRNHSSKVVALIGPDNTDHAVTTAALL

SPFLMPLVSYEASSVILSGKRKFPSFLRTIPSDKYQVEVIVRLLQSFGWVWISLVGSYGDYGQLGVQALEELATPRGICV

AFKDVVPLSAQAGDPRMQRMMLRLARARTTVVVVFSNRHLAGVFFRSVVLANLTGKVWIASEDWAISTYITNVPGIQGIG

TVLGVAIQQRQVPGLKEFEESYVQAVMGAPRTCPEGSWCGTNQLCRECHAFTTWNMPELGAFSMSAAYNVYEAVYAVAHG

LHQLLGCTSGTCARGPVYPWQLLQQIYKVNFLLHKKTVAFDDKGDPLGYYDIIAWDWNGPEWTFEVIGSASLSPVHLDIN

KTKIQWHGKNNQVPVSVCTRDCLEGHHRLVMGSHHCCFECMPCEAGTFLNTSELHTCQPCGTEEWAPEGSSACFSRTVEF

LGWHEPISLVLLAANTLLLLLLIGTAGLFAWRLHTPVVRSAGGRLCFLMLGSLVAGSCSLYSFFGKPTVPACLLRQPLFS

LGFAIFLSCLTIRSFQLVIIFKFSTKVPTFYHTWAQNHGAGIFVIVSSTVHLFLCLTWLAMWTPRPTREYQRFPHLVILE

CTEVNSVGFLVAFAHNILLSISTFVCSYLGKELPENYNEAKCVTFSLLLHFVSWIAFFTMSSIYQGSYLPAVNVLAGLAT

LSGGFSGYFLPKCYVILCRPELNNTEHFQASIQDYTRRCGTT.

>mT1R2                                                    (Nucleic Acid; SEQ ID NO: 14)
ATGCTGCGCACTGTGCCCAGCGCCACCCACCACATCGAGGCCATGGTGCAACTGATGGTTCACTTCCAGTGGAACTGGAT

CGTGGTGCTGGTGAGCGATGACGATTATGGCCGAGAGAACAGCCACCTGCTGAGCCAGCGTCTGACCAACACTGGCGATA

TCTGCATTGCCTTCCAGGAGGTTCTGCCTGTACCAGAACCCAACCAGGCCGTGAGGCCTGAGGAGCAGGACCAACTGGAC

AACATCCTGGACAAGCTGCGGCGGACCTCGGCGCGTGTGGTGGTGATATTCTCGCCAGAGCTGAGCCTGCACAACTTCTT

CCGCGAGGTGCTGCGCTGGAACTTCACAGGCTTTGTGTGGATTGCCTCTGAGTCCTGGGCCATCGACCCTGTTCTACACA

ACCTCACAGAGCTGCGCCACACGGGCACTTTCCTGGGCGTCACCATCCAGAGGGTGTCCATCCCTGGCTTCAGCCAGTTC

CGAGTGCGCCACGACAAGCCAGAGTATCCCATGCCTAACGAGACCAGCCTGAGGACTACCTGTAACCAGGACTGTGACGC

CTGCATGAACATCACCGAGTCCTTTAACAACGTTCTCATGCTTTCGGGGAGCGTGGTCTACAGTGTGTACTCGGCCG

TCTACGCGGTAGCCCACACCCTCCACAGACTCCTCCACTGCAACCAGGTCCGCTGCACCAAGCAAATCGTCTATCCATGG

CAGCTACTCAGGGAGATCTGGCATGTCAACTTCACGCTCCTGGGCAACCAGCTCTTCTTCGACGAACAAGGGGACATGCC

GATGCTCCTGGACATCATCCAGTGGCAATGGGGCCTGAGCCAGAACCCCTTCCAAAGCATCGCCTCCTACTCCCCCACCG

AGACGAGGCTGACCTACATTAGCAATGTGTCCTGGTACACCCCCAACAACACGGTCCCCATATCCATGTGTTCTAAGAGT

TGCCAGCCTGGGCAAATGAAAAAACCCATAGGCCTCCACCCGTGCTGCTTCGAGTGTGTGGACTGTCCGCCGGGCACCTA

SEQUENCE TABLE-continued

Example T1Rx Nucleic Acids And Polypeptides

CCTCAACCGATCAGTAGATGAGTTTAACTGTCTGTCCTGCCCGGGTTCCATGTGGTCTTACAAGAACAACATCGCTTGCT

TCAAGCGGCGGCTGGCCTTCCTGGAGTGGCACGAAGTGCCCACTATCGTGGTGACCATCCTGGCCGCCCTGGGCTTCATC

AGTACGCTGGCCATTCTGCTCATCTTCTGGAGACATTTCCAGACGCCCATGGTGCGCTCGGCGGGCGGCCCCATGTGCTT

CCTGATGCTGGTGCCCCTGCTGCTGGCGTTCGGGATGGTCCCCGTGTATGTGGGCCCCCCCACGGTCTTCTCCTGTTTCT

GCCGCCAGGCTTTCTTCACCGTTTGCTTCTCCGTCTGCCTCTCCTGCATCACGGTGCGCTCCTTCCAGATTGTGTGCGTC

TTCAAGATGGCCAGACGCCTGCCAAGCGCCTACGGTTTCTGGATGCGTTACCACGGGCCCTACGTCTTTGTGGCCTTCAT

CACGGCCGTCAAGGTGGCCCTGGTGGCAGGCAACATGCTGGCCACCACCATCAACCCCATTGGCCGGACCGACCCCGATG

ACCCCAATATCATAATCCTCTCCTGCCACCCTAACTACCGCAACGGGCTACTCTTCAACACCAGCATGGACTTGCTGCTG

TCCGTGCTGGGTTTCAGCTTCGCGTACGTGGGCAAGGAACTGCCCACCAACTACAACGAAGCCAAGTTCATCACCCTCAG

CATGACCTTCTCCTTCACCTCCTCCATCTCCCTCTGCACGTTCATGTCTGTCCACGATGGCGTGCTGGTCACCATCATGG

ATCTCCTGGTCACTGTGCTCAACTTTCTGGCCATCGGCTTGGGGTACTTTGGCCCCAAGTGTTACATGATCCTTTTCTAC

CCGGAGCGCAACACTTCAGCTTATTTCAATAGCATGATTCAGGGCTACACGATGAGGAAGAGCTAG

>mT1R2                                                    (amino acid; SEQ ID NO: 5)
MLRTVPSATHHIEAMVQLMVHFQWNWIVVLVSDDDYGRENSHLLSQRLTNTGDICIAFQEVLPVPEPNQAVRPEEQDQLD

NILDKLRRTSAFVVVIFSPELSLHNFFREVLRWNFTGFVWIASESWAIDPVLHNLTELRHTGTFLGVTIQRVSIPGFSQF

RVRHDKPEYPMPNETSLRTTCNQDCDACMNITESFNNVLMLSGERVVYSVYSAVYAVAHTLHRLLHCNQVRCTKQIVYPW

QLLREIWHVNFTLLGNQLFFDEQGDMPMLLDIIQWQWGLSQNPFQSIASYSPTETRLTYISNVSWYTPNNTVPISMCSKS

CQPGQMKKPIGLHPCCFECVDCPPGTYLNRSVDEFNCLSCPGSMWSYKNNIACFKRRLAFLEWHEVPTIVVTILAALGFI

STLAILLIFWRHFQTPMVRSAGGPMCFLMLVPLLLAFGMVPVYVGPPTVFSCFCRQAFFTVCFSVCLSCITVRSFQIVCV

FKMARRLPSAYGFWMRYHGPYVFVAFITAVKVALVAGNMLATTINPIGRTDPDDPNIIILSCHPNYRNGSSFNTSMDLLL

SVLGFSFAYVGKELPTNYNEAKFITLSMTFSFTSSISLCTFMSVHDGVLVTIMDLLVTVLNFLAIGLGYFGPKCYMILFY

PERNTSAYFNSMIQGYTMRKS.

>mT1R3                                                    (nucleic acid; SEQ ID NO: 15)
ATGCCAGCTTTGGCTATCATGGGTCTCAGCCTGGCTGCTTTCCTGGAGCTTGGGATGGGGGCCTCTTTGTGTCTGTCACA

GCAATTCAAGGCACAAGGGGACTACATACTGGGCGGGCTATTTCCCCTGGGCTCAACCGAGGAGGCCACTCTCAACCAGA

GAACACAACCCAACAGCATCCCGTGCAACAGGTTCTCACCCCTTGGTTTGTTCCTGGCCATGGCTATGAAGATGGCTGTG

GAGGAGATCAACAATGGATCTGCCTTGCTCCCTGGGCTGCGGCTGGGCTATGACCTATTTGACACATGCTCCGAGCCAGT

GGTCACCATGAAATCCAGTCTCATGTTCCTGGCCAAGGTGGGCAGTCAAAGCATTGCTGCCTACTGCAACTACACACAGT

ACCAACCCCGTGTGCTGGCTGTCATCGGCCCCCACTCATCAGAGCTTGCCCTCATTACAGGCAAGTTCTTCAGCTTCTTC

CTCATGCCACAGGTCAGCTATAGTGCCAGCATGGATCGGCTAAGTGACCGGGAAACGTTTCCATCCTTCTTCCGCACAGT

GCCCAGTGACCGGGTGCAGCTGCAGGCAGTTGTGACTCTGTTGCAGAACTTCAGCTGGAACTGGGTGGCCGCCTTAGGGA

GTGATGATGACTATGGCCGGGAAGGTCTGAGCATCTTTTCTAGTCTGGCCAATGCACGAGGTATCTGCATCGCACATGAG

GGCCTGGTGCCACAACATGACACTAGTGCCAACAGTTGGGCAAGGTGCTGGATGTACTACGCCAAGTGAACCAAAGTAA

AGTACAAGTGGTGGTGCTGTTTGCCTCTGCCCGTGCTGTCTACTCCCTTTTTAGTTACAGCATCCATCATGGCCTCTCAC

CCAAGGTATGGGTGGCCAGTGAGTCTTGGCTGACATCTGACCTGGTCATGACACTTCCCAATATTGCCCGTGTGGGCACT

GTGCTTGGGTTTTTGCAGCGGGGTGCCCTACTGCCTGAATTTTCCCATTATGTGGAGACTCACCTTGCCCTGGCCGCTGA

CCCAGCATTCTGTGCCTCACTGAATGCGGAGTTGGATCTGGAGGAACATGTGATGGGGCAACGCTGTCCACGGTGTGACG

ACATCATGCTGCAGAACCTATCATCTGGGCTGTTGCAGAACCTATCAGCTGGGCAATTGCACCACCAAATATTTGCAACC

TATGCAGCTGTGTACAGTGTGGCTCAAGCCCTTCACAACACCCTACAGTGCAATGTCTCACATTGCCACGTATCAGAACA

SEQUENCE TABLE-continued

Example T1Rx Nucleic Acids And Polypeptides

TGTTCTACCCTGGCAGCTCCTGGAGAACATGTACAATATGAGTTTCCATGCTCGAGACTTGACACTACAGTTTGATGCTG

AAGGGAATGTAGACATGGAATATGACCTGAAGATGTGGGTGTGGCAGAGCCCTACACCTGTATTACATACTGTGGGCACC

TTCAACGGCACCCTTCAGCTGCAGCAGTCTAAAATGTACTGGCCAGGCAACCAGGTGCCAGTCTCCCAGTGTTCCCGCCA

GTGCAAAGATGGCCAGGTTCGCCGAGTAAAGGGCTTTCATTCCTGCTGCTATGACTGCGTGGACTGCAAGGCGGGCAGCT

ACCGGAAGCATCCAGATGACTTCACCTGTACTCCATGTAACCAGGACCAGTGGTCCCCAGAGAAAAGCACAGCCTGCTTA

CCTCGCAGGCCCAAGTTTCTGGCTTGGGGGGAGCCAGTTGTGCTGTCACTCCTCCTGCTGCTTTGCCTGGTGCTGGGTCT

AGCACTGGCTGCTCGGGGCTCTCTGTCCACCACTGGGACAGCCCTCTTGTCCAGGCCTCAGGTGGCTCACAGTTCTGCT

TTGGCCTGATCTGCCTAGGCCTCTTCTGCCTCAGTGTCCTTCTGTTCCCAGGGCGGCCAAGCTCTGCCAGCTGCCTTGCA

CAACAACCAATGGCTCACCTCCCTCTCACAGGCTGCCTGAGCACACTCTTCCTGCAAGCAGCTGAGACCTTTGTGGAGTC

TGAGCTGCCACTGAGCTGGGCAAACTGGCTATGCAGCTACCTTCGGGGACTCTGGGCCTGGCTAGTGGTACTGTTGGCCA

CTTTTGTGGAGGCAGCACTATGTGCCTGGTATTTGATCGCTTTCCCACCAGAGGTGGTGACAGACTGGTCAGTGCTGCCC

ACAGAGGTACTGGAGCACTGCCACGTGCGTTCCTGGGTCAGCCTGGGCTTGGTGCACATCACCAATGCAATGTTAGCTTT

CCTCTGCTTTCTGGGCACTTTCCTGGTACAGAGCCAGCCTGGCCGCTACAACCGTGCCCGTGGTCTCACCTTCGCCATGC

TAGCTTATTTCATCACCTGGGTCTCTTTTGTGCCCCTCCTGGCCAATGTGCAGGTGGCCTACCAGCCAGCTGTGCAGATG

GGTGCTATCCTAGTCTGTGCCCTGGGCATCCTGGTCACCTTCCACCTGCCCAAGTGCTATGTGCTTCTTTGGCTGCCAAA

GCTCAACACCCAGGAGTTCTTCCTGGGAAGGAATGCCAAGAAAGCAGCAGATGAGAACAGTGGCGGTGGTGAGGCAGCTC

AGGGACACAATGAATGA

>mT1R3                                                          (amino acid; SEQ ID NO: 8)
MPALAIMGLSLAAFLELGMGASLCLSQQFKAQGDYILGGLFPLGSTEEATLNQRTQPNSIPCNRFSPLGLFLAMAMKMAV

EEINNGSALLPGLRLGYDLFDTCSEPVVTMKSSLMFLAKVGSQSIAAYCNYTQYQPRVLAVIGPHSSELALITGKFFSFF

LMPQVSYSASMDRLSDRETFPSFFRTVPSDRVQLQAVVTLLQNFSWNWVAALGSDDDYGREGLSIFSSLANARGICIAHE

GLVPQHDTSGQQLGKVLDVLRQVNQSKVQVVVLFASARAVYSLFSYSIHHGLSPKVWVASESWLTSDLVMTLPNIARVGT

VLGFLQRGALLPEFSHYVETHLALAADPAFCASLNAELDLEEHVMGQRCPRCDDIMLQNLSSGLLQNLSAGQLHHQIFAT

YAAVYSVAQALHNTLQCNVSHCHVSEHVLPWQLLENMYNMSFHARDLTLQFDAEGNVDMEYDLKMWVWQSPTPVLHTVGT

FNGTLQLQQSKMYWPGNQVPVSQCSRQCKDGQVRRVKGFHSCCYDCVDCKAGSYRKHPDDFTCTPCNQDQWSPEKSTACL

PRRPKFLAWGEPVVLSLLLLLCLVLGLALAALGLSVHHWDSPLVQASGGSQFCFGLICLGLFCLSVLLFPGRPSSASCLA

QQPMAHLPLTGCLSTLFLQAAETFVESELPLSWANWMCSYLRGLWAWLVVLLATFVEAALCAWYLIAFPPEVVTDWSVLP

TEVLEHCVRSWVSLGLVHITNAMLAFLCFLGTFLVQAQPGRYNRARGLTFAMLAYFITWVSFVPLLANVQVAYQPAVQM

GAILVCALGILVTFHLPKCYVLLWLPKLNTQEFFLGRNAKKAADENSGGGEAAQGHNE.

>rT1R1                                                          (nucleic acid; SEQ ID NO: 16)
ATGCTCTTCTGGGCTGCTCACCTGCTGCTCAGCCTGCAGTTGGTCTACTGCTGGGCTTTCAGCTGCCAAAGGACAGAGTC

CTCTCCAGGCTTCAGCCTTCCTGGGGACTTCCTCCTTGCAGGTCTGTTCTCCCTCCATGGTGACTGTCTGCAGGTGAGAC

ACAGACCTCTGGTGACAAGTTGTGACAGGCCCGACAGCTTCAACGGCCATGGCTACCACCTCTTCCAAGCCATGCGGTTC

ACTGTTGAGGAGATAAACAACTCCTCGGCCCTGCTTCCCAACATCACCCTGGGGTATGAGCTGTACGACGTGTGCTCAGA

ATCTGCCAATGTGTATGCCACCCTGAGGGTGCTTGCCCTGCAAGGGCCCCGCCACATAGAGATACAGAAAGACCTTCGCA

ACCACTCCTCCAAGGTGGTGGCCTTCATCGGGCCTGACAACACTGACCACGCTGTCACTACCGCTGCCTTGCTGGGTCCT

TTCCTGATGCCCCTGGTCAGCTATGAGGCAAGCAGCGTGGTACTCAGTGCCAAGCGCAAGTTCCCGTCTTTCCTTCGTAC

CGTCCCCAGTGACCGGCACCAGGTGGAGGTCATGGTGCAGCTGCTGCAGAGTTTTGGGTGGGTGTGGATCTCGCTCATTG

GCAGCTACGGTGATTACGGCAGCTGGGTGTGCAGGCGCTGGAGGAGCTGGCCGTGCCCCGGGGCATCTGCGTCGCCTTC

AAGGACATCGTGCCTTTCTCTGCCCGGGTGGGTGACCCGAGGATGCAGAGCATGATGCAGCATCTGGCTCAGGCCAGGAC

SEQUENCE TABLE-continued

Example T1Rx Nucleic Acids And Polypeptides

```
CACCGTGGTTGTGGTCTTCTCTAACCGGCACCTGGCTAGAGTGTTCTTCAGGTCCGTGGTGCTGGCCAACCTGACTGGCA
AAGTGTGGGTCGCCTCAGAAGACTGGGCCATCTCCACGTACATCACCAGCGTGACTGGGATCCAAGGCATTGGGACGGTG
CTCGGTGTGGCCGTCCAGCAGAGACAAGTCCCTGGGCTGAAGGAGTTTGAGGAGTCTTATGTCAGGGCTGTAACAGCTGC
TCCCAGCGCTTGCCCGGAGGGGTCCTGGTGCAGCACTAACCAGCTGTGCCGGGAGTGCCACACGTTCACGACTCGTAACA
TGCCCACGCTTGGAGCCTTCTCCATGAGTGCCGCCTACAGAGTGTATGAGGCTGTGTACGCTGTGGCCCACGGCCTCCAC
CAGCTCCTGGGATGTACTTCTGAGATCTGTTCCAGAGGCCCAGTCTACCCCTGGCAGCTTCTTCAGCAGATCTACAAGGT
GAATTTTCTTCTACATGAGAATACTGTGGCATTTGATGACAACGGGGACACTCTAGGTTACTACGACATCATCGCCTGGG
ACTGGAATGGACCTGAATGGACCTTTGAGATCATTGGCTCTGCCTCACTGTCTCCAGTTCATCTGGACATAAATAAGACA
AAAATCCAGTGGCACGGGAAGAACAATCAGGTGCCTGTGTCAGTGTGTACCACGGACTGTCTGGCAGGGCACCACAGGGT
GGTTGTGGGTTCCCACCACTGCTGCTTTGAGTGTGTGCCCTGCGAAGCTGGGACCTTTCTCAACATGAGTGAGCTTCACA
TCTGCCAGCCTTGTGGAACAGAAGAATGGGCACCCAAGGAGAGCACTACTTGCTTCCCACGCACGGTGGAGTTCTTGGCT
TGGCATGAACCCATCTCTTTGGTGCTAATAGCAGCTAACACGCTATTGCTGCTGCTGGTTGGGACTGCTGGCCTGTT
TGCCTGGCATTTTCACACACCTGTAGTGAGGTCAGCTGGGGGTAGGCTGTGCTTCCTCATGCTGGGTTCCCTGGTGGCCG
GAAGTTGCAGCTTCTATAGCTTCTTCGGGGAGCCCACGGTGCCCGCGTGCTTGCTGCGTCAGCCCCTCTTTTCTCTCGGG
TTTGCCATCTTCCTCTCCTGCCTGACAATCCGCTCCTTCCAACTGGTCATCATCTTCAAGTTTTCTACCAAGGTGCCCAC
ATTCTACCGTACCTGGGCCCAAAACCATGGTGCAGGTCTATTCGTCATTGTCAGCTCCACGGTCCATTTGCTCATCTGTC
TCACATGGCTTGTAATGTGGACCCCACGACCCACCAGGGAATACCAGCGCTTCCCCCATCTGGTGATTCTCGAGTGCACA
GAGGTCAACTCTGTAGGCTTCCTGTTGGCTTTCACCCACAACATTCTCCTCTCCATCAGTACCTTCGTCTGCAGCTACCT
GGGTAAGGAACTGCCAGAGAACTATAATGAAGCCAAATGTGTCACCTTCAGCCTGCTCCTCAACTTCGTATCCTGGATCG
CCTTCTTCACCATGGCCAGCATTTACCAGGGCAGCTACCTGCCTGCGGTCAATGTGCTGGCAGGGCTGACCACACTGAGC
GGCGGCTTCAGCGGTTACTTCCTCCCCAAGTGCTATGTGATTCTCTGCCGTCCAGAACTCAACAATACAGAACACTTTCA
GGCCTCCATCCAGGACTACACGAGGCGCTGCGGCACTACCTGA
```
>rT1R1                                                           (amino acid; SEQ ID NO: 3)
MLFWAAHLLLSLQLVYCWAFSCQRTESSPGFSLPGDFLLAGLFSLHGDCLQVRHRPLVTSCDRPDSFNGHGYHLFQAMRF
TVEEINNSSALLPNITLGYELYDVCSESANVYATLRVLALQGPRHIEIQKDLRNHSSKVVAFIGPDNTDHAVTTAALLGP
FLMPLVSYEASSVVLSAKRKFPSFLRTVPSDRHQVEVMVQLLQSFGWVWISLIGSYGDYGQLGVQALEELAVPRGICVAF
KDIVPFSARVGDPRMQSMMQHLAQARTTVVVVFSNRHLARVFFRSVVLANLTGKVWVASEDWAISTYITSVTGIQGIGTV
LGVAVQQRQVPGLKEFEESYVRAVTAAPSACPEGSWCSTNQLCRECHTFTTRNMPTLGAFSMSAAYRVYEAVYAVAHGLH
QLLGCTSEICSRGPVYPWQLLQQIYKVNFLLHENTVAFDDNGDTLGYYDIIAWDWNGPEWTFEIIGSASLSPVHLDINKT
KIQWHGKNNQVPVSVCTTDCLAGHHRVVVGSHHCCFECVPCEAGTFLNMSELHICQPCGTEEWAPKESTTCFPRTVEFLA
WHEPISLVLIAANTLLLLLLVGTAGLFAWHFHTPVVRSAGGRLCFLMLGSLVAGSCSFYSFFGEPTVPACLLRQPLFSLG
FAIFLSCLTIRSFQLVIIFKFSTKVPTFYRTWAQNHGAGLFVIVSSTVHLLICLTWLVMWTPRPTREYQRFPHLVILECT
EVNSVGFLLAFTHNILLSISTFVCSYLGKELPENYNEAKCVTFSLLLNFVSWIAFFTMASIYQGSYLPAVNVLAGLTTLS
GGFSGYFLPKCYVILCRPELNNTEHFQASIQDYTRRCGTT.
>rT1R2                                                           (Nucleic Acid; SEQ ID NO: 17)
ATGGGTCCCCAGGCAAGGACACTCTGCTTGCTGTCTCCTGCTGCATGTTCTGCCTAAGCCAGGCAAGCTGGTAGAGAA
CTCTGACTTCCACCTGGCCGGGGACTACCTCCTGGGTGGCCTCTTTACCCTCCATGCCAACGTGAAGAGCATCTCCCACC
TCAGCTACCTGCAGGTGCCCAAGTGCAATGAGTTCACCATGAAGGTGTTGGGCTACAACCTCATGCAGGCCATGCGTTTC
GCTGTGGAGGAGATCAACAACTGTAGCTCCCTGCTACCCGGCGTGCTGCTCGGCTACGAGATGGTGGATGTCTGTTACCT
```

SEQUENCE TABLE-continued

Example T1Rx Nucleic Acids And Polypeptides

CTCCAACAATATCCACCCTGGGCTCTACTTCCTGGCACAGGACGACGACCTCCTGCCCATCCTCAAAGACTACAGCCAGT

ACATGCCCCACGTGGTGGCTGTCATTGGCCCCGACAACTCTGAGTCCGCCATTACCGTGTCCAACATTCTCTCTCATTTC

CTCATCCCACAGATCACATACAGCGCCATCTCCGACAAGCTGCGGGACAAGCGGCACTTCCCTAGCATGCTACGCACAGT

GCCCAGCGCCACCCACCACATCGAGGCCATGGTGCAGCTGATGGTTCACTTCCAATGGAACTGGATTGTGGTGCTGGTGA

GCGACGACGATTACGGCCGCGAGAACAGCCACCTGTTGAGCCAGCGTCTGACCAAAACGAGCGACATCTGCATTGCCTTC

CAGGAGGTTCTGCCCATACCTGAGTCCAGCCAGGTCATGAGGTCCGAGGAGCAGAGACAACTGGACAACATCCTGGACAA

GCTGCGGCGGACCTCGGCGCGCGTCGTGGTGGTGTTCTCGCCCGAGCTGAGCCTGTATAGCTTCTTTCACGAGGTGCTCC

GCTGGAACTTCACGGGTTTTGTGTGGATCGCCTCTGAGTCCTGGGCTATCGACCCAGTTCTGCATAACCTCACGGAGCTG

CGCCACACGGGTACTTTTCTGGGCGTCACCATCCAGAGGGTGTCCATCCCTGGCTTCAGTCAGTTCCGAGTGCGCCGTGA

CAAGCCAGGGTATCCCGTGCCTAACACGACCAACCTGCGGACGACCTGCAACCAGGACTGTGACGCCTGCTTGAACACCA

CCAAGTCCTTCAACAACATCCTTATACTTTCGGGGGAGCGCGTGGTCTACAGCGTGTACTCGGCAGTTTACGCGGTGGCC

CATGCCCTCCACAGACTCCTCGGCTGTAACCGGGTCCGCTGCACCAAGCAAAAGGTCTACCCGTGGCAGCTACTCAGGGA

GATCTGGCACGTCAACTTCACGCTCCTGGGTAACCGGCTCTTCTTTGACCAACAAGGGGACATGCCGATGCTCTTGGACA

TCATCCAGTGGCAGTGGGACCTGAGCCAGAATCCCTTCCAAAGCATCGCCTCCTATTCTCCCACCAGCAAGAGGCTAACC

TACATTAACAATGTGTCCTGGTACACCCCCAACAACACGGTCCCTGTCTCCATGTGTTCCAAGAGCTGCCAGCCAGGGCA

AATGAAAAAGTCTGTGGGCCTCCACCCTTGTTGCTTCGAGTGCTTGGATTGTATGCCAGGCACCTACCTCAACCGCTCAG

CAGATGAGTTTAACTGTCTGTCCTGCCCGGGTTCCATGTGGTCCTACAAGAACGACATCACTTGCTTCCAGCGGCGGCCT

ACCTTCCTGGAGTGGCACGAAGTGCCCACCATCGTGGTGGCCATACTGGCTGCCCTGGGCTTCTTCAGTACACTGGCCAT

TCTTTTCATCTTCTGGAGACATTTCCAGACACCCATGGTGCGCTCGGCCGGTGGCCCCATGTGCTTCCTGATGCTCGTGC

CCCTGCTGCTGGCGTTTGGGATGGTGCCCGTGTATGTGGGGCCCCCCACGGTCTTCTCATGCTTCTGCCGACAGGCTTTC

TTCACCGTCTGCTTCTCCATCTGCCTATCCTGCATCACCGTGCGCTCCTTCCAGATCGTGTGTGTCTTCAAGATGGCCAG

ACGCCTGCCAAGTGCCTACAGTTTTTGGATGCGTTACCACGGGCCCTATGTCTTCGTGGCCTTCATCACGGCCATCAAGG

TGGCCCTGGTGGTGGGCAACATGCTGGCCACCACCATCAACCCCATTGGCCGGACCGACCCGGATGACCCCAACATCATG

ATCCTCTCGTGCCACCCTAACTACCGCAACGGGCTACTGTTCAACACCAGCATGGACTTGCTGCTGTCTGTGCTGGGTTT

CAGCTTCGCTTACATGGGCAAGGAGCTGCCCACCAACTACAACGAAGCCAAGTTCATCACTCTCAGCATGACCTTCTCCT

TCACCTCCTCCATCTCCCTCTGCACCTTCATGTCTGTGCACGACGGCGTGCTGGTCACCATCATGGACCTCCTGGTCACT

GTGCTCAACTTCCTGGCCATCGGCTTGGGATACTTTGGCCCCAAGTGTTACATGATCCTTTTCTACCCGGAGCGCAACAC

CTCAGCCTATTTCAATAGCATGATCCAGGGCTACACCATGAGGAAGAGC

>rT1R2                                                              (Amino Acid; SEQ ID NO: 6)
MGPQARTLCLLSLLLHVLPKPGKLVENSDFHLAGDYLLGGLFTLHANVKSISHLSYLQVPKCNEFTMKVLGYNLMQAMRF

AVEEINNCSSLLPGVLLGYEMVDVCYLSNNIHPGLYFLAQDDDLLPILKDYSQYMPHVVAVIGPDNSESAITVSNILSHF

LIPQITYSAISDKLRDKRHFPSMLRTVPSATHHIEAMVQLMVHFQWNWIVVLVSDDDYGRENSHLLSQRLTKTSDICIAF

QEVLPIPESSQVMRSEEQRQLDNILDKLRRTSARVVVVFSPELSLYSFFHEVLRWNFTGFVWIASESWAIDPVLHNLTEL

RHTGTFLGVTIQRVSIPGFSQFRVRRDKPGYPVPNTTNLRTTCNQDCDACLNTTKSFNNILILSGERVVYSVYSAVYAVA

HALHRLLGCNRVRCTKQKVYPWQLLREIWHVNFTLLGNRLFFDQQGDMPMLLDIIQWQWDLSQNPFQSIASYSPTSKRLT

YINNVSWYTPNNTVPVSMCSKSCQPGQMKKSVGLHPCCFECLDCMPGTYLNRSADEFNCLSCPGSMWSYKNDITCFQRRP

TFLEWHEVPTIVVAILAALGFFSTLAILFIFWRHFQTPMVRSAGGPMCFLMLVPLLLAFGMVPVYVGPPTVFSCFCRQAF

FTVCFSICLSCITVRSFQIVCVFKMARRLPSAYSFWMRYHGPYVFVAFITAIKVALVVGNMLATTINPIGRTDPDDPNIM

ILSCHPNYRNGLLFNTSMDLLLSVLGFSFAYMGKELPTNYNEAKFITLSMTFSFTSSISLCTFMSVHDGVLVTIMDLLVT

SEQUENCE TABLE-continued

Example T1Rx Nucleic Acids And Polypeptides

VLNFLAIGLGYFGPKCYMILFYPERNTSAYFNSMIQGYTMRKS

>rT1R3 (Nucleic Acid; SEQ ID NO: 18)
ATGCCGGGTTTGGCTATCTTGGGCCTCAGTCTGGCTGCTTTCCTGGAGCTTGGGATGGGGTCCTCTTTGTGTCTGTCACA
GCAATTCAAGGCACAAGGGGACTATATATTGGGTGGACTATTTCCCCTGGGCACAACTGAGGAGGCCACTCTCAACCAGA
GAACACAGCCCAACGGCATCCTATGTACCAGGTTCTCGCCCCTTGGTTTGTTCCTGGCCATGGCTATGAAGATGGCTGTA
GAGGAGATCAACAATGGATCTGCCTTGCTCCCTGGGCTGCGACTGGGCTATGACCTGTTTGACACATGCTCAGAGCCAGT
GGTCACCATGAAGCCCAGCCTCATGTTCATGGCCAAGGTGGGAAGTCAAAGCATTGCTGCCTACTGCAACTACACACAGT
ACCAACCCCGTGTGCTGGCTGTCATTGGTCCCCACTCATCAGAGCTTGCCCTCATTACAGGCAAGTTCTTCAGCTTCTTC
CTCATGCCACAGGTCAGCTATAGTGCCAGCATGGATCGGCTAAGTGACCGGGAAACATTTCCATCCTTCTTCCGCACAGT
GCCCAGTGACCGGGTGCAGCTGCAGGCCGTTGTGACACTGTTGCAGAATTTCAGCTGGAACTGGGTGGCTGCCTTAGGTA
GTGATGATGACTATGGCCGGGAAGGTCTGAGCATCTTTTCTGGTCTGGCCAACTCACGAGGTATCTGCATTGCACACGAG
GGCCTGGTGCCACAACATGACACTAGTGGCCAACAATTGGGCAAGGTGGTGGATGTGCTACGCCAAGTGAACCAAAGCAA
AGTACAGGTGGTGGTGCTGTTTGCATCTGCCCGTGCTGTCTACTCCCTTTTTAGCTACAGCATCCTTCATGACCTCTCAC
CCAAGGTATGGGTGGCCAGTGAGTCCTGGCTGACCTCTGACCTGGTCATGACACTTCCCAATATTGCCCGTGTGGGCACT
GTTCTTGGGTTTCTGCAGCGCGGTGCCCTACTGCCTGAATTTTCCCATTATGTGGAGACTCGCCTTGCCCTAGCTGCTGA
CCCAACATTCTGTGCCTCCCTGAAAGCTGAGTTGGATCTGGAGGAGCGCGTGATGGGCCACGCTGTTCACAATGTGACT
ACATCATGCTACAGAACCTGTCATCTGGGCTGATGCAGAACCTATCAGCTGGGCAGTTGCACCACCAAATATTTGCAACC
TATGCAGCTGTGTACAGTGTGGCTCAGGCCCTTCACAACACCCTGCAGTGCAATGTCTCACATTGCCACACATCAGAGCC
TGTTCAACCCTGGCAGCTCCTGGAGAACATGTACAATATGAGTTTCCGTGCTCGAGACTTGACACTGCAGTTTGATGCCA
AAGGGAGTGTAGACATGGAATATGACCTGAAGATGTGGGTGTGGCAGAGCCCTACACCTGTACTACATACTGTAGGCACC
TTCAACGGCACCCTTCAGCTGCAGCACTCGAAAATGTATTGGCCAGGCAACCAGGTGCCAGTCTCCCAGTGCTCCCGGCA
GTGCAAAGATGGCCAGGTGCGCAGAGTAAAGGGCTTTCATTCCTGCTGCTATGACTGTGTGGACTGCAAGGCAGGGAGCT
ACCGGAAGCATCCAGATGACTTCACCTGTACTCCATGTGGCAAGGATCAGTGGTCCCCAGAAAAAAGCACAACCTGCTTA
CCTCGCAGGCCCAAGTTTCTGGCTTGGGGGAGCCAGCTGTGCTGTCACTTCTCCTGCTGCTTTGCCTGGTGCTGGGCCT
GACACTGGCTGCCCTGGGGCTCTTTGTCCACTACTGGGACAGCCCTCTTGTTCAGGCCTCAGGTGGGTCACTGTTCTGCT
TTGGCCTGATCTGCCTAGGCCTCTTCTGCCTCAGTGTCCTTCTGTTCCCAGGACGACCACGCTCTGCCAGCTGCCTTGCC
CAACAACCAATGGCTCACCTCCCTCTCACAGGCTGCCTGAGCACACTCTTCCTGCAAGCAGCCGAGATCTTTGTGGAGTC
TGAGCTGCCACTGAGTTGGGCAAACTGGCTCTGCAGCTACCTTCGGGGCCCCTGGGCTTGGCTGGTGGTACTGCTGGCCA
CTCTTGTGGAGGCTGCACTATGTGCCTGGTACTTGATGGCTTTCCCTCCAGAGGTGGTGACAGATTGGCAGGTGCTGCCC
ACGGAGGTACTGGAACACTGCCGCATGCGTTCCTGGGTCAGCCTGGGCTTGGTGCACATCACCAATGCAGTGTTAGCTTT
CCTCTGCTTTCTGGGCACTTTCCTGGTACAGAGCCAGCCTGGTCGCTATAACCGTGCCCGTGGCCTCACCTTCGCCATGC
TAGCTTATTTCATCATCTGGGTCTCTTTTGTGCCCCTCCTGGCTAATGTGCAGGTGGCCTACCAGCCAGCTGTGCAGATG
GGTGCTATCTTATTCTGTGCCCTGGGCATCCTGGCCACCTTCCACCTGCCCAAATGCTATGTACTTCTGTGGCTGCCAGA
GCTCAACACCCAGGAGTTCTTCCTGGGAAGGAGCCCCAAGGAAGCATCAGATGGGAATAGTGGTAGTAGTGAGGCAACTC
GGGGACACAGTGAATGA >rT1R3 (Amino Acid; SEQ ID NO: 9)
MPGLAILGLSLAAFLELGMGSSLCLSQQFKAQGDYILGGLFPLGTTEEATLNQRTQPNGILCTRFSPLGLFLAMAMKMAV
EEINNGSALLPGLRLGYDLFDTCSEPVVTMKPSLMFMAKVGSQSIAAYCNYTQYQPRVLAVIGPHSSELALITGKFFSFF
LMPQVSYSASMDRLSDRETFPSFFRTVPSDRVQLAVVTLLQNFSWNWVAALGSDDDYGREGLSIFSGLANSRGICIAHE
GLVPQHDTSGQQLGKVVDVLRQVNQSKVQVVVLFASARAVYSLFSYSILHDLSPKVWVASESWLTSDLVMTLPNIARVGT SEQUENCE TABLE-continued Example T1Rx Nucleic Acids And Polypeptides

VLGFLQRGALLPEFSHYVETRLALAADPTFCASLKAELDLEERVMGPRCSQCDYIMLQNLSSGLMQNLSAGQLHHQIFAT

YAAVYSVAQALHNTLQCNVSHCHTSEPVQPWQLLENMYNMSFRARDLTLQFDAKGSVDMEYDLKMWVWQSPTPVLHTVGT

FNGTLQLQHSKMYWPGNQVPVSQCSRQCKDGQVRRVKGFHSCCYDCVDCKAGSYRKHPDDFTCTPCGKDQWSPEKSTTCL

PRRPKFLAWGEPAVLSLLLLLCLVLGLTLAALGLFVHYWDSPLVQASGGSLFCFGLICLGLFCLSVLLFPGRPRSASCLA

QQPMAHLPLTGCLSTLFLQAAEIFVESELPLSWANWLCSYLRGPWAWLVVLLATLVEAALCAWYLMAFPPEVVTDWQVLP

TEVLEHCRMRSWVSLGLVHITNAVLAFLCFLGTFLVQSQPGRYNRARGLTFAMLAYFIIWVSFVPLLANVQVAYQPAVQM

GAILFCALGILATFHLPKCYVLLWLPELNTQEFFLGRSPKEASDGNSGSSEATRGHSE.

SEQUENCE LISTING

<160> NUMBER OF SEQ ID NOS: 22

<210> SEQ ID NO 1
<211> LENGTH: 840
<212> TYPE: PRT
<213> ORGANISM: Homo sapiens

<400> SEQUENCE: 1

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
                20                  25                  30

Thr Leu Pro Gly Asp Tyr Leu Leu Ala Gly Leu Phe Pro Leu His Ser
            35                  40                  45

Gly Cys Leu Gln Val Arg His Arg Pro Glu Val Thr Leu Cys Asp Arg
        50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Leu Ile Ser Tyr Ala Ala Ser Ser Glu Thr
                165                 170                 175

Leu Ser Val Lys Arg Gln Tyr Pro Ser Phe Leu Arg Thr Ile Pro Asn
            180                 185                 190

Asp Lys Tyr Gln Val Glu Thr Met Val Leu Leu Gln Lys Phe Gly
        195                 200                 205

Trp Thr Trp Ile Ser Leu Val Gly Ser Ser Asp Asp Tyr Gly Gln Leu
    210                 215                 220

Gly Val Gln Ala Leu Glu Asn Gln Ala Thr Gly Gln Gly Ile Cys Ile
225                 230                 235                 240

-continued

```
Ala Phe Lys Asp Ile Met Pro Phe Ser Ala Gln Val Gly Asp Glu Arg
                245                 250                 255
Met Gln Cys Leu Met Arg His Leu Ala Gln Ala Gly Ala Thr Val Val
            260                 265                 270
Val Val Phe Ser Ser Arg Gln Leu Ala Arg Val Phe Glu Ser Val
        275                 280                 285
Val Leu Thr Asn Leu Thr Gly Lys Val Trp Val Ala Ser Glu Ala Trp
    290                 295                 300
Ala Leu Ser Arg His Ile Thr Gly Val Pro Gly Ile Gln Arg Ile Gly
305                 310                 315                 320
Met Val Leu Gly Val Ala Ile Gln Lys Arg Ala Val Pro Gly Leu Lys
                325                 330                 335
Ala Phe Glu Glu Ala Tyr Ala Arg Ala Asp Lys Glu Ala Pro Arg Pro
            340                 345                 350
Cys His Lys Gly Ser Trp Cys Ser Ser Asn Gln Leu Cys Arg Glu Cys
        355                 360                 365
Gln Ala Phe Met Ala His Thr Met Pro Lys Leu Lys Ala Phe Ser Met
    370                 375                 380
Ser Ser Ala Tyr Asn Ala Tyr Arg Ala Val Tyr Ala Val Ala His Gly
385                 390                 395                 400
Leu His Gln Leu Leu Gly Cys Ala Ser Gly Ala Cys Ser Arg Gly Arg
                405                 410                 415
Val Tyr Pro Trp Gln Leu Glu Gln Ile His Lys Val His Phe Leu Leu
            420                 425                 430
His Lys Asp Thr Val Ala Phe Asn Asp Asn Arg Asp Pro Leu Ser Ser
        435                 440                 445
Tyr Asn Ile Ile Ala Trp Asp Trp Asn Gly Pro Lys Trp Thr Phe Thr
    450                 455                 460
Val Leu Gly Ser Ser Thr Trp Ser Pro Val Gln Leu Asn Ile Asn Glu
465                 470                 475                 480
Thr Lys Ile Gln Trp His Gly Lys Asp Asn Gln Glu Pro Ser Leu Cys
                485                 490                 495
Val Pro Ala Thr Val Leu Lys Gly Thr Ser Glu Trp Leu Arg Val Ser
            500                 505                 510
Ile Thr Ala Ala Leu Ser Val Cys Pro Val Gly Gly Ser Trp Pro Ser
        515                 520                 525
Leu Ser Asp Leu Tyr Arg Cys Gln Pro Cys Gly Lys Glu Glu Trp Ala
    530                 535                 540
Pro Glu Gly Ser Gln Thr Cys Phe Pro Arg Thr Val Val Phe Leu Ala
545                 550                 555                 560
Leu Arg Glu His Thr Ser Trp Val Leu Leu Ala Ala Asn Thr Leu Leu
                565                 570                 575
Leu Leu Leu Leu Leu Gly Thr Ala Gly Leu Phe Ala Trp His Leu Asp
            580                 585                 590
Thr Pro Val Val Arg Ser Ala Gly Gly Arg Leu Cys Phe Leu Met Leu
        595                 600                 605
Gly Ser Leu Ala Ala Gly Ser Gly Ser Leu Tyr Gly Phe Phe Gly Glu
    610                 615                 620
Pro Thr Arg Pro Ala Cys Leu Leu Arg Gln Ala Leu Phe Ala Leu Gly
625                 630                 635                 640
Phe Thr Ile Phe Leu Ser Cys Leu Thr Val Arg Ser Phe Gln Leu Ile
                645                 650                 655
Ile Ile Phe Lys Phe Ser Thr Lys Val Pro Thr Phe Tyr His Ala Trp
```

-continued

```
                     660                 665                 670
Val Gln Asn His Gly Ala Gly Leu Phe Val Met Ile Ser Ser Ala Ala
                675                 680                 685

Gln Leu Leu Ile Cys Leu Thr Trp Leu Val Val Trp Thr Pro Leu Pro
            690                 695                 700

Ala Arg Glu Tyr Gln Arg Phe Pro His Leu Val Met Leu Glu Cys Thr
705                 710                 715                 720

Glu Thr Asn Ser Leu Gly Phe Ile Leu Ala Phe Leu Tyr Asn Gly Leu
                725                 730                 735

Leu Ser Ile Ser Ala Phe Ala Cys Ser Tyr Leu Gly Lys Asp Leu Pro
            740                 745                 750

Glu Asn Tyr Asn Glu Ala Lys Cys Val Thr Phe Ser Leu Leu Phe Asn
        755                 760                 765

Phe Val Ser Trp Ile Ala Phe Phe Thr Thr Ala Ser Val Tyr Asp Gly
    770                 775                 780

Lys Tyr Leu Pro Ala Ala Asn Met Met Ala Gly Leu Ser Ser Leu Ser
785                 790                 795                 800

Ser Gly Phe Gly Gly Tyr Phe Leu Pro Lys Cys Tyr Val Ile Leu Cys
                805                 810                 815

Arg Pro Asp Leu Asn Ser Thr Glu His Phe Gln Ala Ser Ile Gln Asp
            820                 825                 830

Tyr Thr Arg Arg Cys Gly Ser Thr
835                 840

<210> SEQ ID NO 2
<211> LENGTH: 842
<212> TYPE: PRT
<213> ORGANISM: Mus musculus

<400> SEQUENCE: 2

Met Leu Phe Trp Ala Ala His Leu Leu Leu Ser Leu Gln Leu Ala Val
1               5                   10                  15

Ala Tyr Cys Trp Ala Phe Ser Cys Gln Arg Thr Glu Ser Ser Pro Gly
                20                  25                  30

Phe Ser Leu Pro Gly Asp Phe Leu Leu Ala Gly Leu Phe Ser Leu His
            35                  40                  45

Ala Asp Cys Leu Gln Val Arg His Arg Pro Leu Val Thr Ser Cys Asp
        50                  55                  60

Arg Ser Asp Ser Phe Asn Gly His Gly Tyr His Leu Phe Gln Ala Met
65                  70                  75                  80

Arg Phe Thr Val Glu Glu Ile Asn Asn Ser Thr Ala Leu Leu Pro Asn
                85                  90                  95

Ile Thr Leu Gly Tyr Glu Leu Tyr Asp Val Cys Ser Glu Ser Ser Asn
            100                 105                 110

Val Tyr Ala Thr Leu Arg Val Pro Ala Gln Gln Gly Thr Gly His Leu
        115                 120                 125

Glu Met Gln Arg Asp Leu Arg Asn His Ser Ser Lys Val Val Ala Leu
    130                 135                 140

Ile Gly Pro Asp Asn Thr Asp His Ala Val Thr Thr Ala Ala Leu Leu
145                 150                 155                 160

Ser Pro Phe Leu Met Pro Leu Val Ser Tyr Glu Ala Ser Ser Val Ile
                165                 170                 175

Leu Ser Gly Lys Arg Lys Phe Pro Ser Phe Leu Arg Thr Ile Pro Ser
            180                 185                 190
```

-continued

```
Asp Lys Tyr Gln Val Glu Val Ile Val Arg Leu Leu Gln Ser Phe Gly
        195                 200                 205
Trp Val Trp Ile Ser Leu Val Gly Ser Tyr Gly Asp Tyr Gly Gln Leu
    210                 215                 220
Gly Val Gln Ala Leu Glu Glu Leu Ala Thr Pro Arg Gly Ile Cys Val
225                 230                 235                 240
Ala Phe Lys Asp Val Val Pro Leu Ser Ala Gln Ala Gly Asp Pro Arg
            245                 250                 255
Met Gln Arg Met Met Leu Arg Leu Ala Arg Ala Arg Thr Thr Val Val
        260                 265                 270
Val Val Phe Ser Asn Arg His Leu Ala Gly Val Phe Phe Arg Ser Val
    275                 280                 285
Val Leu Ala Asn Leu Thr Gly Lys Val Trp Ile Ala Ser Glu Asp Trp
    290                 295                 300
Ala Ile Ser Thr Tyr Ile Thr Asn Val Pro Gly Ile Gln Gly Ile Gly
305                 310                 315                 320
Thr Val Leu Gly Val Ala Ile Gln Gln Arg Gln Val Pro Gly Leu Lys
            325                 330                 335
Glu Phe Glu Glu Ser Tyr Val Gln Ala Val Met Gly Ala Pro Arg Thr
        340                 345                 350
Cys Pro Glu Gly Ser Trp Cys Gly Thr Asn Gln Leu Cys Arg Glu Cys
    355                 360                 365
His Ala Phe Thr Thr Trp Asn Met Pro Glu Leu Gly Ala Phe Ser Met
    370                 375                 380
Ser Ala Ala Tyr Asn Val Tyr Glu Ala Val Tyr Ala Val Ala His Gly
385                 390                 395                 400
Leu His Gln Leu Leu Gly Cys Thr Ser Gly Thr Cys Ala Arg Gly Pro
            405                 410                 415
Val Tyr Pro Trp Gln Leu Leu Gln Gln Ile Tyr Lys Val Asn Phe Leu
        420                 425                 430
Leu His Lys Lys Thr Val Ala Phe Asp Asp Lys Gly Asp Pro Leu Gly
    435                 440                 445
Tyr Tyr Asp Ile Ile Ala Trp Asp Trp Asn Gly Pro Glu Trp Thr Phe
    450                 455                 460
Glu Val Ile Gly Ser Ala Ser Leu Ser Pro Val His Leu Asp Ile Asn
465                 470                 475                 480
Lys Thr Lys Ile Gln Trp His Gly Lys Asn Asn Gln Val Pro Val Ser
            485                 490                 495
Val Cys Thr Arg Asp Cys Leu Glu Gly His His Arg Leu Val Met Gly
        500                 505                 510
Ser His His Cys Cys Phe Glu Cys Met Pro Cys Glu Ala Gly Thr Phe
    515                 520                 525
Leu Asn Thr Ser Glu Leu His Thr Cys Gln Pro Cys Gly Thr Glu Glu
    530                 535                 540
Trp Ala Pro Glu Gly Ser Ser Ala Cys Phe Ser Arg Thr Val Glu Phe
545                 550                 555                 560
Leu Gly Trp His Glu Pro Ile Ser Leu Val Leu Leu Ala Ala Asn Thr
            565                 570                 575
Leu Leu Leu Leu Leu Leu Ile Gly Thr Ala Gly Leu Phe Ala Trp Arg
        580                 585                 590
Leu His Thr Pro Val Val Arg Ser Ala Gly Gly Arg Leu Cys Phe Leu
    595                 600                 605
Met Leu Gly Ser Leu Val Ala Gly Ser Cys Ser Leu Tyr Ser Phe Phe
```

```
                610                 615                 620
Gly Lys Pro Thr Val Pro Ala Cys Leu Leu Arg Gln Pro Leu Phe Ser
625                 630                 635                 640

Leu Gly Phe Ala Ile Phe Leu Ser Cys Leu Thr Ile Arg Ser Phe Gln
                645                 650                 655

Leu Val Ile Ile Phe Lys Phe Ser Lys Val Pro Thr Phe Tyr His
                660                 665                 670

Thr Trp Ala Gln Asn His Gly Ala Gly Ile Phe Val Ile Val Ser Ser
                675                 680                 685

Thr Val His Leu Phe Leu Cys Leu Thr Trp Leu Ala Met Trp Thr Pro
                690                 695                 700

Arg Pro Thr Arg Glu Tyr Gln Arg Phe Pro His Leu Val Ile Leu Glu
705                 710                 715                 720

Cys Thr Glu Val Asn Ser Val Gly Phe Leu Val Ala Phe Ala His Asn
                725                 730                 735

Ile Leu Leu Ser Ile Ser Thr Phe Val Cys Ser Tyr Leu Gly Lys Glu
                740                 745                 750

Leu Pro Glu Asn Tyr Asn Glu Ala Lys Cys Val Thr Phe Ser Leu Leu
                755                 760                 765

Leu His Phe Val Ser Trp Ile Ala Phe Phe Thr Met Ser Ser Ile Tyr
                770                 775                 780

Gln Gly Ser Tyr Leu Pro Ala Val Asn Val Leu Ala Gly Leu Ala Thr
785                 790                 795                 800

Leu Ser Gly Gly Phe Ser Gly Tyr Phe Leu Pro Lys Cys Tyr Val Ile
                805                 810                 815

Leu Cys Arg Pro Glu Leu Asn Asn Thr Glu His Phe Gln Ala Ser Ile
                820                 825                 830

Gln Asp Tyr Thr Arg Arg Cys Gly Thr Thr
                835                 840

<210> SEQ ID NO 3
<211> LENGTH: 840
<212> TYPE: PRT
<213> ORGANISM: Rattus norvegicus

<400> SEQUENCE: 3

Met Leu Phe Trp Ala Ala His Leu Leu Leu Ser Leu Gln Leu Val Tyr
1               5                   10                  15

Cys Trp Ala Phe Ser Cys Gln Arg Thr Glu Ser Ser Pro Gly Phe Ser
                20                  25                  30

Leu Pro Gly Asp Phe Leu Leu Ala Gly Leu Phe Ser Leu His Gly Asp
                35                  40                  45

Cys Leu Gln Val Arg His Arg Pro Leu Val Thr Ser Cys Asp Arg Pro
50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
                100                 105                 110

Ala Thr Leu Arg Val Leu Ala Leu Gln Gly Pro Arg His Ile Glu Ile
                115                 120                 125

Gln Lys Asp Leu Arg Asn His Ser Ser Lys Val Val Ala Phe Ile Gly
130                 135                 140
```

-continued

```
Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
            165                 170                 175

Ala Lys Arg Lys Phe Pro Ser Phe Leu Arg Thr Val Pro Ser Asp Arg
        180                 185                 190

His Gln Val Glu Val Met Val Gln Leu Leu Gln Ser Phe Gly Trp Val
    195                 200                 205

Trp Ile Ser Leu Ile Gly Ser Tyr Gly Asp Tyr Gly Gln Leu Gly Val
210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
    275                 280                 285

Ala Asn Leu Thr Gly Lys Val Trp Val Ala Ser Glu Asp Trp Ala Ile
290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Gly Ser His
            500                 505                 510

His Cys Cys Phe Glu Cys Val Pro Cys Glu Ala Gly Thr Phe Leu Asn
        515                 520                 525

Met Ser Glu Leu His Ile Cys Gln Pro Cys Gly Thr Glu Glu Trp Ala
    530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
```

```
                    565                 570                 575
Leu Leu Leu Leu Val Gly Thr Ala Gly Leu Phe Ala Trp His Phe His
                580                 585                 590

Thr Pro Val Val Arg Ser Ala Gly Gly Arg Leu Cys Phe Leu Met Leu
            595                 600                 605

Gly Ser Leu Val Ala Gly Ser Cys Ser Phe Tyr Ser Phe Phe Gly Glu
        610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
        675                 680                 685

His Leu Leu Ile Cys Leu Thr Trp Leu Val Met Trp Thr Pro Arg Pro
    690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765

Phe Val Ser Trp Ile Ala Phe Phe Thr Met Ala Ser Ile Tyr Gln Gly
770                 775                 780

Ser Tyr Leu Pro Ala Val Asn Val Leu Ala Gly Leu Thr Thr Leu Ser
                785                 790                 795                 800

Gly Gly Phe Ser Gly Tyr Phe Leu Pro Lys Cys Tyr Val Ile Leu Cys
            805                 810                 815

Arg Pro Glu Leu Asn Asn Thr Glu His Phe Gln Ala Ser Ile Gln Asp
        820                 825                 830

Tyr Thr Arg Arg Cys Gly Thr Thr
        835                 840

<210> SEQ ID NO 4
<211> LENGTH: 839
<212> TYPE: PRT
<213> ORGANISM: Homo sapiens

<400> SEQUENCE: 4

Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95
```

-continued

```
Glu Ile Val Asp Val Cys Tyr Ile Ser Asn Val Gln Pro Val Leu
                100                 105                 110
Tyr Phe Leu Ala His Gly Asp Asn Leu Leu Pro Ile Gln Glu Asp Tyr
            115                 120                 125
Ser Asn Tyr Ile Ser Arg Ala Val Ala Val Ile Gly Pro Asp Asn Ser
        130                 135                 140
Glu Ser Val Met Thr Val Ala Asn Phe Leu Ser Leu Phe Leu Leu Pro
145                 150                 155                 160
Gln Ile Thr Tyr Ser Ala Ile Ser Asp Glu Leu Arg Asp Lys Val Arg
                165                 170                 175
Phe Pro Ala Leu Leu Arg Thr Thr Pro Ser Ala Asp His His Ile Glu
            180                 185                 190
Ala Met Val Gln Leu Met Leu His Phe Arg Trp Asn Trp Ile Ile Val
        195                 200                 205
Leu Val Ser Ser Asp Thr Tyr Gly Arg Asp Asn Gly Gln Leu Leu Gly
    210                 215                 220
Glu Arg Val Ala Arg Arg Asp Ile Cys Ile Ala Phe Gln Glu Thr Leu
225                 230                 235                 240
Pro Thr Leu Gln Pro Asn Gln Asn Met Thr Ser Glu Glu Arg Gln Arg
                245                 250                 255
Leu Val Thr Ile Val Asp Lys Leu Gln Gln Ser Thr Ala Arg Val Val
            260                 265                 270
Val Val Phe Ser Pro Asp Leu Thr Leu Tyr His Phe Phe Asn Glu Val
        275                 280                 285
Leu Arg Gln Asn Phe Thr Gly Ala Val Trp Ile Ala Ser Glu Ser Trp
    290                 295                 300
Ala Ile Asp Pro Val Leu His Asn Leu Thr Glu Leu Arg His Leu Gly
305                 310                 315                 320
Thr Phe Leu Gly Ile Thr Ile Gln Ser Val Pro Ile Pro Gly Phe Ser
                325                 330                 335
Glu Phe Arg Glu Trp Gly Pro Gln Ala Gly Pro Pro Leu Ser Arg
            340                 345                 350
Thr Ser Gln Ser Tyr Thr Cys Asn Gln Glu Cys Asp Asn Cys Leu Asn
        355                 360                 365
Ala Thr Leu Ser Phe Asn Thr Ile Leu Arg Leu Ser Gly Glu Arg Val
    370                 375                 380
Val Tyr Ser Val Tyr Ser Ala Val Tyr Ala Val Ala His Ala Leu His
385                 390                 395                 400
Ser Leu Leu Gly Cys Asp Lys Ser Thr Cys Thr Lys Arg Val Val Tyr
                405                 410                 415
Pro Trp Gln Leu Leu Glu Glu Ile Trp Lys Val Asn Phe Thr Leu Leu
            420                 425                 430
Asp His Gln Ile Phe Phe Asp Pro Gln Gly Asp Val Ala Leu His Leu
        435                 440                 445
Glu Ile Val Gln Trp Gln Trp Asp Arg Ser Gln Asn Pro Phe Gln Ser
    450                 455                 460
Val Ala Ser Tyr Tyr Pro Leu Gln Arg Gln Leu Lys Asn Ile Gln Asp
465                 470                 475                 480
Ile Ser Trp His Thr Ile Asn Asn Thr Ile Pro Met Ser Met Cys Ser
                485                 490                 495
Lys Arg Cys Gln Ser Gly Gln Lys Lys Lys Pro Val Gly Ile His Val
            500                 505                 510
Cys Cys Phe Glu Cys Ile Asp Cys Leu Pro Gly Thr Phe Leu Asn His
```

```
              515                 520                 525
Thr Glu Asp Glu Tyr Glu Cys Gln Ala Cys Pro Asn Asn Glu Trp Ser
        530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Pro Val Tyr Val Gly Pro
        610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
                660                 665                 670

Val Arg Tyr Gln Gly Pro Tyr Val Ser Met Ala Phe Ile Thr Val Leu
            675                 680                 685

Lys Met Val Ile Val Val Ile Gly Met Leu Ala Thr Gly Leu Ser Pro
        690                 695                 700

Thr Thr Arg Thr Asp Pro Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835

<210> SEQ ID NO 5
<211> LENGTH: 661
<212> TYPE: PRT
<213> ORGANISM: Mus musculus

<400> SEQUENCE: 5

Met Leu Arg Thr Val Pro Ser Ala Thr His His Ile Glu Ala Met Val
1               5                   10                  15

Gln Leu Met Val His Phe Gln Trp Asn Trp Ile Val Val Leu Val Ser
                20                  25                  30

Asp Asp Asp Tyr Gly Arg Glu Asn Ser His Leu Leu Ser Gln Arg Leu
            35                  40                  45
```

```
Thr Asn Thr Gly Asp Ile Cys Ile Ala Phe Gln Glu Val Leu Pro Val
 50                  55                  60

Pro Glu Pro Asn Gln Ala Val Arg Pro Glu Glu Gln Asp Gln Leu Asp
 65                  70                  75                  80

Asn Ile Leu Asp Lys Leu Arg Arg Thr Ser Ala Arg Val Val Val Ile
                 85                  90                  95

Phe Ser Pro Glu Leu Ser Leu His Asn Phe Arg Glu Val Leu Arg
            100                 105                 110

Trp Asn Phe Thr Gly Phe Val Trp Ile Ala Ser Glu Ser Trp Ala Ile
            115                 120                 125

Asp Pro Val Leu His Asn Leu Thr Glu Leu Arg His Thr Gly Thr Phe
        130                 135                 140

Leu Gly Val Thr Ile Gln Arg Val Ser Ile Pro Gly Phe Ser Gln Phe
145                 150                 155                 160

Arg Val Arg His Asp Lys Pro Glu Tyr Pro Met Pro Asn Glu Thr Ser
                165                 170                 175

Leu Arg Thr Thr Cys Asn Gln Asp Cys Asp Ala Cys Met Asn Ile Thr
            180                 185                 190

Glu Ser Phe Asn Asn Val Leu Met Leu Ser Gly Glu Arg Val Val Tyr
            195                 200                 205

Ser Val Tyr Ser Ala Val Tyr Ala Val Ala His Thr Leu His Arg Leu
210                 215                 220

Leu His Cys Asn Gln Val Arg Cys Thr Lys Gln Ile Val Tyr Pro Trp
225                 230                 235                 240

Gln Leu Leu Arg Glu Ile Trp His Val Asn Phe Thr Leu Leu Gly Asn
                245                 250                 255

Gln Leu Phe Phe Asp Glu Gln Gly Asp Met Pro Met Leu Leu Asp Ile
            260                 265                 270

Ile Gln Trp Gln Trp Gly Leu Ser Gln Asn Pro Phe Gln Ser Ile Ala
            275                 280                 285

Ser Tyr Ser Pro Thr Glu Thr Arg Leu Thr Tyr Ile Ser Asn Val Ser
            290                 295                 300

Trp Tyr Thr Pro Asn Asn Thr Val Pro Ile Ser Met Cys Ser Lys Ser
305                 310                 315                 320

Cys Gln Pro Gly Gln Met Lys Lys Pro Ile Gly Leu His Pro Cys Cys
                325                 330                 335

Phe Glu Cys Val Asp Cys Pro Pro Gly Thr Tyr Leu Asn Arg Ser Val
            340                 345                 350

Asp Glu Phe Asn Cys Leu Ser Cys Pro Gly Ser Met Trp Ser Tyr Lys
            355                 360                 365

Asn Asn Ile Ala Cys Phe Lys Arg Arg Leu Ala Phe Leu Glu Trp His
        370                 375                 380

Glu Val Pro Thr Ile Val Thr Ile Leu Ala Ala Leu Gly Phe Ile
385                 390                 395                 400

Ser Thr Leu Ala Ile Leu Leu Ile Phe Trp Arg His Phe Gln Thr Pro
            405                 410                 415

Met Val Arg Ser Ala Gly Gly Pro Met Cys Phe Leu Met Leu Val Pro
                420                 425                 430

Leu Leu Leu Ala Phe Gly Met Val Pro Val Tyr Val Gly Pro Pro Thr
            435                 440                 445

Val Phe Ser Cys Phe Cys Arg Gln Ala Phe Phe Thr Val Cys Phe Ser
450                 455                 460

Val Cys Leu Ser Cys Ile Thr Val Arg Ser Phe Gln Ile Val Cys Val
```

-continued

```
            465                 470                 475                 480
        Phe Lys Met Ala Arg Arg Leu Pro Ser Ala Tyr Gly Phe Trp Met Arg
                        485                 490                 495

Tyr His Gly Pro Tyr Val Phe Val Ala Phe Ile Thr Ala Val Lys Val
                    500                 505                 510

Ala Leu Val Ala Gly Asn Met Leu Ala Thr Thr Ile Asn Pro Ile Gly
                    515                 520                 525

Arg Thr Asp Pro Asp Pro Asn Ile Ile Ile Leu Ser Cys His Pro
                530                 535                 540

Asn Tyr Arg Asn Gly Leu Leu Phe Asn Thr Ser Met Asp Leu Leu
        545                 550                 555                 560

Ser Val Leu Gly Phe Ser Phe Ala Tyr Val Gly Lys Glu Leu Pro Thr
                        565                 570                 575

Asn Tyr Asn Glu Ala Lys Phe Ile Thr Leu Ser Met Thr Phe Ser Phe
                    580                 585                 590

Thr Ser Ser Ile Ser Leu Cys Thr Phe Met Ser Val His Asp Gly Val
                    595                 600                 605

Leu Val Thr Ile Met Asp Leu Leu Val Thr Val Leu Asn Phe Leu Ala
                    610                 615                 620

Ile Gly Leu Gly Tyr Phe Gly Pro Lys Cys Tyr Met Ile Leu Phe Tyr
        625                 630                 635                 640

Pro Glu Arg Asn Thr Ser Ala Tyr Phe Asn Ser Met Ile Gln Gly Tyr
                        645                 650                 655

Thr Met Arg Lys Ser
                    660

<210> SEQ ID NO 6
<211> LENGTH: 843
<212> TYPE: PRT
<213> ORGANISM: Rattus norvegicus

<400> SEQUENCE: 6

Met Gly Pro Gln Ala Arg Thr Leu Cys Leu Leu Ser Leu Leu Leu His
        1               5                   10                  15

Val Leu Pro Lys Pro Gly Lys Leu Val Glu Asn Ser Asp Phe His Leu
                    20                  25                  30

Ala Gly Asp Tyr Leu Leu Gly Gly Leu Phe Thr Leu His Ala Asn Val
                35                  40                  45

Lys Ser Ile Ser His Leu Ser Tyr Leu Gln Val Pro Lys Cys Asn Glu
        50                  55                  60

Phe Thr Met Lys Val Leu Gly Tyr Asn Leu Met Gln Ala Met Arg Phe
        65                  70                  75                  80

Ala Val Glu Glu Ile Asn Asn Cys Ser Ser Leu Leu Pro Gly Val Leu
                        85                  90                  95

Leu Gly Tyr Glu Met Val Asp Val Cys Tyr Leu Ser Asn Asn Ile His
                    100                 105                 110

Pro Gly Leu Tyr Phe Leu Ala Gln Asp Asp Leu Leu Pro Ile Leu
                115                 120                 125

Lys Asp Tyr Ser Gln Tyr Met Pro His Val Val Ala Val Ile Gly Pro
            130                 135                 140

Asp Asn Ser Glu Ser Ala Ile Thr Val Ser Asn Ile Leu Ser His Phe
        145                 150                 155                 160

Leu Ile Pro Gln Ile Thr Tyr Ser Ala Ile Ser Asp Lys Leu Arg Asp
                        165                 170                 175
```

-continued

```
Lys Arg His Phe Pro Ser Met Leu Arg Thr Val Pro Ser Ala Thr His
                180                 185                 190

His Ile Glu Ala Met Val Gln Leu Met Val His Phe Gln Trp Asn Trp
            195                 200                 205

Ile Val Val Leu Val Ser Asp Asp Tyr Gly Arg Glu Asn Ser His
        210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
    370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415

Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
    450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495

Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525

Tyr Leu Asn Arg Ser Ala Asp Glu Phe Asn Cys Leu Ser Cys Pro Gly
    530                 535                 540

Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
```

```
                595                 600                 605
Phe Leu Met Leu Val Pro Leu Leu Ala Phe Gly Met Val Pro Val
    610                 615                 620
Tyr Val Gly Pro Pro Thr Val Phe Ser Cys Phe Cys Arg Gln Ala Phe
625                 630                 635                 640
Phe Thr Val Cys Phe Ser Ile Cys Leu Ser Cys Ile Thr Val Arg Ser
                645                 650                 655
Phe Gln Ile Val Cys Val Phe Lys Met Ala Arg Arg Leu Pro Ser Ala
                660                 665                 670
Tyr Ser Phe Trp Met Arg Tyr His Gly Pro Tyr Val Phe Val Ala Phe
                675                 680                 685
Ile Thr Ala Ile Lys Val Ala Leu Val Val Gly Asn Met Leu Ala Thr
                690                 695                 700
Thr Ile Asn Pro Ile Gly Arg Thr Asp Pro Asp Pro Asn Ile Met
705                 710                 715                 720
Ile Leu Ser Cys His Pro Asn Tyr Arg Asn Gly Leu Leu Phe Asn Thr
                725                 730                 735
Ser Met Asp Leu Leu Ser Val Leu Gly Phe Ser Phe Ala Tyr Met
                740                 745                 750
Gly Lys Glu Leu Pro Thr Asn Tyr Asn Glu Ala Lys Phe Ile Thr Leu
                755                 760                 765
Ser Met Thr Phe Ser Phe Thr Ser Ile Ser Leu Cys Thr Phe Met
                770                 775                 780
Ser Val His Asp Gly Val Leu Val Thr Ile Met Asp Leu Leu Val Thr
785                 790                 795                 800
Val Leu Asn Phe Leu Ala Ile Gly Leu Gly Tyr Phe Gly Pro Lys Cys
                805                 810                 815
Tyr Met Ile Leu Phe Tyr Pro Glu Arg Asn Thr Ser Ala Tyr Phe Asn
                820                 825                 830
Ser Met Ile Gln Gly Tyr Thr Met Arg Lys Ser
                835                 840

<210> SEQ ID NO 7
<211> LENGTH: 850
<212> TYPE: PRT
<213> ORGANISM: Homo sapiens

<400> SEQUENCE: 7

Met Leu Gly Pro Ala Val Leu Gly Leu Ser Leu Trp Ala Leu Leu His
1               5                   10                  15
Pro Gly Thr Gly Ala Pro Leu Cys Leu Ser Gln Gln Leu Arg Met Lys
                20                  25                  30
Gly Asp Tyr Val Leu Gly Gly Leu Phe Pro Leu Gly Glu Ala Glu Glu
                35                  40                  45
Ala Gly Leu Arg Ser Arg Thr Arg Pro Ser Ser Pro Val Cys Thr Arg
            50                  55                  60
Phe Ser Ser Asn Gly Leu Leu Trp Ala Leu Ala Met Lys Met Ala Val
65                  70                  75                  80
Glu Glu Ile Asn Asn Lys Ser Asp Leu Leu Pro Gly Leu Arg Leu Gly
                85                  90                  95
Tyr Asp Leu Phe Asp Thr Cys Ser Glu Pro Val Val Ala Met Lys Pro
                100                 105                 110
Ser Leu Met Phe Leu Ala Lys Ala Gly Ser Arg Asp Ile Ala Ala Tyr
                115                 120                 125
```

```
Cys Asn Tyr Thr Gln Tyr Gln Pro Arg Val Leu Ala Val Ile Gly Pro
130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
                180                 185                 190

Gln Leu Thr Ala Ala Ala Glu Leu Leu Gln Glu Phe Gly Trp Asn Trp
                195                 200                 205

Val Ala Leu Gly Ser Asp Asp Glu Tyr Gly Arg Gln Gly Leu Ser
210                 215                 220

Ile Phe Ser Ala Leu Ala Ala Arg Gly Ile Cys Ile Ala His Glu
225                 230                 235                 240

Gly Leu Val Pro Leu Pro Arg Ala Asp Ser Arg Leu Gly Lys Val
                245                 250                 255

Gln Asp Val Leu His Gln Val Asn Gln Ser Ser Val Gln Val Val Leu
                260                 265                 270

Leu Phe Ala Ser Val His Ala Ala His Ala Leu Phe Asn Tyr Ser Ile
                275                 280                 285

Ser Ser Arg Leu Ser Pro Lys Val Trp Val Ala Ser Glu Ala Trp Leu
290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
                340                 345                 350

Ala Leu Gly Glu Arg Glu Gln Gly Leu Glu Glu Asp Val Val Gly Gln
                355                 360                 365

Arg Cys Pro Gln Cys Asp Cys Ile Thr Leu Gln Asn Val Ser Ala Gly
                370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
                420                 425                 430

Leu Thr Phe His Val Gly Gly Leu Pro Leu Arg Phe Asp Ser Ser Gly
                435                 440                 445

Asn Val Asp Met Glu Tyr Asp Leu Lys Leu Trp Val Trp Gln Gly Ser
450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Lys Pro Val Ser Arg
                485                 490                 495

Cys Ser Arg Gln Cys Gln Glu Gly Gln Val Arg Val Lys Gly Phe
                500                 505                 510

His Ser Cys Cys Tyr Asp Cys Val Asp Cys Glu Ala Gly Ser Tyr Arg
                515                 520                 525

Gln Asn Pro Asp Asp Ile Ala Cys Thr Phe Cys Gly Gln Asp Glu Trp
                530                 535                 540

Ser Pro Glu Arg Ser Thr Arg Cys Phe Arg Arg Arg Ser Arg Phe Leu
```

```
                          545                 550                 555                 560
    Ala Trp Gly Glu Pro Ala Val Leu Leu Leu Leu Leu Leu Ser Leu
                      565                 570                 575
    Ala Leu Gly Leu Val Leu Ala Ala Leu Gly Leu Phe Val His His Arg
                  580                 585                 590
    Asp Ser Pro Leu Val Gln Ala Ser Gly Gly Pro Leu Ala Cys Phe Gly
              595                 600                 605
    Leu Val Cys Leu Gly Leu Val Cys Leu Ser Val Leu Leu Phe Pro Gly
          610                 615                 620
    Gln Pro Ser Pro Ala Arg Cys Leu Ala Gln Gln Pro Leu Ser His Leu
    625                 630                 635                 640
    Pro Leu Thr Gly Cys Leu Ser Thr Leu Phe Leu Gln Ala Ala Glu Ile
                      645                 650                 655
    Phe Val Glu Ser Glu Leu Pro Leu Ser Trp Ala Asp Arg Leu Ser Gly
                  660                 665                 670
    Cys Leu Arg Gly Pro Trp Ala Trp Leu Val Val Leu Leu Ala Met Leu
              675                 680                 685
    Val Glu Val Ala Leu Cys Thr Trp Tyr Leu Val Ala Phe Pro Pro Glu
          690                 695                 700
    Val Val Thr Asp Trp His Met Leu Pro Thr Glu Ala Leu Val His Cys
    705                 710                 715                 720
    Arg Thr Arg Ser Trp Val Ser Phe Gly Leu Ala His Ala Thr Asn Ala
                      725                 730                 735
    Thr Leu Ala Phe Leu Cys Phe Leu Gly Thr Phe Leu Val Arg Ser Gln
                  740                 745                 750
    Pro Gly Arg Tyr Asn Arg Ala Arg Gly Leu Thr Phe Ala Met Leu Ala
              755                 760                 765
    Tyr Phe Ile Thr Trp Val Ser Phe Val Pro Leu Leu Ala Asn Val Gln
          770                 775                 780
    Val Val Leu Arg Pro Ala Val Gln Met Gly Ala Leu Leu Leu Cys Val
    785                 790                 795                 800
    Leu Gly Ile Leu Ala Ala Phe His Leu Pro Arg Cys Tyr Leu Leu Met
                      805                 810                 815
    Arg Gln Pro Gly Leu Asn Thr Pro Glu Phe Phe Leu Gly Gly Gly Pro
                  820                 825                 830
    Gly Asp Ala Gln Gly Gln Asn Asp Gly Asn Thr Gly Asn Gln Gly Lys
              835                 840                 845
    His Glu
        850

<210> SEQ ID NO 8
<211> LENGTH: 858
<212> TYPE: PRT
<213> ORGANISM: Mus musculus

<400> SEQUENCE: 8

Met Pro Ala Leu Ala Ile Met Gly Leu Ser Leu Ala Ala Phe Leu Glu
    1               5                   10                  15

Leu Gly Met Gly Ala Ser Leu Cys Leu Ser Gln Gln Phe Lys Ala Gln
                    20                  25                  30

Gly Asp Tyr Ile Leu Gly Gly Leu Phe Pro Leu Gly Ser Thr Glu Glu
                35                  40                  45

Ala Thr Leu Asn Gln Arg Thr Gln Pro Asn Ser Ile Pro Cys Asn Arg
        50                  55                  60
```

-continued

```
Phe Ser Pro Leu Gly Leu Phe Leu Ala Met Ala Met Lys Met Ala Val
 65              70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Tyr Gly Arg Glu Gly Leu Ser
    210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285

His His Gly Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Arg Cys Asp Asp Ile Met Leu Gln Asn Leu Ser Ser Gly Leu
    370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
        435                 440                 445

Leu Gln Phe Asp Ala Glu Gly Asn Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
```

-continued

```
                485                 490                 495
Asn Gln Val Pro Val Ser Gln Cys Ser Arg Gln Cys Lys Asp Gly Gln
            500                 505                 510
Val Arg Arg Val Lys Gly Phe His Ser Cys Cys Tyr Asp Cys Val Asp
            515                 520                 525
Cys Lys Ala Gly Ser Tyr Arg Lys His Pro Asp Asp Phe Thr Cys Thr
            530                 535                 540
Pro Cys Asn Gln Asp Gln Trp Ser Pro Glu Lys Ser Thr Ala Cys Leu
545                 550                 555                 560
Pro Arg Arg Pro Lys Phe Leu Ala Trp Gly Glu Pro Val Val Leu Ser
                565                 570                 575
Leu Leu Leu Leu Leu Cys Leu Val Leu Gly Leu Ala Leu Ala Ala Leu
            580                 585                 590
Gly Leu Ser Val His His Trp Asp Ser Pro Leu Val Gln Ala Ser Gly
            595                 600                 605
Gly Ser Gln Phe Cys Phe Gly Leu Ile Cys Leu Gly Leu Phe Cys Leu
            610                 615                 620
Ser Val Leu Leu Phe Pro Gly Arg Pro Ser Ser Ala Ser Cys Leu Ala
625                 630                 635                 640
Gln Gln Pro Met Ala His Leu Pro Leu Thr Gly Cys Leu Ser Thr Leu
                645                 650                 655
Phe Leu Gln Ala Ala Glu Thr Phe Val Glu Ser Glu Leu Pro Leu Ser
            660                 665                 670
Trp Ala Asn Trp Leu Cys Ser Tyr Leu Arg Gly Leu Trp Ala Trp Leu
            675                 680                 685
Val Val Leu Leu Ala Thr Phe Val Glu Ala Ala Leu Cys Ala Trp Tyr
            690                 695                 700
Leu Ile Ala Phe Pro Pro Glu Val Val Thr Asp Trp Ser Val Leu Pro
705                 710                 715                 720
Thr Glu Val Leu Glu His Cys His Val Arg Ser Trp Val Ser Leu Gly
                725                 730                 735
Leu Val His Ile Thr Asn Ala Met Leu Ala Phe Leu Cys Phe Leu Gly
            740                 745                 750
Thr Phe Leu Val Gln Ser Gln Pro Gly Arg Tyr Asn Arg Ala Arg Gly
            755                 760                 765
Leu Thr Phe Ala Met Leu Ala Tyr Phe Ile Thr Trp Val Ser Phe Val
            770                 775                 780
Pro Leu Leu Ala Asn Val Gln Val Ala Tyr Gln Pro Ala Val Gln Met
785                 790                 795                 800
Gly Ala Ile Leu Val Cys Ala Leu Gly Ile Leu Val Thr Phe His Leu
                805                 810                 815
Pro Lys Cys Tyr Val Leu Leu Trp Leu Pro Lys Leu Asn Thr Gln Glu
            820                 825                 830
Phe Phe Leu Gly Arg Asn Ala Lys Ala Ala Asp Glu Asn Ser Gly
            835                 840                 845
Gly Gly Glu Ala Ala Gln Gly His Asn Glu
    850                 855
```

<210> SEQ ID NO 9
<211> LENGTH: 858
<212> TYPE: PRT
<213> ORGANISM: Rattus norvegicus

<400> SEQUENCE: 9

-continued

```
Met Pro Gly Leu Ala Ile Leu Gly Leu Ser Leu Ala Ala Phe Leu Glu
1               5                   10                  15

Leu Gly Met Gly Ser Ser Leu Cys Leu Ser Gln Gln Phe Lys Ala Gln
            20                  25                  30

Gly Asp Tyr Ile Leu Gly Gly Leu Phe Pro Leu Gly Thr Thr Glu Glu
            35                  40                  45

Ala Thr Leu Asn Gln Arg Thr Gln Pro Asn Gly Ile Leu Cys Thr Arg
50                      55                  60

Phe Ser Pro Leu Gly Leu Phe Leu Ala Met Ala Met Lys Met Ala Val
65              70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Pro
                100                 105                 110

Ser Leu Met Phe Met Ala Lys Val Gly Ser Gln Ser Ile Ala Ala Tyr
            115                 120                 125

Cys Asn Tyr Thr Gln Tyr Gln Pro Arg Val Leu Ala Val Ile Gly Pro
130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Tyr Gly Arg Glu Gly Leu Ser
210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Leu Gly Lys Val
                245                 250                 255

Val Asp Val Leu Arg Gln Val Asn Gln Ser Lys Val Gln Val Val
            260                 265                 270

Leu Phe Ala Ser Ala Arg Ala Val Tyr Ser Leu Phe Ser Tyr Ser Ile
275                 280                 285

Leu His Asp Leu Ser Pro Lys Val Trp Val Ala Ser Glu Ser Trp Leu
290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr Arg Leu Ala Leu Ala Ala Asp Pro Thr Phe Cys Ala
            340                 345                 350

Ser Leu Lys Ala Glu Leu Asp Leu Glu Glu Arg Val Met Gly Pro Arg
            355                 360                 365

Cys Ser Gln Cys Asp Tyr Ile Met Leu Gln Asn Leu Ser Ser Gly Leu
        370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
```

-continued

```
                420             425             430
Leu Leu Glu Asn Met Tyr Asn Met Ser Phe Arg Ala Arg Asp Leu Thr
            435                 440                 445
Leu Gln Phe Asp Ala Lys Gly Ser Val Asp Met Glu Tyr Asp Leu Lys
        450                 455                 460
Met Trp Val Trp Gln Ser Pro Thr Pro Val Leu His Thr Val Gly Thr
465                 470                 475                 480
Phe Asn Gly Thr Leu Gln Leu Gln His Ser Lys Met Tyr Trp Pro Gly
                485                 490                 495
Asn Gln Val Pro Val Ser Gln Cys Ser Arg Gln Cys Lys Asp Gly Gln
            500                 505                 510
Val Arg Arg Val Lys Gly Phe His Ser Cys Cys Tyr Asp Cys Val Asp
        515                 520                 525
Cys Lys Ala Gly Ser Tyr Arg Lys His Pro Asp Asp Phe Thr Cys Thr
        530                 535                 540
Pro Cys Gly Lys Asp Gln Trp Ser Pro Glu Lys Ser Thr Thr Cys Leu
545                 550                 555                 560
Pro Arg Arg Pro Lys Phe Leu Ala Trp Gly Glu Pro Ala Val Leu Ser
                565                 570                 575
Leu Leu Leu Leu Leu Cys Leu Val Leu Gly Leu Thr Leu Ala Ala Leu
            580                 585                 590
Gly Leu Phe Val His Tyr Trp Asp Ser Pro Leu Val Gln Ala Ser Gly
        595                 600                 605
Gly Ser Leu Phe Cys Phe Gly Leu Ile Cys Leu Gly Leu Phe Cys Leu
        610                 615                 620
Ser Val Leu Leu Phe Pro Gly Arg Pro Arg Ser Ala Ser Cys Leu Ala
625                 630                 635                 640
Gln Gln Pro Met Ala His Leu Pro Leu Thr Gly Cys Leu Ser Thr Leu
                645                 650                 655
Phe Leu Gln Ala Ala Glu Ile Phe Val Glu Ser Glu Leu Pro Leu Ser
            660                 665                 670
Trp Ala Asn Trp Leu Cys Ser Tyr Leu Arg Gly Pro Trp Ala Trp Leu
        675                 680                 685
Val Val Leu Leu Ala Thr Leu Val Glu Ala Ala Leu Cys Ala Trp Tyr
        690                 695                 700
Leu Met Ala Phe Pro Pro Glu Val Val Thr Asp Trp Gln Val Leu Pro
705                 710                 715                 720
Thr Glu Val Leu Glu His Cys Arg Met Arg Ser Trp Val Ser Leu Gly
                725                 730                 735
Leu Val His Ile Thr Asn Ala Val Leu Ala Phe Leu Cys Phe Leu Gly
            740                 745                 750
Thr Phe Leu Val Gln Ser Gln Pro Gly Arg Tyr Asn Arg Ala Arg Gly
        755                 760                 765
Leu Thr Phe Ala Met Leu Ala Tyr Phe Ile Ile Trp Val Ser Phe Val
        770                 775                 780
Pro Leu Leu Ala Asn Val Gln Val Ala Tyr Gln Pro Ala Val Gln Met
785                 790                 795                 800
Gly Ala Ile Leu Phe Cys Ala Leu Gly Ile Leu Ala Thr Phe His Leu
                805                 810                 815
Pro Lys Cys Tyr Val Leu Leu Trp Leu Pro Glu Leu Asn Thr Gln Glu
            820                 825                 830
Phe Phe Leu Gly Arg Ser Pro Lys Glu Ala Ser Asp Gly Asn Ser Gly
        835                 840                 845
```

Ser Ser Glu Ala Thr Arg Gly His Ser Glu
    850                 855

<210> SEQ ID NO 10
<211> LENGTH: 2523
<212> TYPE: DNA
<213> ORGANISM: Homo sapiens

<400> SEQUENCE: 10

| | | | | |
|---|---|---|---|---|
| atgctgctct | gcacggctcg | cctggtcggc | ctgcagcttc | tcatttcctg | ctgctgggcc | 60 |
| tttgcctgcc | atagcacgga | gtcttctcct | gacttcaccc | tccccggaga | ttacctcctg | 120 |
| gcaggcctgt | tccctctcca | ttctggctgt | ctgcaggtga | ggcacagacc | cgaggtgacc | 180 |
| ctgtgtgaca | ggtcttgtag | cttcaatgag | catggctacc | acctcttcca | ggctatgcgg | 240 |
| cttggggttg | aggagataaa | caactccacg | gccctgctgc | caacatcac | cctggggtac | 300 |
| cagctgtatg | atgtgtgttc | tgactctgcc | aatgtgtatg | ccacgctgag | agtgctctcc | 360 |
| ctgccagggc | aacaccacat | agagctccaa | ggagaccttc | tccactattc | ccctacggtg | 420 |
| ctggcagtga | ttgggcctga | cagcaccaac | cgtgctgcca | ccacagccgc | cctgctgagc | 480 |
| cctttcctgg | tgcccatgct | tattagctat | gcggccagca | gcgagacgct | cagcgtgaag | 540 |
| cggcagtatc | cctctttcct | gcgcaccatc | cccaatgaca | gtaccaggt | ggagaccatg | 600 |
| gtgctgctgc | tgcagaagtt | cgggtggacc | tggatctctc | tggttggcag | cagtgacgac | 660 |
| tatgggcagc | taggggtgca | ggcactggag | aaccaggcca | ctggtcaggg | gatctgcatt | 720 |
| gctttcaagg | acatcatgcc | cttctctgcc | caggtgggcg | atgagaggat | gcagtgcctc | 780 |
| atgcgccacc | tggcccaggc | cggggccacc | gtcgtggttg | ttttttccag | ccggcagttg | 840 |
| gccagggtgt | ttttcgagtc | cgtggtgctg | accaacctga | ctggcaaggt | gtgggtcgcc | 900 |
| tcagaagcct | gggccctctc | caggcacatc | actggggtgc | ccgggatcca | gcgcattggg | 960 |
| atggtgctgg | gcgtggccat | ccagaagagg | gctgtccctg | gcctgaaggc | gtttgaagaa | 1020 |
| gcctatgccc | gggcagacaa | ggaggcccct | aggccttgcc | acaagggctc | ctggtgcagc | 1080 |
| agcaatcagc | tctgcagaga | atgccaagct | ttcatggcac | acacgatgcc | caagctcaaa | 1140 |
| gccttctcca | tgagttctgc | ctacaacgca | taccggctg | tgtatgcggt | ggcccatgc | 1200 |
| ctccaccagc | tcctgggctg | tgcctctgga | gcttgttcca | ggggccgagt | ctacccctgg | 1260 |
| cagttggagc | agatccacaa | ggtgcatttc | cttctacaca | aggacactgt | ggcgtttaat | 1320 |
| gacaacagag | atcccctcag | tagctataac | ataattgcct | gggactggaa | tggacccaag | 1380 |
| tggaccttca | cggtcctcgg | ttcctccaca | tggtctccag | ttcagctaaa | cataaatgag | 1440 |
| accaaaatcc | agtggcacgg | aaaggacaac | caggaaccaa | gtctgtgtgt | tccagcgact | 1500 |
| gtcttgaagg | gcaccagcga | gtggttacgg | gtttccatca | ctgctgcttt | gagtgtgtgc | 1560 |
| cctgtggggg | gttcttggcc | ttcccttttca | gacctctaca | gatgccagcc | ttgtgggaaa | 1620 |
| gaagagtggg | cacctgaggg | aagccagacc | tgcttcccgc | gcactgtggt | gttttggct | 1680 |
| ttgcgtgagc | acacctcttg | ggtgctgctg | cagctaacga | cgctgctgct | gctgctgctg | 1740 |
| cttgggactg | ctggcctgtt | tgcctggcac | ctagacaccc | ctgtggtgag | gtcagcaggg | 1800 |
| ggccgcctgt | gctttcttat | gctgggctcc | ctggcagcag | gtagtggcag | cctctatggc | 1860 |
| ttctttgggg | aacccacaag | gcctgcgtgc | ttgctacgcc | aggccctctt | tgcccttggt | 1920 |
| ttcaccatct | tcctgtcctg | cctgacagtt | cgctcattcc | aactaatcat | catcttcaag | 1980 |
| ttttccacca | aggtacctac | attctaccac | gcctgggtcc | aaaaccacgg | tgctggcctg | 2040 |

-continued

```
tttgtgatga tcagctcagc ggcccagctg cttatctgtc taacttggct ggtggtgtgg      2100 acccccactgc ctgctaggga ataccagcgc ttcccccatc tggtgatgct tgagtgcaca     2160
gagaccaact ccctgggctt catactggcc ttcctctaca atggcctcct ctccatcagt     2220
gcctttgcct gcagctacct gggtaaggac ttgccagaga actacaacga ggccaaatgt     2280
gtcaccttca gcctgctctt caacttcgtg tcctggatcg ccttcttcac cacgccagc      2340 gtctacgacg gcaagtacct gcctgcggcc aacatgatgg ctgggctgag cagcctgagc     2400
agcggcttcg tgggtatttt tctgcctaag tgctacgtga tcctctgccg cccagacctc     2460
aacagcacag agcacttcca ggcctccatt caggactaca cgaggcgctg cggctccacc     2520
tga                                                                    2523

<210> SEQ ID NO 11
<211> LENGTH: 2520
<212> TYPE: DNA
<213> ORGANISM: Homo sapiens

<400> SEQUENCE: 11
atggggccca gggcaaagac catctgctcc ctgttcttcc tcctatgggt cctggctgag        60
ccggctgaga actcggactt ctacctgcct ggggattacc tcctgggtgg cctcttctcc      120
ctccatgcca acatgaaggg cattgttcac cttaacttcc tgcaggtgcc catgtgcaag      180
gagtatgaag tgaaggtgat aggctacaac ctcatgcagg ccatgcgctt tgcggtggag      240
gagatcaaca atgacagcag cctgctgcct ggtgtgctgc tgggctatga gatcgtggat      300
gtgtgctaca tctccaacaa tgtccagccg gtgctctact tcctggcaca cggggacaac      360
ctccttccca tccaagagga ctacagtaac tacatttccc gtgcggtggc tgtcattggc      420
cctgacaact ccgagtctgt catgactgtg gccaacttcc tctccctatt tctccttcca      480
cagatcacct cagcgccat cagcgatgag ctgcgagaca aggtgcgctt ccggctttg       540 ctgcgtacca cacccagcgc cgaccaccac atcgaggcca tggtgcagct gatgctgcac      600
ttccgctgga actggatcat tgtgctggtg agcagcgaca cctatggccg cgacaatggc      660
cagctgcttg gcgagcgcgt ggcccggcgc gacatctgca tcgccttcca ggagacgctg      720
cccacactgc agcccaacca gaacatgacg tcagaggagc gccagcgcct ggtgaccatt      780
gtggacaagc tgcagcagag cacagcgcgc gtcgtggtcg tgttctcgcc cgacctgacc      840
ctgtaccact tcttcaatga ggtgctgcgc agaacttca ctggcgccgt gtggatcgcc       900
tccgagtcct gggccatcga cccggtcctg cacaacctca cggagctgcg ccacttgggc      960
accttcctgg gcatcaccat ccagagcgtg cccatcccgg cttcagtga gttccgcgag      1020 tggggcccac aggctgggcc gccaccccte agcaggacca gccagagcta cctgcaaac     1080 caggagtgcg acaactgcct gaacgccacc ttgtccttca acaccattct caggctctct     1140
ggggagcgtg tcgtctacag cgtgtactct gcggtctatg ctgtggccca tgccctgcac     1200
agcctcctcg gctgtgacaa aagcacctgc accaagaggg tggtctaccc ctggcagctg     1260
cttgaggaga tctggaaggt caacttcact ctcctggacc accaaatctt cttcgacccg     1320
caaggggacg tggctctgca cttggagatt gtccagtggc aatgggaccg gagccagaat     1380
cccttccaga gcgtcgcctc ctactacccc ctgcagcgac agctgaagaa catccaagac     1440
atctcctggc acaccatcaa caacacgatc cctatgtcca tgtgttccaa gaggtgccag     1500
tcagggcaaa agaagaagcc tgtgggcatc cacgtctgct gcttcgagtg catcgactgc     1560
```

```
cttcccggca ccttcctcaa ccacactgaa gatgaatatg aatgccaggc ctgcccgaat    1620
aacgagtggt cctaccagag tgagacctcc tgcttcaagc ggcagctggt cttcctggaa    1680
tggcatgagg cacccaccat cgctgtggcc ctgctggccg ccctgggctt cctcagcacc    1740
ctggccatcc tggtgatatt ctggaggcac ttccagacac ccatagttcg ctcggctggg    1800
ggccccatgt gcttcctgat gctgacactg ctgctggtgg catacatggt ggtcccggtg    1860
tacgtggggc cgcccaaggt ctccacctgc ctctgccgcc aggccctctt tcccctctgc    1920
ttcacaatct gcatctcctg tatcgccgtg cgttctttcc agatcgtctg cgccttcaag    1980
atggccagcc gcttcccacg cgcctacagc tactgggtcc gctaccaggg ccctacgtc     2040 tctatggcat ttatcacggt actcaaaatg gtcattgtgg taattggcat gctggccacg    2100
ggcctcagtc ccaccacccg tactgacccc gatgacccca agatcacaat tgtctcctgt    2160
aaccccaact accgcaacag cctgctgttc aacaccagcc tggacctgct gctctcagtg    2220
gtgggtttca gcttcgccta catgggcaaa gagctgccca ccaactacaa cgaggccaag    2280
ttcatcaccc tcagcatgac cttctatttc acctcatccg tctccctctg caccttcatg    2340
tctgcctaca gcggggtgct ggtcaccatc gtggacctct tggtcactgt gctcaacctc    2400
ctggccatca gcctgggcta cttcggcccc aagtgctaca tgatcctctt ctacccggag    2460
cgcaacacgc ccgcctactt caacagcatg atccagggct acaccatgag gagggactag    2520
```

<210> SEQ ID NO 12
<211> LENGTH: 2553
<212> TYPE: DNA
<213> ORGANISM: Homo sapiens

<400> SEQUENCE: 12

```
atgctgggcc ctgctgtcct gggcctcagc ctctgggctc tcctgcaccc tgggacgggg     60
gccccattgt gcctgtcaca gcaacttagg atgaagggg actacgtgct gggggggctg     120 ttcccccctgg gcgaggccga ggaggctggc ctccgcagcc ggacacggcc cagcagccct    180
gtgtgcacca ggttctcctc aaacggcctg ctctgggcac tggccatgaa aatggccgtg    240
gaggagatca acaacaagtc ggatctgctg cccgggctgc gcctgggcta cgacctcttt    300
gatacgtgct cggagcctgt ggtggccatg aagcccagcc tcatgttcct ggccaaggca    360
ggcagccgcg acatcgccgc ctactgcaac tacacgcagt accagccccg tgtgctggct    420
gtcatcgggc ccactcgtc agagctcgcc atggtcaccg gcaagttctt cagcttcttc    480
ctcatgcccc aggtcagcta cggtgctagc atggagctgc tgacgcccg ggagaccttc    540 ccctccttct tccgcaccgt gcccagcgac cgtgtgcagc tgacggccgc cgcggagctg    600
ctgcaggagt tcgctggaa ctgggtggcc gccctgggca cgacgacga gtacggccgg    660 cagggcctga gcatcttctc ggccctggcc gcggcacgcg gcatctgcat cgcgcacgag    720
ggcctggtgc cgctgccccg tgccgatgac tcgcggctgg ggaaggtgca ggacgtcctg    780
caccaggtga accagagcag cgtgcaggtg gtgctgctgt tcgcctccgt gcacgccgcc    840
cacgccctct tcaactacag catcagcagc aggctctcgc ccaaggtgtg ggtggccagc    900
gaggcctggc tgacctctga cctggtcatg gggctgccccg gcatgcccca gatgggcacg    960
gtgcttggct tcctccagag gggtgcccag ctgcacgagt cccccagta cgtgaagacg   1020 cacctggccc tggccaccga cccggccttc tgctctgccc tgggcgagag ggagcagggt   1080
ctggaggagg acgtggtggg ccagcgctgc ccgcagtgtg actgcatcac gctgcagaac   1140
gtgagcgcag ggctaaatca ccaccagacg ttctctgtct acgcagctgt gtatagcgtg   1200
```

```
gcccaggccc tgcacaacac tcttcagtgc aacgcctcag gctgcccgc gcaggacccc      1260 gtgaagccct ggcagctcct ggagaacatg tacaacctga ccttccacgt gggcgggctg      1320
ccgctgcggt tcgacagcag cggaaacgtg acatggagt acgacctgaa gctgtgggtg      1380
tggcagggct cagtgcccag gctccacgac gtgggcaggt tcaacggcag cctcaggaca      1440
gagcgcctga agatccgctg gcacacgtct gacaagcccg tgtcccggtg ctcgcggcag      1500
tgccaggagg gccaggtgcg ccgggtcaag gggttccact cctgctgcta cgactgtgtg      1560
gactgcgagg cgggcagcta ccggcaaaac ccagacgaca tcgcctgcac cttttgtggc      1620
caggatgagt ggtccccgga gcgaagcaca cgctgcttcc gccgcaggtc tcggttcctg      1680
gcatggggcg agccggctgt gctgctgctg ctcctgctgc tgagcctggc gctgggcctt      1740
gtgctggctg cctttggggct gttcgttcac catcgggaca gcccactggt tcaggcctcg      1800 gggggggcccc tggcctgctt tggcctggtg tgcctgggcc tggtctgcct cagcgtcctc      1860
ctgttccctg gccagcccag ccctgcccga tgcctggccc agcagccctt gtcccacctc      1920
ccgctcacgg gctgcctgag cacactcttc ctgcaggcgg ccgagatctt cgtggagtca      1980
gaactgcctc tgagctgggc agaccggctg agtggctgcc tgcggggcc ctgggcctgg      2040 ctggtggtgc tgctggccat gctggtggag gtcgcactgt gcacctggta cctggtggcc      2100
ttcccgccgg aggtggtgac ggactggcac atgctgccca cggaggcgct ggtgcactgc      2160
cgcacacgct cctgggtcag cttcggccta gcgcacgcca ccaatgccac gctggccttt      2220
ctctgcttcc tgggcacttt cctggtgcgg agccagccgg gccgctacaa ccgtgcccgt      2280
ggcctcacct ttgccatgct ggcctacttc atcacctggg tctcctttgt gcccctcctg      2340
gccaatgtgc aggtggtcct caggcccgcc gtgcagatgg gcgccctcct gctctgtgtc      2400
ctgggcatcc tggctgcctt ccacctgccc aggtgttacc tgctcatgcg gcagccaggg      2460
ctcaacaccc ccgagttctt cctgggaggg ggccctgggg atgcccaagg ccagaatgac      2520
gggaacacag gaaatcaggg gaaacatgag tga                                   2553
```

<210> SEQ ID NO 13
<211> LENGTH: 2529
<212> TYPE: DNA
<213> ORGANISM: Mus musculus

<400> SEQUENCE: 13

```
atgcttttct gggcagctca cctgctgctc agcctgcagc tggccgttgc ttactgctgg       60
gctttcagct gccaaaggac agaatcctct ccaggtttca gcctccctgg ggacttcctc      120
ctggcaggcc tgttctccct ccatgctgac tgtctgcagg tgagacacag acctctggtg      180
acaagttgtg acaggtctga cagcttcaac ggccatggct atcacctctt ccaagccatg      240
cggttcaccg ttgaggagat aaacaactcc acagctctgc ttcccaacat caccctgggg      300
tatgaactgt atgacgtgtg ctcagagtct tccaatgtct atgccaccct gagggtgccc      360
gcccagcaag ggacaggcca cctagagatg cagagagatc ttcgcaacca ctcctccaag      420
gtggtggcac tcattgggcc tgataacact gaccacgctg tcaccactgc tgccctgctg      480 agccctttc tgatgcccct ggtcagctat gaggcgagca gcgtgatcct cagtgggaag      540
cgcaagttcc cgtccttctt gcgcaccatc cccagcgata agtaccaggt ggaagtcata      600
gtgcggctgc tgcagagctt cggctgggtc tggatctcgc tcgttggcag ctatggtgac      660
tacgggcagc tgggcgtaca ggcgctggag gagctggcca ctccacgggg catctgcgtc      720
```

| | |
|---|---:|
| gccttcaagg acgtggtgcc tctctccgcc caggcgggtg acccaaggat gcagcgcatg | 780 |
| atgctgcgtc tggctcgagc caggaccacc gtggtcgtgg tcttctctaa ccggcacctg | 840 |
| gctggagtgt tcttcaggtc tgtggtgctg gccaacctga ctggcaaagt gtggatcgcc | 900 |
| tccgaagact gggccatctc cacgtacatc accaatgtgc ccgggatcca gggcattggg | 960 |
| acggtgctgg gggtggccat ccagcagaga caagtccctg gcctgaagga gtttgaagag | 1020 |
| tcctatgtcc aggcagtgat gggtgctccc agaacttgcc cagaggggtc ctggtgcggc | 1080 |
| actaaccagc tgtgcaggga gtgtcacgct ttcacgacat ggaacatgcc cgagcttgga | 1140 |
| gccttctcca tgagcgctgc ctacaatgtg tatgaggctg tgtatgctgt ggcccacggc | 1200 |
| ctccaccagc tcctgggatg tacctctggg acctgtgcca gaggcccagt ctacccctgg | 1260 |
| cagcttcttc agcagatcta caaggtgaat ttccttctac ataagaagac tgtagcattc | 1320 |
| gatgacaagg gggaccctct aggttattat gacatcatcg cctgggactg aatggacct | 1380 |
| gaatggacct ttgaggtcat tggttctgcc tcactgtctc cagttcatct agacataaat | 1440 |
| aagacaaaaa tccagtggca cgggaagaac aatcaggtgc ctgtgtcagt gtgtaccagg | 1500 |
| gactgtctcg aagggcacca caggttggtc atgggttccc accactgctg cttcgagtgc | 1560 |
| atgccctgtg aagctgggac atttctcaac acgagtgagc ttcacacctg ccagccttgt | 1620 |
| ggaacagaag aatgggcccc tgaggggagc tcagcctgct tctcacgcac cgtggagttc | 1680 |
| ttggggtggc atgaacccat ctctttggtg ctattagcag ctaacacgct attgctgctg | 1740 |
| ctgctgattg ggactgctgg cctgtttgcc tggcgtcttc acacgcctgt tgtgaggtca | 1800 |
| gctgggggta ggctgtgctt cctcatgctg ggttccttgg tagctgggag ttgcagcctc | 1860 |
| tacagcttct tcgggaagcc cacggtgccc gcgtgcttgc tgcgtcagcc cctctttttct | 1920 |
| ctcgggtttg ccattttcct ctcctgtctg acaatccgct ccttccaact ggtcatcatc | 1980 |
| ttcaagtttt ctaccaaggt acccacattc taccacactt gggcccaaaa ccatggtgcc | 2040 |
| ggaatattcg tcattgtcag ctccacggtc catttgttcc tctgtctcac gtggcttgca | 2100 |
| atgtggaccc cacggcccac cagggagtac cagcgcttcc cccatctggt gattcttgag | 2160 |
| tgcacagagg tcaactctgt gggcttcctg gtggctttcg cacacaacat cctcctctcc | 2220 |
| atcagcacct ttgtctgcag ctacctgggt aaggaactgc cggagaacta taacgaagcc | 2280 |
| aaatgtgtca ccttcagcct gctcctccac ttcgtatcct ggatcgcttt cttcaccatg | 2340 |
| tccagcattt accagggcag ctacctaccc gcggtcaatg tgctggcagg gctggccact | 2400 |
| ctgagtggcg gcttcagcgg ctatttcctc cctaaatgct acgtgattct ctgccgtcca | 2460 |
| gaactcaaca acacagaaca ctttcaggcc tccatccagg actacgag gcgctgcggc | 2520 |
| actacctga | 2529 |

<210> SEQ ID NO 14
<211> LENGTH: 1986
<212> TYPE: DNA
<213> ORGANISM: Mus musculus

<400> SEQUENCE: 14

| | |
|---|---:|
| atgctgcgca ctgtgcccag cgccacccac cacatcgagg ccatggtgca actgatggtt | 60 |
| cacttccagt ggaactggat cgtggtgctg gtgagcgatg acgattatgg ccgagagaac | 120 |
| agccacctgc tgagccagcg tctgaccaac actggcgata tctgcattgc cttccaggag | 180 |
| gttctgcctg taccgaaacc caaccaggcc gtgaggcctg aggagcagga ccaactggac | 240 |
| aacatcctgg acaagctgcg gcggacctcg gcgcgtgtgg tggtgatatt ctcgccagag | 300 |

```
ctgagcctgc acaacttctt ccgcgaggtg ctgcgctgga acttcacagg ctttgtgtgg      360
attgcctctg agtcctgggc catcgaccct gttctacaca acctcacaga gctgcgccac      420
acgggcactt tcctgggcgt caccatccag agggtgtcca tccctggctt cagccagttc      480
cgagtgcgcc acgacaagcc agagtatccc atgcctaacg agaccagcct gaggactacc      540
tgtaaccagg actgtgacgc tgcatgaac atcaccgagt cctttaacaa cgttctcatg      600
ctttcggggg agcgtgtggt ctacagtgtg tactcggccg tctacgcggt agcccacacc      660
ctccacagac tcctccactg caaccaggtc cgctgcacca gcaaatcgt ctatccatgg      720
cagctactca gggagatctg gcatgtcaac ttcacgctcc tgggcaacca gctcttcttc      780
gacgaacaag gggacatgcc gatgctcctg acatcatcc agtggcaatg gggcctgagc      840
cagaacccct tccaaagcat cgcctcctac tcccccaccg agacgaggct gacctacatt      900
agcaatgtgt cctggtacac ccccaacaac acggtcccca tatccatgtg ttctaagagt      960
tgccagcctg gcaaatgaa aaaacccata ggcctccacc cgtgctgctt cgagtgtgtg     1020
gactgtccgc cgggcaccta cctcaaccga tcagtagatg agtttaactg tctgtccctg     1080
ccgggttcca tgtggtctta caagaacaac atcgcttgct tcaagcggcg gctggccttc     1140
ctggagtggc acgaagtgcc cactatcgtg gtgaccatcc tggccgccct gggcttcatc     1200
agtacgctgg ccattctgct catcttctgg agacatttcc agacgccat ggtgcgctcg     1260
gcgggcggcc ccatgtgctt cctgatgctg gtgcccctgc tgctggcgtt cgggatggtc     1320
cccgtgtatg tgggcccccc cacggtcttc tcctgttttct gccgccaggc tttcttcacc     1380
gtttgcttct ccgtctgcct ctcctgcatc acggtgcgct ccttccagat tgtgtgcgtc     1440
ttcaagatgg ccgacgcct gccaagcgcc tacgtttct ggatgcgtta ccacgggccc     1500
tacgtctttg tggccttcat cacggccgtc aaggtggccc tggtggcagg caacatgctg     1560
gccaccacca tcaaccccat tggccggacc gaccccgatg accccaatat cataatcctc     1620
tcctgccacc ctaactaccg caacgggcta ctcttcaaca ccagcatgga cttgctgctg     1680
tccgtgctgg gtttcagctt cgcgtacgtg ggcaaggaac tgcccaccaa ctacaacgaa     1740
gccaagttca tcaccctcag catgaccttc tccttcacct cctccatctc cctctgcacg     1800
ttcatgtctg tccacgatgg cgtgctggtc accatcatgg atctcctggt cactgtgctc     1860
aactttctgg ccatcggctt ggggtacttt ggccccaagt gttacatgat ccttttctac     1920
ccggagcgca acacttcagc ttatttcaat agcatgattc agggctacac gatgaggaag     1980
agctag                                                              1986

<210> SEQ ID NO 15
<211> LENGTH: 2577
<212> TYPE: DNA
<213> ORGANISM: Mus musculus

<400> SEQUENCE: 15
atgccagctt tggctatcat gggtctcagc ctggctgctt cctggagct tgggatgggg      60
gcctctttgt gtctgtcaca gcaattcaag gcacaagggg actacatact gggcgggcta     120
tttcccctgg gctcaaccga ggaggccact ctcaaccaga gaacacaacc caacagcatc     180
ccgtgcaaca ggttctcacc ccttggtttg ttcctggcca tggctatgaa gatggctgtg     240
gaggagatca acaatggatc tgccttgctc cctgggctgc ggctgggcta tgacctattt     300
gacacatgct ccgagccagt ggtcaccatg aaatccagtc tcatgttcct ggccaaggtg     360
```

-continued

```
ggcagtcaaa gcattgctgc ctactgcaac tacacacagt accaaccccg tgtgctggct    420
gtcatcggcc cccactcatc agagcttgcc ctcattacag gcaagttctt cagcttcttc    480
ctcatgccac aggtcagcta tagtgccagc atggatcggc taagtgaccg ggaaacgttt    540
ccatccttct tccgcacagt gcccagtgac cgggtgcagc tgcaggcagt tgtgactctg    600
ttgcagaact tcagctggaa ctgggtggcc gccttaggga gtgatgatga ctatggccgg    660
gaaggtctga gcatcttttc tagtctgccc aatgcacgag gtatctgcat cgcacatgag    720
ggcctggtgc cacaacatga cactagtggc caacagttgg gcaaggtgct ggatgtacta    780
cgccaagtga accaaagtaa agtacaagtg gtggtgctgt ttgcctctgc ccgtgctgtc    840
tactcccttt ttagttacag catccatcat ggcctctcac ccaaggtatg ggtggccagt    900
gagtcttggc tgacatctga cctggtcatg acacttccca atattgcccg tgtgggcact    960
gtgcttgggt ttttgcagcg gggtgcccta ctgcctgaat tttcccatta tgtggagact   1020
caccttgccc tggccgctga cccagcattc tgtgcctcac tgaatgcgga gttggatctg   1080
gaggaacatg tgatggggca acgctgtcca cggtgtgacg acatcatgct gcagaaccta   1140
tcatctgggc tgttgcagaa cctatcagct gggcaattgc accaccaaat atttgcaacc   1200
tatgcagctg tgtacagtgt ggctcaagcc cttcacaaca ccctacagtg caatgtctca   1260
cattgccacg tatcagaaca tgttctaccc tggcagctcc tggagaacat gtacaatatg   1320
agtttccatg ctcgagactt gacactacag tttgatgctg aagggaatgt agacatggaa   1380
tatgacctga agatgtgggt gtggcagagc cctacacctg tattacatac tgtgggcacc   1440
ttcaacggca cccttcagct gcagcagtct aaaatgtact ggccaggcaa ccaggtgcca   1500
gtctcccagt gttcccgcca gtgcaaagat ggccaggttc gccgagtaaa gggctttcat   1560
tcctgctgct atgactgcgt ggactgcaag gcgggcagct accggaagca tccagatgac   1620
ttcacctgta ctccatgtaa ccaggaccag tggtccccag agaaaagcac agcctgctta   1680
cctcgcaggc ccaagtttct ggcttggggg gagccagttg tgctgtcact cctcctgctg   1740
cttttgcctgg tgctgggtct agcactggct gctctggggc tctctgtcca ccactgggac   1800
agccctcttg tccaggcctc aggtggctca cagttctgct ttggcctgat ctgcctaggc   1860
ctcttctgcc tcagtgtcct tctgttccca gggcggccaa gctctgccag ctgccttgca   1920
caacaaccaa tggctcacct ccctctcaca ggctgcctga gcacactctt cctgcaagca   1980
gctgagacct ttgtggagtc tgagctgcca ctgagctggg caaactggct atgcagctac   2040
cttcggggac tctgggcctg ctagtggta ctgttggcca cttttgtgga ggcagcacta   2100
tgtgcctggt atttgatcgc tttcccacca gaggtggtga cagactggtc agtgctgccc   2160
acagaggtac tggagcactg ccacgtgcgt tcctgggtca gctgggcttt ggtgcacatc   2220
accaatgcaa tgttagcttt cctctgcttt ctgggcactt tcctggtaca gagccagcct   2280
ggccgctaca accgtgcccg tggtctcacc ttcgccatgc tagcttattt catcacctgg   2340
gtctcttttg tgcccctcct ggccaatgtg caggtggcct accagccagc tgtgcagatg   2400
ggtgctatcc tagtctgtgc cctgggcatc ctggtcacct tccacctgcc caagtgctat   2460
gtgcttcttt ggctgccaaa gctcaacacc caggagttct tcctgggaag gaatgccaag   2520
aaagcagcag atgagaacag tggcggtggt gaggcagctc agggacacaa tgaatga      2577
```

<210> SEQ ID NO 16
<211> LENGTH: 2523
<212> TYPE: DNA
<213> ORGANISM: Rattus norvegicus

<400> SEQUENCE: 16

```
atgctcttct gggctgctca cctgctgctc agcctgcagt tggtctactg ctgggctttc      60
agctgccaaa ggacagagtc ctctccaggc ttcagccttc ctggggactt cctccttgca     120
ggtctgttct ccctccatgg tgactgtctg caggtgagac acagacctct ggtgacaagt     180
tgtgacaggc ccgacagctt caacggccat ggctaccacc tcttccaagc catgcggttc     240
actgttgagg agataaacaa ctcctcggcc ctgcttccca acatcaccct ggggtatgag     300
ctgtacgacg tgtgctcaga atctgccaat gtgtatgcca ccctgagggt gcttgccctg     360
caagggcccc gccacataga gatacagaaa gaccttcgca accactcctc aaggtggtg     420
gccttcatcg ggcctgacaa cactgaccac gctgtcacta ccgctgcctt gctgggtcct     480
ttcctgatgc ccctggtcag ctatgaggca agcagcgtgg tactcagtgc aagcgcaag     540
ttcccgtctt ccttcgtac cgtcccagt gaccggcacc aggtggaggt catggtgcag      600
ctgctgcaga gttttgggtg ggtgtggatc tcgctcattg gcagctacgg tgattacggg     660
cagctgggtg tgcaggcgct ggaggagctg gccgtgcccc ggggcatctg cgtcgccttc     720
aaggacatcg tgcctttctc tgcccgggtg ggtgacccga ggatgcagag catgatgcag     780
catctggctc aggccaggac caccgtggtt gtggtcttct ctaaccggca cctggctaga     840
gtgttcttca ggtccgtggt gctggccaac ctgactggca agtgtgggt cgcctcagaa      900
gactgggcca tctccacgta catcaccagc gtgactggga tccaaggcat gggacggtg      960
ctcggtgtgg ccgtccagca gagacaagtc cctgggctga aggagtttga ggagtcttat    1020
gtcagggctg taacagctgc tcccagcgct tgcccggagg ggtcctggtg cagcactaac    1080
cagctgtgcc gggagtgcca cacgttcacg actcgtaaca tgcccacgct ggagccttc     1140
tccatgagtg ccgcctacag agtgtatgag gctgtgtacg ctgtggccca cggcctccac    1200
cagctcctgg gatgtacttc tgagatctgt tccagaggcc cagtctaccc ctggcagctt    1260
cttcagcaga tctacaaggt gaattttctt ctacatgaga atactgtggc atttgatgac    1320
aacggggaca ctctaggtta ctacgacatc atcgcctggg actggaatgg acctgaatgg    1380
accttgaga tcattggctc tgcctcactg tctccagttc atctggacat aaataagaca    1440
aaaatccagt ggcacgggaa gaacaatcag gtgcctgtgt cagtgtgtac cacgactgt    1500
ctggcagggc accacagggt ggttgtgggt tcccaccact gctgctttga gtgtgtgccc    1560
tgcgaagctg gaccttttct caacatgagt gagcttcaca tctgccagcc ttgtggaaca    1620
gaagaatggg cacccaagga gagcactact tgcttcccac gcacggtgga gttcttggct    1680
tggcatgaac ccatctcttt ggtgctaata gcagctaaca cgctattgct gctgctgctg    1740
gttgggactg ctggcctgtt tgcctggcat tttcacacac ctgtagtgag gtcagctggg    1800
ggtaggctgt gcttcctcat gctgggttcc ctggtggccg aagttgcag cttctatagc    1860
ttcttcgggg agcccacggt gccgcgtgc ttgctgcgtc agcccctctt ttctctcggg     1920
tttgccatct tcctctcctg cctgacaatc cgctccttcc aactggtcat catcttcaag    1980
tttttctacca aggtgcccac attctaccgt acctgggccc aaaaccatgg tgcaggtcta    2040
ttcgtcattg tcagctccac ggtccatttg ctcatctgtc tcacatggct tgtaatgtgg    2100
accccacgac ccaccaggga ataccagcgc ttccccatc tggtgattct cgagtgcaca    2160
gaggtcaact ctgtaggctt cctgttggct ttcacccaca acattctcct ctccatcagt    2220
accttcgtct gcagctacct gggtaaggaa ctgccagaga actataatga agccaaatgt    2280
```

-continued

| | |
|---|---|
| gtcaccttca gcctgctcct caacttcgta tcctggatcg ccttcttcac catggccagc | 2340 |
| atttaccagg gcagctacct gcctgcggtc aatgtgctgg cagggctgac cacactgagc | 2400 |
| ggcggcttca gcggttactt cctccccaag tgctatgtga ttctctgccg tccagaactc | 2460 |
| aacaatacag aacactttca ggcctccatc caggactaca cgaggcgctg cggcactacc | 2520 |
| tga | 2523 |

<210> SEQ ID NO 17
<211> LENGTH: 2529
<212> TYPE: DNA
<213> ORGANISM: Rattus norvegicus

<400> SEQUENCE: 17

| | |
|---|---|
| atgggtcccc aggcaaggac actctgcttg ctgtctctcc tgctgcatgt tctgcctaag | 60 |
| ccaggcaagc tggtagagaa ctctgacttc cacctggccg gggactacct cctgggtggc | 120 |
| ctctttaccc tccatgccaa cgtgaagagc atctcccacc tcagctacct gcaggtgccc | 180 |
| aagtgcaatg agttcaccat gaaggtgttg ggctacaacc tcatgcaggc catgcgtttc | 240 |
| gctgtggagg agatcaacaa ctgtagctcc ctgctacccg cgtgctgct cggctacgag | 300 |
| atggtggatg tctgttacct ctccaacaat atccaccctg gctctactt cctggcacag | 360 |
| gacgacgacc tcctgcccat cctcaaagac tacagccagt acatgcccca cgtggtggct | 420 |
| gtcattggcc ccgacaactc tgagtccgcc attaccgtgt ccaacattct ctctcatttc | 480 |
| ctcatcccac agatcacata cagcgccatc tccgacaagc tgcgggacaa gcggcacttc | 540 |
| cctagcatgc tacgcacagt gcccagcgcc acccaccaca tcgaggccat ggtgcagctg | 600 |
| atggttcact tccaatggaa ctggattgtg gtgctggtga cgacgacga ttacggccgc | 660 |
| gagaacagcc acctgttgag ccagcgtctg accaaaacga gcgacatctg cattgccttc | 720 |
| caggaggttc tgcccatacc tgagtccagc caggtcatga ggtccgagga gcagagacaa | 780 |
| ctggacaaca tcctggacaa gctgcggcgg acctcggcgc gcgtcgtggt ggtgttctcg | 840 |
| cccgagctga gcctgtatag cttctttcac gaggtgctcc gctggaactt cacgggtttt | 900 |
| gtgtggatcg cctctgagtc ctgggctatc gacccagttc tgcataacct cacggagctg | 960 |
| cgccacacgg gtactttcct gggcgtcacc atccagaggg tgtccatccc tggcttcagt | 1020 |
| cagttccgag tgcgccgtga caagccaggg tatcccgtgc taacacgac caacctgcgg | 1080 |
| acgacctgca accaggactg tgacgcctgc ttgaacacca ccaagtcctt caacaacatc | 1140 |
| cttatacttt cggggagcg cgtggtctac agcgtgtact cggcagttta cgcggtggcc | 1200 |
| catgccctcc acagactcct cggctgtaac cgggtccgct gcaccaagca aaaggtctac | 1260 |
| ccgtggcagc tactcaggga gatctggcac gtcaacttca cgctcctggg taaccggctc | 1320 |
| ttctttgacc aacaagggga catgccgatg ctcttggaca tcatccagtg gcagtgggac | 1380 |
| ctgagccaga atcccttcca aagcatcgcc tcctattctc ccaccagcaa gaggctaacc | 1440 |
| tacattaaca atgtgtcctg gtacaccccc aacaacacgg tccctgtctc catgtgttcc | 1500 |
| aagagctgcc agccagggca aatgaaaaag tctgtgggcc tccacccttg ttgcttcgag | 1560 |
| tgcttggatt gtatgccagg cacctacctc aaccgctcag cagatgagtt taactgtctg | 1620 |
| tcctgcccgg gttccatgtg gtcctacaag aacgacatca cttgcttcca gcggcggcct | 1680 |
| accttcctgg agtggcacga agtgccccac atcgtggtgg ccatactggc tgccctgggc | 1740 |
| ttcttcagta cactgccat tcttttcatc ttctggagac atttccagac acccatggtg | 1800 |
| cgctcggccg gtggccccat gtgcttcctg atgctcgtgc cctgctgctg gcgctttggg | 1860 |

```
atggtgcccg tgtatgtggg gccccccacg gtcttctcat gcttctgccg acaggctttc   1920
ttcaccgtct gcttctccat ctgcctatcc tgcatcaccg tgcgctcctt ccagatcgtg   1980
tgtgtcttca agatggccag acgcctgcca agtgcctaca gttttggat gcgttaccac    2040 gggccctatg tcttcgtggc cttcatcacg gccatcaagg tggccctggt ggtgggcaac   2100
atgctggcca ccaccatcaa ccccattggc cggaccgacc cggatgaccc caacatcatg   2160
atcctctcgt gccaccctaa ctaccgcaac gggctactgt tcaacaccag catggacttg   2220
ctgctgtctg tgctgggttt cagcttcgct tacatgggca aggagctgcc caccaactac   2280
aacgaagcca agttcatcac tctcagcatg accttctcct tcacctcctc catctccctc   2340
tgcaccttca tgtctgtgca cgacggcgtg ctggtcacca tcatggacct cctggtcact   2400
gtgctcaact tcctggccat cggcttggga tactttggcc ccaagtgtta catgatcctt   2460
ttctacccgg agcgcaacac ctcagcctat ttcaatagca tgatccaggg ctacaccatg   2520
aggaagagc                                                           2529
```

<210> SEQ ID NO 18
<211> LENGTH: 2577
<212> TYPE: DNA
<213> ORGANISM: Rattus norvegicus

<400> SEQUENCE: 18

```
atgccgggtt tggctatctt gggcctcagt ctggctgctt tcctggagct tgggatgggg     60
tcctctttgt gtctgtcaca gcaattcaag gcacaagggg actatatatt gggtggacta   120
tttcccctgg gcacaactga ggaggccact ctcaaccaga aacacagcc caacggcatc    180 ctatgtacca ggttctcgcc ccttggtttg ttcctggcca tggctatgaa gatggctgta   240
gaggagatca acaatggatc tgccttgctc cctgggctgc gactgggcta tgacctgttt   300
gacacatgct cagagccagt ggtcaccatg aagcccagcc tcatgttcat ggccaaggtg   360
ggaagtcaaa gcattgctgc ctactgcaac tacacacagt accaacccccg tgtgctggct   420 gtcattggtc cccactcatc agagcttgcc ctcattacag gcaagttctt cagcttcttc   480
ctcatgccac aggtcagcta tagtgccagc atggatcggc taagtgaccg ggaaacattt   540
ccatccttct ccgcacagt gcccagtgac cgggtgcagc tgcaggccgt tgtgacactg   600
ttgcagaatt tcagctggaa ctgggtggct gccttaggta gtgatgatga ctatggccgg   660
gaaggtctga gcatcttttc tggtctggcc aactcacgag gtatctgcat gcacacgag    720 ggcctggtgc acaacatgga cactagtggc caacaattgg gcaaggtggt ggatgtgcta   780
cgccaagtga accaaagcaa agtacaggtg gtggtgctgt ttgcatctgc ccgtgctgtc   840
tactcccttt ttagctacag catccttcat gacctctcac ccaaggtatg ggtggccagt   900
gagtcctggc tgacctctga cctggtcatg acacttccca atattgcccg tgtgggcact   960
gttcttgggt ttctgcagcg cggtgcccta ctgcctgaat tttcccatta tgtggagact  1020
cgccttgccc tagctgctga cccaacattc tgtgcctccc tgaaagctga gttggatctg  1080
gaggagcgcg tgatggggcc acgctgttca caatgtgact acatcatgct acagaacctg  1140
tcatctgggc tgatgcagaa cctatcagct gggcagttgc accaccaaat atttgcaacc  1200
tatgcagctg tgtacagtgt ggctcaggcc cttcacaaca ccctgcagtg caatgtctca  1260
cattgccaca catcagagcc tgttcaaccc tggcagctcc tggagaacat gtacaatatg  1320
agtttccgtg ctcgagactt gacactgcag tttgatgcca aagggagtgt agacatggaa  1380
```

```
tatgacctga agatgtgggt gtggcagagc cctacacctg tactacatac tgtaggcacc    1440
ttcaacggca cccttcagct gcagcactcg aaaatgtatt ggccaggcaa ccaggtgcca    1500
gtctcccagt gctcccggca gtgcaaagat ggccaggtgc gcagagtaaa gggcttccat    1560
tcctgctgct atgactgtgt ggactgcaag gcagggagct accggaagca tccagatgac    1620
ttcacctgta ctccatgtgg caaggatcag tggtccccag aaaaaagcac aacctgctta    1680
cctcgcaggc ccaagtttct ggcttggggg agccagctg tgctgtcact tctcctgctg    1740
ctttgcctgg tgctgggcct gacactggct gccctgggc tctttgtcca ctactgggac    1800
agccctcttg ttcaggcctc aggtgggtca ctgttctgct ttggcctgat ctgcctaggc    1860
ctcttctgcc tcagtgtcct tctgttccca ggacgaccac gctctgccag ctgccttgcc    1920
caacaaccaa tggctcacct ccctctcaca ggctgcctga gcacactctt cctgcaagca    1980
gccgagatct ttgtggagtc tgagctgcca ctgagttggg caaactggct ctgcagctac    2040
cttcggggcc cctgggcttg gctggtggta ctgctggcca ctcttgtgga ggctgcacta    2100
tgtgcctggt acttgatggc tttccctcca gaggtggtga cagattggca ggtgctgccc    2160
acggaggtac tggaacactg ccgcatgcgt tcctgggtca gctgggcttc ggtgcacatc    2220
accaatgcag tgttagcttt cctctgcttt ctgggcactt tcctggtaca gagccagcct    2280
ggtcgctata accgtgcccg tggcctcacc ttcgccatgc tagcttattt catcatctgg    2340 gtctctttg tgcccctcct ggctaatgtg caggtggcct accagccagc tgtgcagatg    2400
ggtgctatct tattctgtgc cctgggcatc tggccacct tccacctgcc caaatgctat    2460
gtacttctgt ggctgccaga gctcaacacc caggagttct tcctgggaag gagccccaag    2520
gaagcatcag atgggaatag tggtagtagt gaggcaactc ggggacacag tgaatga      2577
```

<210> SEQ ID NO 19
<211> LENGTH: 18
<212> TYPE: DNA
<213> ORGANISM: artificial
<220> FEATURE:
<223> OTHER INFORMATION: example of silent variation of nucleotides 1-18
      of SEQ ID NO:10

<400> SEQUENCE: 19

```
atgttattgt gtaccgcc                                                    18
```

<210> SEQ ID NO 20
<211> LENGTH: 5
<212> TYPE: PRT
<213> ORGANISM: artificial
<220> FEATURE:
<223> OTHER INFORMATION: example of conservative substitution of amino
      acids 5-10 of hT1R1

<400> SEQUENCE: 20

```
Ser Thr Lys Met Met
1               5
```

<210> SEQ ID NO 21
<211> LENGTH: 5
<212> TYPE: PRT
<213> ORGANISM: artificial
<220> FEATURE:
<223> OTHER INFORMATION: example of conservative substitution of amino
      acids 5-10 of hT1R1

<400> SEQUENCE: 21

```
Thr Ser Lys Val Ile
```

```
<210> SEQ ID NO 22
<211> LENGTH: 31
<212> TYPE: DNA
<213> ORGANISM: Artificial
<220> FEATURE:
<223> OTHER INFORMATION: synthetic oligonucleotide used to obtain 5' end
      of hT1R2

<400> SEQUENCE: 22
cgcagcaaag ccgggaagcg caccttgtct c                                  31
```

What is claimed is:

1. An isolated or recombinant polypeptide that comprises one or more of the following:
   (a) an amino acid sequence that is at least 95% identical to SEQ ID NO: 1 as determined by BLASTP using default parameters;
   (b) an amino acid sequence that is at least 95% identical to SEQ ID NO: 1 as determined by BLASTP using default parameters and that comprises one or more domains of an hT1R1 polypeptide of SEQ ID NO. 1; or
   (c) an amino acid sequence that is encoded by a nucleic acid comprising SEQ ID NO: 10.

2. The isolated or recombinant polypeptide of claim 1, wherein the polypeptide comprises an amino acid sequence of: SEQ ID NO: 1.

3. The isolated or recombinant polypeptide of claim 1, wherein the polypeptide comprises a mature hT1R1 protein comprising SEQ ID NO: 1.

4. The isolated polypeptide of claim 1, wherein the polypeptide comprises an hT1R1 polypeptide domain selected from the group consisting of:
   an amino-terminal extracellular domain;
   an extracellular domain located between TM2 and TM3, between TM4 and TM5, or between TM6 and TM7;
   a transmembrane (TM) domain;
   an intracellular domain located between TM1 and TM2, between TM3 and TM4, or between TM5 and TM6; and
   a carboxyl-terminal intracellular domain.

5. The polypeptide of claim 1, wherein the polypeptide is a heteromer.

6. The polypeptide of claim 1, wherein the polypeptide is a homomultimer.

7. The polypeptide of claim 1, wherein the polypeptide is a heteromer that comprises more than one polypeptide selected from the group consisting of SEQ ID NO: 1, SEQ ID NO:4, and SEQ ID NO:7, or a conservative variation thereof.

8. A biosensor comprising the polypeptide of claim 1.

9. An isolated or recombinant polypeptide made by a method for producing a recombinant or isolated polypeptide, the method comprising:
   (i) culturing a cell comprising an expression vector encoding the recombinant or isolated polypeptide of claim 1, under conditions suitable for expression of the isolated or recombinant polypeptide; and,
   (ii) purifying the polypeptide such that the polypeptide is enriched at least 5× as compared to the polypeptide present in step (i).

10. The polypeptide of claim 1, wherein the polypeptide comprises an amino acid sequence that is more than 96% identical to SEQ ID NO:1, as determined by BLASTP using default parameters.

11. The polypeptide of claim 1, wherein the polypeptide comprises an amino acid sequence that is at least 98% identical to SEQ ID NO: 1, as determined by BLASTP using default parameters.

12. The polypeptide of claim 1, wherein the polypeptide comprises an amino acid sequence that is at least 99% identical to SEQ ID NO:1, as determined by BLASTP using default parameters.

13. The polypeptide of claim 1, wherein the polypeptide is more than 96% identical to a polypeptide of SEQ ID NO:1, as determined by BLASTP using default parameters.

14. The polypeptide of claim 1, wherein the polypeptide is at least 98% identical to a polypeptide of SEQ ID NO: 1, as determined by BLASTP using default parameters.

15. The polypeptide of claim 1, wherein the polypeptide is at least 99% identical to a polypeptide of SEQ ID NO: 1, as determined by BLASTP using default parameters.

* * * * *